(12) United States Patent
Tran

(10) Patent No.: US 8,684,922 B2
(45) Date of Patent: Apr. 1, 2014

(54) HEALTH MONITORING SYSTEM

(71) Applicant: Bao Tran, Saratoga, CA (US)

(72) Inventor: Bao Tran, Saratoga, CA (US)

( * ) Notice: Subject to any disclaimer, the term of this patent is extended or adjusted under 35 U.S.C. 154(b) by 0 days.

(21) Appl. No.: 13/707,682

(22) Filed: Dec. 7, 2012

(65) Prior Publication Data

US 2013/0095459 A1 Apr. 18, 2013

(51) Int. Cl.
*A61B 5/00* (2006.01)

(52) U.S. Cl.
USPC .......................................... 600/300

(58) Field of Classification Search
USPC .................. 600/300, 301, 595; 705/2, 4
See application file for complete search history.

(56) References Cited

U.S. PATENT DOCUMENTS

| | | | |
|---|---|---|---|
| 4,234,926 A | 11/1980 | Wallace et al. |
| 4,275,742 A | 6/1981 | Faisandier |
| 4,320,767 A | 3/1982 | Villa-Real |
| 4,412,545 A | 11/1983 | Okino et al. |
| 4,420,000 A | 12/1983 | Bailey |
| 4,537,202 A | 8/1985 | Mancini et al. |
| 4,557,270 A | 12/1985 | John |
| 4,595,018 A | 6/1986 | Rantala |
| 4,656,319 A | 4/1987 | Bially |
| 4,679,144 A | 7/1987 | Cox et al. |
| 4,778,449 A | 10/1988 | Weber et al. |
| 4,807,642 A | 2/1989 | Brown |
| 4,819,648 A | 4/1989 | Ko |
| 4,862,359 A | 8/1989 | Trivedi et al. |
| 4,869,261 A | 9/1989 | Penaz |
| 4,880,013 A | 11/1989 | Chio |
| 4,907,597 A | 3/1990 | Chamoun |
| 4,922,229 A | 5/1990 | Guenst |
| 4,964,411 A | 10/1990 | Johnson et al. |
| 5,090,418 A | 2/1992 | Squires et al. |
| RE34,015 E | 8/1992 | Duffy |
| 5,140,990 A | 8/1992 | Jones et al. |
| 5,161,529 A | 11/1992 | Stotts et al. |
| 5,162,991 A | 11/1992 | Chio |
| 5,271,411 A | 12/1993 | Ripley et al. |
| 5,285,793 A | 2/1994 | Slovut et al. |
| 5,287,859 A | 2/1994 | John |
| 5,309,916 A | 5/1994 | Hatschek |
| 5,331,969 A | 7/1994 | Silberstein |
| 5,361,775 A | 11/1994 | Remes et al. |
| 5,365,426 A | 11/1994 | Siegel et al. |
| 5,368,039 A | 11/1994 | Moses |
| 5,370,126 A | 12/1994 | Clifford, Jr. |
| 5,375,610 A | 12/1994 | LaCourse et al. |
| 5,434,419 A | 7/1995 | Decupper |
| 5,435,316 A | 7/1995 | Kruse |

(Continued)

OTHER PUBLICATIONS

U.S. Appl. No. 10/938,783, Wen.

*Primary Examiner* — Brian T Gedeon
(74) *Attorney, Agent, or Firm* — Tran & Associates

(57) ABSTRACT

A monitoring system for a person includes a processor coupled to one or more wireless nodes; a wearable mobile appliance in communication with the client and one or more wireless nodes; and one or more computer implemented agents with rules executed by the processor, the rules being selected to respond to a client communication relating to a predetermined health condition, each agent communicating with another computer implemented agent, the client or the treatment professional, and upon receiving a communication from the client, the processor selecting one or more computer implemented agents to reply with an instruction on healthy client behavior.

26 Claims, 27 Drawing Sheets

(56) References Cited

U.S. PATENT DOCUMENTS

| | | |
|---|---|---|
| 5,438,607 A | 8/1995 | Przygoda, Jr. et al. |
| 5,441,047 A | 8/1995 | David et al. |
| 5,458,620 A | 10/1995 | Adams et al. |
| 5,462,065 A | 10/1995 | Cusimano |
| 5,497,781 A | 3/1996 | Chen et al. |
| 5,505,208 A | 4/1996 | Toomim et al. |
| 5,513,651 A | 5/1996 | Cusimano et al. |
| 5,544,649 A | 8/1996 | David et al. |
| 5,544,661 A | 8/1996 | Davis et al. |
| 5,546,953 A | 8/1996 | Garfield |
| 5,551,435 A | 9/1996 | Sramek |
| 5,551,438 A | 9/1996 | Moses |
| 5,579,001 A | 11/1996 | Dempsey et al. |
| 5,579,775 A | 12/1996 | Dempsey et al. |
| 5,584,298 A | 12/1996 | Kabal |
| 5,623,939 A | 4/1997 | Garfield |
| 5,633,910 A | 5/1997 | Cohen |
| 5,652,570 A | 7/1997 | Lepkofker |
| 5,662,118 A | 9/1997 | Skubick |
| 5,671,741 A | 9/1997 | Lang et al. |
| 5,683,425 A | 11/1997 | Hauptmann |
| 5,692,215 A | 11/1997 | Kutzik et al. |
| 5,694,940 A | 12/1997 | Unger et al. |
| 5,708,417 A | 1/1998 | Tallman et al. |
| 5,709,215 A | 1/1998 | Perttu et al. |
| 5,710,551 A | 1/1998 | Ridgeway |
| 5,720,771 A | 2/1998 | Snell |
| 5,722,420 A | 3/1998 | Lee |
| 5,733,230 A | 3/1998 | Sawchuck et al. |
| 5,738,104 A | 4/1998 | Lo et al. |
| 5,738,105 A | 4/1998 | Kroll |
| 5,743,268 A | 4/1998 | Kabal |
| 5,772,603 A | 6/1998 | Ohlsson |
| 5,775,330 A | 7/1998 | Kangas et al. |
| 5,776,073 A | 7/1998 | Garfield et al. |
| 5,785,960 A | 7/1998 | Rigg et al. |
| 5,788,643 A | 8/1998 | Feldman |
| 5,857,975 A | 1/1999 | Golub |
| 5,865,755 A | 2/1999 | Golub |
| 5,876,350 A | 3/1999 | Lo et al. |
| 5,935,077 A | 8/1999 | Ogle |
| 5,945,112 A | 8/1999 | Flynn et al. |
| 5,964,719 A | 10/1999 | Costello et al. |
| 5,967,975 A | 10/1999 | Ridgeway |
| 5,987,519 A | 11/1999 | Peifer et al. |
| 5,996,889 A | 12/1999 | Fuchs et al. |
| 6,002,957 A | 12/1999 | Finneran |
| 6,004,312 A | 12/1999 | Finneran et al. |
| 6,010,454 A | 1/2000 | Arieff et al. |
| 6,014,626 A | 1/2000 | Cohen |
| 6,032,035 A | 2/2000 | Webster et al. |
| 6,038,469 A | 3/2000 | Karlsson et al. |
| 6,047,202 A | 4/2000 | Finneran et al. |
| 6,050,940 A | 4/2000 | Braun et al. |
| 6,052,619 A | 4/2000 | John |
| 6,056,671 A | 5/2000 | Marmer |
| 6,063,051 A | 5/2000 | Stern |
| 6,070,140 A | 5/2000 | Tran |
| 6,076,011 A | 6/2000 | Hoover |
| 6,108,685 A | 8/2000 | Kutzik et al. |
| 6,171,237 B1 | 1/2001 | Avitall et al. |
| 6,175,308 B1 | 1/2001 | Tallman et al. |
| 6,176,831 B1 | 1/2001 | Voss et al. |
| 6,184,797 B1 | 2/2001 | Stark et al. |
| 6,228,034 B1 | 5/2001 | Voss et al. |
| 6,230,056 B1 | 5/2001 | Kroll |
| 6,246,894 B1 | 6/2001 | Steur et al. |
| 6,280,393 B1 | 8/2001 | Granger et al. |
| 6,287,252 B1 | 9/2001 | Lugo |
| 6,299,583 B1 | 10/2001 | Eggers et al. |
| 6,336,900 B1 | 1/2002 | Alleckson et al. |
| 6,364,834 B1 | 4/2002 | Reuss et al. |
| 6,364,842 B1 | 4/2002 | Amano et al. |
| 6,368,283 B1 | 4/2002 | Xu et al. |
| 6,374,614 B2 | 4/2002 | Prueitt |
| 6,375,614 B1 | 4/2002 | Braun et al. |
| 6,398,727 B1 | 6/2002 | Bui et al. |
| 6,406,426 B1 | 6/2002 | Reuss et al. |
| 6,413,223 B1 | 7/2002 | Yang et al. |
| 6,416,480 B1 | 7/2002 | Nenov |
| 6,433,690 B2 | 8/2002 | Petelenz et al. |
| 6,440,067 B1 | 8/2002 | DeLuca et al. |
| 6,443,906 B1 | 9/2002 | Ting et al. |
| 6,445,299 B1 | 9/2002 | Rojas, Jr. |
| 6,466,816 B2 | 10/2002 | Granger et al. |
| 6,473,640 B1 | 10/2002 | Erlebacher |
| 6,475,146 B1 | 11/2002 | Frelburger et al. |
| 6,475,153 B1 | 11/2002 | Khair et al. |
| 6,487,442 B1 | 11/2002 | Wood |
| 6,514,211 B1 | 2/2003 | Baura |
| 6,515,593 B1 | 2/2003 | Stark et al. |
| 6,533,729 B1 | 3/2003 | Khair et al. |
| 6,544,173 B2 | 4/2003 | West et al. |
| 6,544,174 B2 | 4/2003 | West et al. |
| 6,546,269 B1 | 4/2003 | Kurnik |
| 6,554,774 B1 | 4/2003 | Miele |
| 6,556,860 B1 | 4/2003 | Groenewegen |
| 6,595,316 B2 | 7/2003 | Cybulski et al. |
| 6,597,944 B1 | 7/2003 | Hadas |
| 6,602,191 B2 * | 8/2003 | Quy ............................ 600/300 |
| 6,605,038 B1 | 8/2003 | Teller et al. |
| 6,609,023 B1 | 8/2003 | Fischer et al. |
| 6,612,984 B1 | 9/2003 | Kerr, II |
| 6,615,074 B2 | 9/2003 | Mickle et al. |
| 6,615,075 B2 | 9/2003 | Mlynash et al. |
| 6,616,613 B1 | 9/2003 | Goodman |
| 6,660,042 B1 | 12/2003 | Curcie et al. |
| 6,661,161 B1 | 12/2003 | Lanzo et al. |
| 6,676,600 B1 | 1/2004 | Conero et al. |
| 6,678,549 B2 | 1/2004 | Cusimano et al. |
| 6,678,551 B2 | 1/2004 | Maalouf et al. |
| 6,687,519 B2 | 2/2004 | Steur et al. |
| 6,705,990 B1 | 3/2004 | Gallant et al. |
| 6,720,984 B1 | 4/2004 | Jorgensen et al. |
| 6,730,038 B2 | 5/2004 | Gallant et al. |
| 6,740,045 B2 | 5/2004 | Amano |
| 6,747,561 B1 | 6/2004 | Reeves |
| 6,760,620 B2 | 7/2004 | Sippens Groenewegen |
| 6,783,492 B2 | 8/2004 | Dominguez et al. |
| 6,804,656 B1 | 10/2004 | Rosenfeld et al. |
| 6,816,266 B2 | 11/2004 | Varshneya et al. |
| 6,829,501 B2 | 12/2004 | Nielsen et al. |
| 6,832,251 B1 | 12/2004 | Gelvin et al. |
| 6,834,436 B2 | 12/2004 | Townsend et al. |
| 6,843,771 B2 | 1/2005 | Lo et al. |
| 6,856,291 B2 | 2/2005 | Mickle et al. |
| 6,865,409 B2 | 3/2005 | Getsla et al. |
| 6,871,211 B2 | 3/2005 | Labounty et al. |
| 6,882,128 B1 | 4/2005 | Rahmel et al. |
| 6,887,202 B2 | 5/2005 | Currie et al. |
| 6,898,460 B2 | 5/2005 | Hoctor et al. |
| 6,907,288 B2 | 6/2005 | Daum |
| 6,912,420 B2 | 6/2005 | Scheiner et al. |
| 6,944,496 B2 | 9/2005 | Jeong et al. |
| 6,961,285 B2 | 11/2005 | Niemiec et al. |
| 6,965,794 B2 | 11/2005 | Brody |
| 6,973,344 B2 | 12/2005 | Finneran et al. |
| 6,974,419 B1 | 12/2005 | Voss et al. |
| 6,975,206 B2 | 12/2005 | Reining |
| 6,980,852 B2 | 12/2005 | Jersey-Willuhn et al. |
| 6,989,751 B2 | 1/2006 | Richards |
| 7,004,907 B2 | 2/2006 | Banet et al. |
| 7,011,629 B2 | 3/2006 | Bulat |
| 7,035,679 B2 | 4/2006 | Addison et al. |
| 7,043,293 B1 | 5/2006 | Baura |
| 8,303,500 B2 * | 11/2012 | Raheman .................. 600/301 |
| 2002/0027164 A1 * | 3/2002 | Mault et al. ............. 235/462.46 |
| 2002/0120184 A1 | 8/2002 | Beck et al. |
| 2003/0004421 A1 | 1/2003 | Ting et al. |
| 2003/0125635 A1 | 7/2003 | Maalouf et al. |
| 2003/0135127 A1 | 7/2003 | Sackner et al. |
| 2003/0216630 A1 | 11/2003 | Jersey-Willuhn et al. |
| 2003/0216662 A1 | 11/2003 | Jersey-Willuhn et al. |
| 2003/0216663 A1 | 11/2003 | Jersey-Willuhn et al. |

(56) References Cited

U.S. PATENT DOCUMENTS

| | | |
|---|---|---|
| 2003/0231115 A1 | 12/2003 | Stanners et al. |
| 2004/0044273 A1 | 3/2004 | Keith et al. |
| 2004/0102683 A1 | 5/2004 | Khanuja et al. |
| 2004/0122487 A1 | 6/2004 | Hatlestad et al. |
| 2004/0138568 A1 | 7/2004 | Lo et al. |
| 2004/0167409 A1 | 8/2004 | Lo et al. |
| 2004/0167417 A1 | 8/2004 | Schulhauser et al. |
| 2004/0220490 A1 | 11/2004 | Appel et al. |
| 2004/0254493 A1 | 12/2004 | Chervin et al. |
| 2004/0260188 A1 | 12/2004 | Syed et al. |
| 2004/0267148 A1 | 12/2004 | Arand et al. |
| 2005/0038345 A1 | 2/2005 | Gorgenberg et al. |
| 2005/0061568 A1 | 3/2005 | Schondorf et al. |
| 2005/0099387 A1 | 5/2005 | Matsumoto |
| 2005/0113630 A1 | 5/2005 | Fox et al. |
| 2005/0113710 A1 | 5/2005 | Stahmann et al. |
| 2005/0115561 A1 | 6/2005 | Stahmann et al. |
| 2005/0143667 A1 | 6/2005 | Park et al. |
| 2005/0148882 A1 | 7/2005 | Banet |
| 2005/0194926 A1 | 9/2005 | Di Stefano et al. |
| 2005/0201585 A1 | 9/2005 | Jannard et al. |
| 2005/0209521 A1 | 9/2005 | Kettunen et al. |
| 2005/0222515 A1 | 10/2005 | Polyshchuk et al. |
| 2005/0228244 A1 | 10/2005 | Banet et al. |
| 2005/0228299 A1 | 10/2005 | Banet et al. |
| 2005/0228316 A1 | 10/2005 | Morgenstern et al. |
| 2005/0240086 A1 | 10/2005 | Akay et al. |
| 2005/0240523 A1 | 10/2005 | Richardson et al. |
| 2005/0245831 A1 | 11/2005 | Banet et al. |
| 2005/0261594 A1 | 11/2005 | Banet et al. |
| 2005/0261598 A1 | 11/2005 | Banet et al. |
| 2005/0278409 A1 | 12/2005 | Kutzik et al. |
| 2006/0009697 A1 | 1/2006 | Banet et al. |
| 2006/0009698 A1 | 1/2006 | Banet et al. |
| 2006/0047215 A1 | 3/2006 | Newman et al. |
| 2006/0079801 A1 | 4/2006 | DeLuca et al. |
| 2006/0082727 A1 | 4/2006 | Bolger et al. |
| 2006/0084878 A1 | 4/2006 | Banet et al. |
| 2006/0094975 A1 | 5/2006 | Manto |
| 2006/0105357 A1 | 5/2006 | Benesch et al. |
| 2010/0111383 A1* | 5/2010 | Boushey et al. .............. 382/128 |

\* cited by examiner

| |
|---|
| Place a calibration sheet with known dots at a known distance and perpendicular to a camera view |
| Take snap shot of the sheet, and correlate the position of the dots to the camera image |
| Place a different calibration sheet that contains known dots at another different known distance and perpendicular to camera view. |
| Take snap shot of the sheet and correlate the position of the dots to the camera image |
| Smooth the dots to the pixels to minimize digitization errors |
| For each pixel, draw a line from Dot1(x,y,z) to Dot2 (x, y, z) defining a cone center where the camera can view |

FIG. 2A

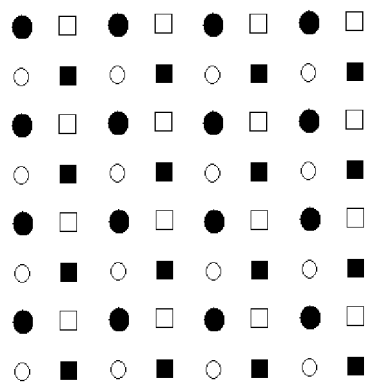

FIG. 2B

| |
|---|
| Set up mesh network appliances (1000) |
| Determine patient position using in-door positioning system (1002) |
| Determine patient movement using accelerometer output (1004) |
| Determine vital parameter including patient heart rate (1006) |
| Determine if patient needs assistance based on in-door position, fall detection and vital parameter (1008) |
| Confirm prior to calling third party (1010) |
| If confirmed or non-responsive, make connection with third party and send voice over mesh network to appliance worn by the patient (1012) |
| If needed, call emergency personnel to get medical care (1014) |

FIG. 5

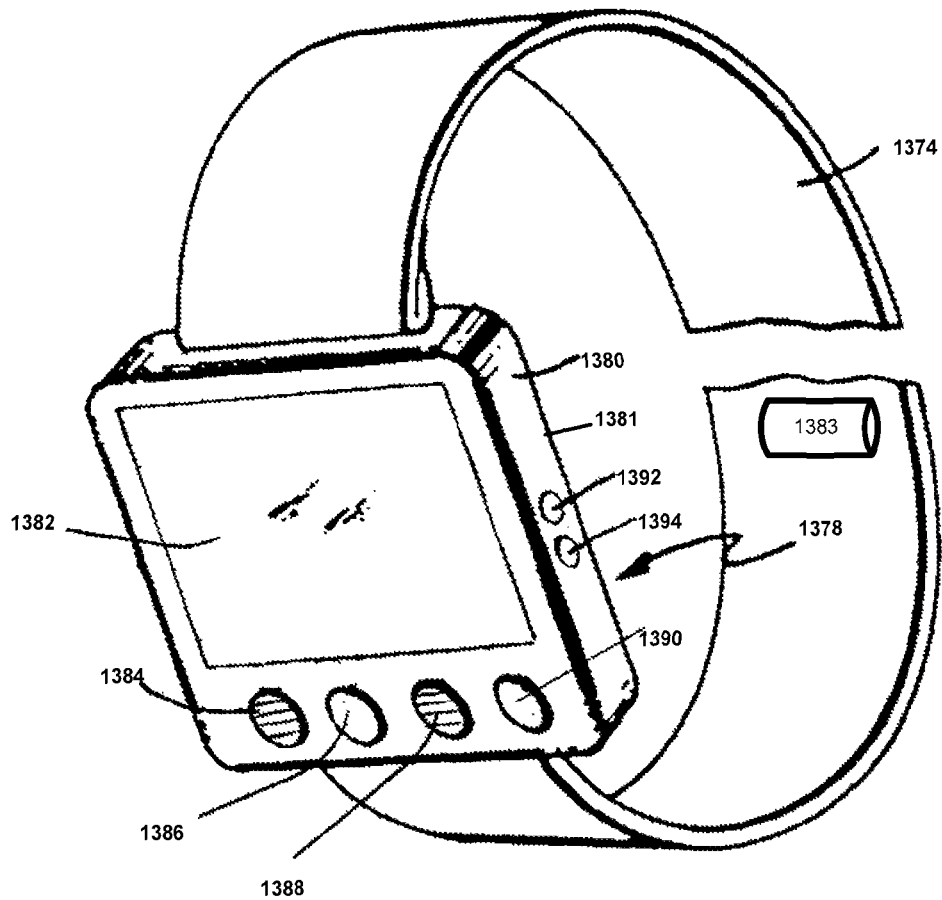

FIG. 6A

| |
|---|
| Generate a blood pressure model of a patient (2002) |
| Determine a blood flow velocity using a piezoelectric transducer (2004) |
| Provide the blood flow velocity to the blood pressure model to continuously estimate blood pressure (2006) |

| Attach monitoring device and calibration device to patient (2010) | Determine blood flow velocity from the monitoring device and actual blood pressure from the calibration device (2012) | Generate a blood pressure model based on the blood flow velocity and the actual blood pressure (2014) | Remove calibration device (2016) | Determine blood flow velocity (2018) | Provide blood flow velocity to the blood pressure model to estimate blood pressure (2020) |
|---|---|---|---|---|---|

| Run blood pressure master agent (3050) |
|---|
| Run diabetic master agent (3052) |
| Run weight loss agent (3054) |

FIG. 18A

| Register patient (3100) |
|---|
| Collect information on patient (3102) |
| Select treatment template based on treatment plan for similar patients (3104) |
| Generate treatment plan from template and customize treatment plan (3106) |
| Collect data on patient compliance with treatment plan (3108) |
| Accumulate reward points for patient to encourage healthy activities, such as healthy dieting and physical activities such as jogging, walking, or gardening (3110) |
| Compare patient progress with other patients (3112) |
| Send automatic encouraging messages to patients (3114) |
| Periodically show patient status to doctor (3116) |
| Present recommendations to doctor on preventive steps, such as check-ups and basic blood tests (3118) |
| Automatically schedule in person consultation for patient and doctor (3120) |

FIG. 18B

| |
|---|
| Determine and recommend Diet (3130) |
| Capture Images of Meals Using Phone Camera (3132) |
| Translate Images of Meals into Calories (3134) |
| Correlate Actual Diet with Recommended Diet (3136) |

FIG. 18C

| |
|---|
| Determine and recommend Exercise Routine (3140) |
| Capture Activity Using MEMS sensors (3142) |
| Correlate Actual Activity with Recommended Exercise Routine (3144) |

HEALTH MONITORING SYSTEM

BACKGROUND

This invention relates generally to methods and apparatus for communicating health instructions to users.

Healthcare costs around the world have been rising. One reason is that, obesity is common, serious and costly. A Duke University study suggests that by 2030, about 42% of Americans will be obese, which is up from 36% in 2012 and will cost about $550 billion dollars. Even small reductions in obesity prevalence "could result in substantial savings," wrote the authors. Obesity-related conditions increase the odds of heart disease, stroke, type 2 diabetes and certain types of cancer, some of the leading causes of preventable death. In 2008, medical costs associated with obesity were estimated at $147 billion; the medical costs for people who are obese were $1,429 higher than those of normal weight.

Obesity affects some groups more than others. Non-Hispanic blacks have the highest age-adjusted rates of obesity (49.5%) compared with Mexican Americans (40.4%), all Hispanics (39.1%) and non-Hispanic whites (34.3%). Among non-Hispanic black and Mexican-American men, those with higher incomes are more likely to be obese than those with low income. Higher income women are less likely to be obese than low-income women. There is no significant relationship between obesity and education among men. Among women, however, there is a trend—those with college degrees are less likely to be obese compared with less educated women. Thus, education appears to be key. Between 1988-1994 and 2007-2008 the prevalence of obesity increased in adults at all income and education levels.

A government solution has been suggested. For example, a ban on the use of trans fats in NY restaurants has sharply reduced the consumption of these unhealthy fats among fast-food customers. However, the government and regulation may not be the best way to solve the problem.

To treat obesity in a cost effective manner, coordination is needed among different service providers such as dieticians, doctors, and exercise coaches. However, planning information, alerts and reminders may be haphazardly and intermittently distributed to doctors, clinicians, or their staff with existing healthcare appointment and scheduling systems and do not support multi-vendor calendaring system that shares information among the different providers. This occurs in other treatments as well. For example, in the case of a patient scheduled for radiation therapy, an existing system may be aware of a necessary number of appointments and treatment orders, but these numbers typically are not compatible with the (e.g., one or more) treatment plans involved. Consequently, a clinician needs to work out a referral connection manually for each appointment. The existing systems also require manual coordination of appointments with treatment plan goals and treatment plan results which occupies a significant amount of clinician time in gathering, collating and analyzing information.

One way to monitor the impact of obesity is to monitor blood pressure. As discussed in U.S. Pat. No. 6,514,211, three well known techniques have been used to non-invasively monitor a subject's arterial blood pressure waveform: auscultation, oscillometry, and tonometry. The auscultation and oscillometry techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Occlusive cuff instruments of the kind described briefly above generally have been effective in sensing long-term trends in a subject's blood pressure, but they have been ineffective in sensing short-term blood pressure variations.

The '211 patent discloses blood pressure measurement by determining the mean arterial blood pressure (MAP) of a subject during tonometric conditions. The apparatus has one or more pressure and ultrasound transducers placed over the radial artery of a human subject's wrist, the latter transmitting and receiving acoustic energy so as to permit the measurement of blood velocity during periods of variable compression of the artery. During compression, the ultrasound velocity waveforms are recorded and processed using time-frequency analysis. The time at which the mean time-frequency distribution is maximal corresponds to the time at which the transmural pressure equals zero, and the mean pressure read by the transducer equals the mean pressure within the artery. In another aspect of the invention, the ultrasound transducer is used to position the transducer over the artery such that the accuracy of the measurement is maximized.

SUMMARY

A monitoring system for a person includes a processor coupled to one or more wireless nodes; a wearable mobile appliance in communication with the client and one or more wireless nodes; and one or more computer implemented agents with rules executed by the processor, the rules being selected to respond to a client communication relating to a predetermined health condition, each agent communicating with another computer implemented agent, the client or the treatment professional, and upon receiving a communication from the client, the processor selecting one or more computer implemented agents to reply with an instruction on healthy client behavior.

Advantages of the preferred embodiment may include one or more of the following. The system turns obesity and overweight into preventable phenomena, and the myriad health problems associated with them. The system not saves money and enhances lives by continued efforts at getting the weight off. The system brings awareness of the serious health issues—physical and mental—that are linked to being overweight or obese, along with the tried and true lifestyle changes like diet and exercise, as ways for battling the obesity epidemic.

In another aspect, a heart monitoring system for a person includes one or more wireless nodes; and a wearable appliance in communication with the one or more wireless nodes, the appliance continuously monitoring patient vital signs or other data such as cardiac abnormalities. Embodiments can monitor heart rate, heart rate variability, respiratory rate, fluid status, posture and activity.

In a further aspect, a monitoring system for a person includes one or more wireless nodes; and a wristwatch having a wireless transceiver adapted to communicate with the one or more wireless nodes; and an accelerometer to detect a dangerous condition and to generate a warning when the dangerous condition is detected.

In yet another aspect, a heart monitoring system for a person includes one or more wireless nodes forming a wireless network and a wearable appliance having a sound transducer coupled to the wireless transceiver; and a heart disease recognizer coupled to the sound transducer to determine cardiovascular health and to transmit heart sound over the wireless network to a remote listener if the recognizer identifies a cardiovascular problem. The heart sound being transmitted may be compressed to save transmission bandwidth.

In another aspect, a monitoring system for a person includes one or more wireless nodes forming a wireless network; and a wearable appliance having a wireless transceiver adapted to communicate with the one or more wireless nodes; and a heartbeat detector coupled to the wireless transceiver. Embodiments may also include an accelerometer to detect a dangerous condition such as a falling condition and to generate a warning when the dangerous condition is detected.

Implementations of the above aspect may include one or more of the following. The wristwatch determines position based on triangulation. The wristwatch determines position based on RF signal strength and RF signal angle. A switch detects a confirmatory signal from the person. The confirmatory signal includes a head movement, a hand movement, or a mouth movement. The confirmatory signal includes the person's voice. A processor in the system executes computer readable code to transmit a help request to a remote computer. The code can encrypt or scramble data for privacy. The processor can execute voice over IP (VOIP) code to allow a user and a remote person to audibly communicate with each other. The voice communication system can include Zigbee VOIP or Bluetooth VOIP or 802.XX VOIP. The remote person can be a doctor, a nurse, a medical assistant, or a caregiver. The system includes code to store and analyze patient information. The patient information includes medicine taking habits, eating and drinking habits, sleeping habits, or excise habits. A patient interface is provided on a user computer for accessing information and the patient interface includes in one implementation a touch screen; voice-activated text reading; and one touch telephone dialing. The processor can execute code to store and analyze information relating to the person's ambulation. A global positioning system (GPS) receiver can be used to detect movement and where the person falls. The system can include code to map the person's location onto an area for viewing. The system can include one or more cameras positioned to capture three dimensional (3D) video of the patient; and a server coupled to the one or more cameras, the server executing code to detect a dangerous condition for the patient based on the 3D video and allow a remote third party to view images of the patient when the dangerous condition is detected.

In another aspect, a monitoring system for a person includes one or more wireless bases; and a cellular telephone having a wireless transceiver adapted to communicate with the one or more wireless bases; and an accelerometer to detect a dangerous condition and to generate a warning when the dangerous condition is detected.

In yet another aspect, a monitoring system includes one or more cameras to determine a three dimensional (3D) model of a person; means to detect a dangerous condition based on the 3D model; and means to generate a warning when the dangerous condition is detected.

In another aspect, a method to detect a dangerous condition for an infant includes placing a pad with one or more sensors in the infant's diaper; collecting infant vital parameters; processing the vital parameter to detect SIDS onset; and generating a warning.

Advantages of these embodiments may include one or more of the following. The system for non-invasively and continually monitors a subject's arterial blood pressure, with reduced susceptibility to noise and subject movement, and relative insensitivity to placement of the apparatus on the subject. The system does not need frequent recalibration of the system while in use on the subject.

In particular, it allows patients to conduct a low-cost, comprehensive, real-time monitoring of their blood pressure. Using the web services software interface, the invention then avails this information to hospitals, home-health care organizations, insurance companies, pharmaceutical agencies conducting clinical trials and other organizations. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

The wearable appliance is small, easily worn by the patient during periods of exercise or day-to-day activities, and non-invasively measures blood pressure can be done in a matter of seconds without affecting the patient. An on-board or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

Other advantages of the invention may include one or more of the following. The wearable appliance provides an in-depth, cost-effective mechanism to evaluate a patient's cardiac condition. Certain cardiac conditions can be controlled, and in some cases predicted, before they actually occur. Moreover, data from the patient can be collected and analyzed while the patient participates in their normal, day-to-day activities.

In cases where the device has fall detection in addition to blood pressure measurement, other advantages of the invention may include one or more of the following. The system provides timely assistance and enables elderly and disabled individuals to live relatively independent lives. The system monitors physical activity patterns, detects the occurrence of falls, and recognizes body motion patterns leading to falls. Continuous monitoring of patients is done in an accurate, convenient, unobtrusive, private and socially acceptable manner since a computer monitors the images and human involvement is allowed only under pre-designated events. The patient's privacy is preserved since human access to videos of the patient is restricted: the system only allows human viewing under emergency or other highly controlled conditions designated in advance by the user. When the patient is healthy, people cannot view the patient's video without the patient's consent. Only when the patient's safety is threatened would the system provide patient information to authorized medical providers to assist the patient. When an emergency occurs, images of the patient and related medical data can be compiled and sent to paramedics or hospital for proper preparation for pick up and check into emergency room.

The system allows certain designated people such as a family member, a friend, or a neighbor to informally check on the well-being of the patient. The system is also effective in containing the spiraling cost of healthcare and outpatient care as a treatment modality by providing remote diagnostic capability so that a remote healthcare provider (such as a doctor, nurse, therapist or caregiver) can visually communicate with the patient in performing remote diagnosis. The system allows skilled doctors, nurses, physical therapists, and other scarce resources to assist patients in a highly efficient manner since they can do the majority of their functions remotely.

Additionally, a sudden change of activity (or inactivity) can indicate a problem. The remote healthcare provider may receive alerts over the Internet or urgent notifications over the phone in case of such sudden accident indicating changes. Reports of health/activity indicators and the overall well being of the individual can be compiled for the remote healthcare provider. Feedback reports can be sent to monitored subjects, their designated informal caregiver and their remote healthcare provider. Feedback to the individual can encourage the individual to remain active. The content of the report may be tailored to the target recipient's needs, and can present the information in a format understandable by an elder person unfamiliar with computers, via an appealing patient interface. The remote healthcare provider will have access to the health and well-being status of their patients without being intrusive, having to call or visit to get such information interrogatively. Additionally, remote healthcare provider can receive a report on the health of the monitored subjects that will help them evaluate these individuals better during the short routine check up visits. For example, the system can perform patient behavior analysis such as eating/drinking/smoke habits and medication compliance, among others.

Yet other advantages of the system may include one or more of the following. The patient's home equipment is simple to use and modular to allow for the accommodation of the monitoring device to the specific needs of each patient. Moreover, the system is simple to install. Regular monitoring of the basic wellness parameters provides significant benefits in helping to capture adverse events sooner, reduce hospital admissions, and improve the effectiveness of medications, hence, lowering patient care costs and improving the overall quality of care. Suitable users for such systems are disease management companies, health insurance companies, self-insured employers, medical device manufacturers and pharmaceutical firms.

The system reduces costs by automating data collection and compliance monitoring, and hence reduce the cost of nurses for hospital and nursing home applications. At-home vital signs monitoring enables reduced hospital admissions and lower emergency room visits of chronic patients. Operators in the call centers or emergency response units get high quality information to identify patients that need urgent care so that they can be treated quickly, safely, and cost effectively. The Web based tools allow easy access to patient information for authorized parties such as family members, neighbors, physicians, nurses, pharmacists, caregivers, and other affiliated parties to improved Quality of Care for the patient.

BRIEF DESCRIPTION OF THE DRAWINGS

FIG. 2A illustrates a process for determining three dimensional (3D) detection while FIG. 2B shows an exemplary calibration sheet.

FIG. 5 illustrates an exemplary process for determining and getting assistance for a patient or user.

FIG. 6A shows an exemplary wrist-watch based assistance device.

FIG. 15F shows an exemplary trending pattern display.

FIGS. 16A-16B show exemplary blood pressure determination processes.

FIG. 17D shows exemplary agents for one treatment scenario.

FIG. 18A shows another exemplary process for monitoring a patient, FIG. 18B shows an exemplary process for monitoring patient food intake, and FIG. 18C shows an exemplary exercise recommendation and monitoring process.

DESCRIPTION

Figure 1:
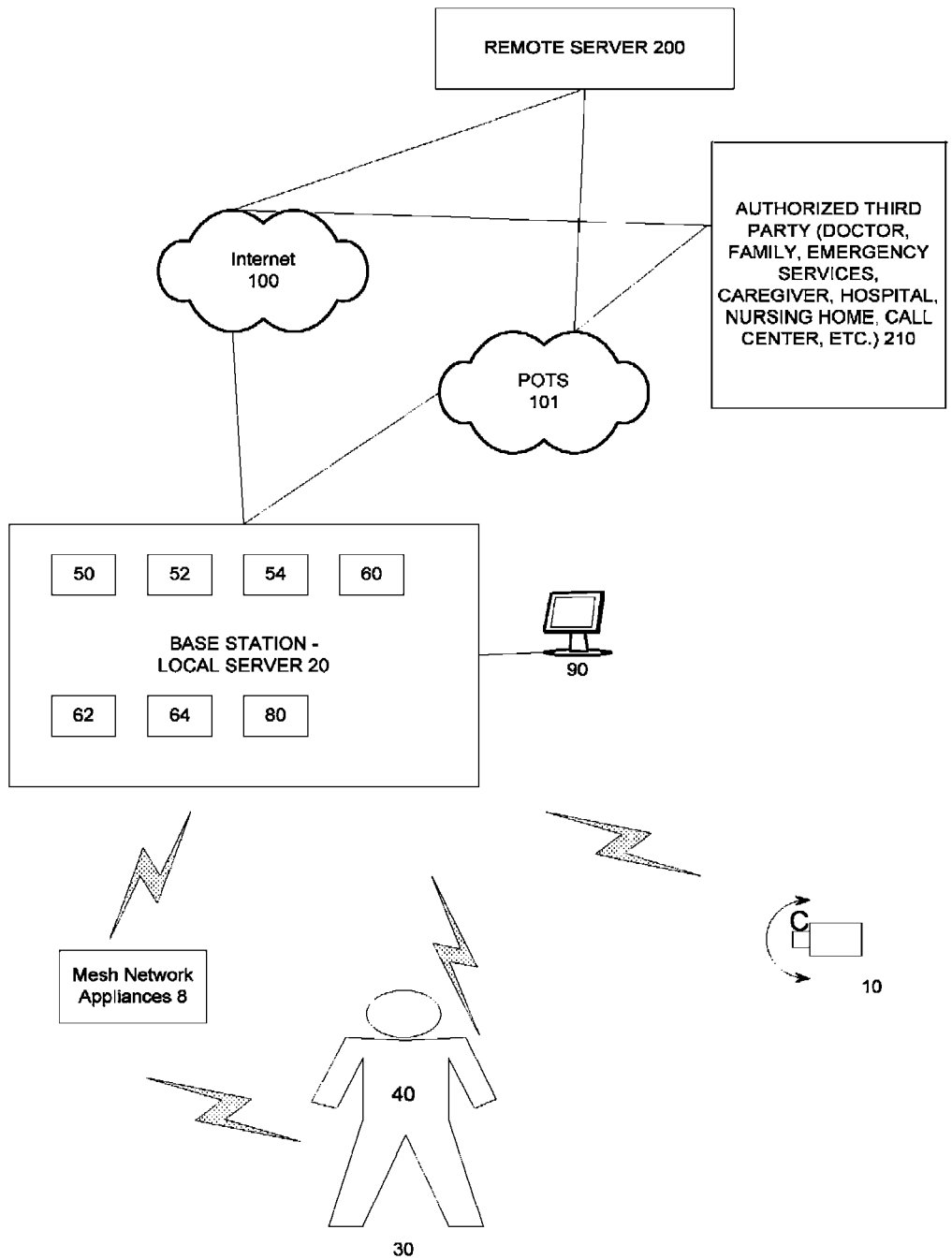
FIG. 1 illustrates an exemplary system for monitoring a person.
Figure 7:
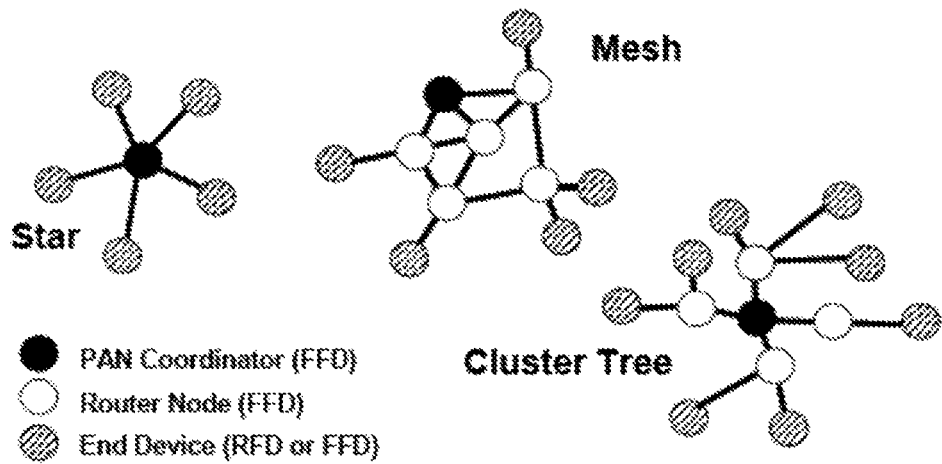
FIG. 7 shows an exemplary mesh network in communication with the wrist-watch device of FIG. 6.

FIG. 1 shows an exemplary patient monitoring system. The system can operate in a home, a nursing home, or a hospital. In this system, one or more mesh network appliances 8 are provided to enable wireless communication in the home monitoring system. Appliances 8 in the mesh network can include home security monitoring devices, door alarm, window alarm, home temperature control devices, fire alarm devices, among others. Appliances 8 in the mesh network can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor, a signal from a medicine cabinet, a signal from a drug container, a signal from a commonly used appliance such as a refrigerator/stove/oven/washer, or a signal from an exercise machine, such as a heart rate. As will be discussed in more detail below, one appliance is a patient monitoring device that can be worn by the patient and includes a single or bi-directional wireless communication link, generally identified by the bolt symbol in FIG. 1, for transmitting data from the appliances 8 to the local hub or receiving station or base station server 20 by way of a wireless radio frequency (RF) link using a proprietary or non-proprietary protocol. For example, within a house, a user may have mesh network appliances that detect window and door contacts, smoke detectors and motion sensors, video cameras, key chain control, temperature monitors, CO and other gas detectors, vibration sensors, and others. A user may have flood sensors and other detectors on a boat. An individual, such as an ill or elderly grandparent, may have access to a panic transmitter or other alarm transmitter. Other sensors and/or detectors may also be included. The user may register these appliances on a central security network by entering the identification code for each registered appliance/device and/or system. The mesh network can be Zigbee network or 802.15 network. More details of the mesh network is shown in FIG. 7 and discussed in more detail below.

A plurality of monitoring cameras 10 may be placed in various predetermined positions in a home of a patient 30. The cameras 10 can be wired or wireless. For example, the cameras can communicate over infrared links or over radio links conforming to the 802X (e.g. 802.11A, 802.11B, 802.11G, 802.15) standard or the Bluetooth standard to a base station/server 20 may communicate over various communication links, such as a direct connection, such a serial connection, USB connection, Firewire connection or may be optically based, such as infrared or wireless based, for example, home RF, IEEE standard 802.11a/b, Bluetooth or the like. In one embodiment, appliances 8 monitor the patient and activates the camera 10 to capture and transmit video to an authorized third party for providing assistance should the appliance 8 detects that the user needs assistance or that an emergency had occurred.

The base station/server 20 stores the patient's ambulation pattern and vital parameters and can be accessed by the patient's family members (sons/daughters), physicians, caretakers, nurses, hospitals, and elderly community. The base station/server 20 may communicate with the remote server 200 by DSL, T-1 connection over a private communication network or a public information network, such as the Internet 100, among others.

The patient 30 may wear one or more wearable patient monitoring appliances such as wrist-watches or clip on devices or electronic jewelry to monitor the patient. One wearable appliance such as a wrist-watch includes sensors 40, for example devices for sensing ECG, EKG, blood pressure, sugar level, among others. In one embodiment, the sensors 40 are mounted on the patient's wrist (such as a wristwatch sensor) and other convenient anatomical locations. Exemplary sensors 40 include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors 40 can individually transmit data to the server 20 using wired or wireless transmission. Alternatively, all sensors 40 can be fed through a common bus into a single transceiver for wired or wireless transmission. The transmission can be done using a magnetic medium such as a floppy disk or a flash memory card, or can be done using infrared or radio network link, among others. The sensor 40 can also include an indoor positioning system or alternatively a global position system (GPS) receiver that relays the position and ambulatory patterns of the patient to the server 20 for mobility tracking.

In one embodiment, the sensors 40 for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The case may be of a number of variations of shape but can be conveniently made a rectangular, approaching a box-like configuration. The wrist-band can be an expansion band or a wristwatch strap of plastic, leather or woven material. The wrist-band further contains an antenna for transmitting or receiving radio frequency signals. The wristband and the antenna inside the band are mechanically coupled to the top and bottom sides of the wrist-watch housing. Further, the antenna is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing contains the processor and associated peripherals to provide the human-machine interface. A display is located on the front section of the housing. A speaker, a microphone, and a plurality of push-button switches and are also located on the front section of housing. An infrared LED transmitter and an infrared LED receiver are positioned on the right side of housing to enable the watch to communicate with another computer using infrared transmission.

In another embodiment, the sensors 40 are mounted on the patient's clothing. For example, sensors can be woven into a single-piece garment (an undershirt) on a weaving machine. A plastic optical fiber can be integrated into the structure during the fabric production process without any discontinuities at the armhole or the seams. An interconnection technology transmits information from (and to) sensors mounted at any location on the body thus creating a flexible "bus" structure. T-Connectors—similar to "button clips" used in clothing—are attached to the fibers that serve as a data bus to carry the information from the sensors (e.g., EKG sensors) on the body. The sensors will plug into these connectors and at the other end similar T-Connectors will be used to transmit the information to monitoring equipment or personal status monitor. Since shapes and sizes of humans will be different, sensors can be positioned on the right locations for all patients and without any constraints being imposed by the clothing. Moreover, the clothing can be laundered without any damage to the sensors themselves. In addition to the fiber optic and specialty fibers that serve as sensors and data bus to carry sensory information from the wearer to the monitoring devices, sensors for monitoring the respiration rate can be integrated into the structure.

In another embodiment, instead of being mounted on the patient, the sensors can be mounted on fixed surfaces such as walls or tables, for example. One such sensor is a motion detector. Another sensor is a proximity sensor. The fixed sensors can operate alone or in conjunction with the cameras 10. In one embodiment where the motion detector operates with the cameras 10, the motion detector can be used to trigger camera recording. Thus, as long as motion is sensed, images from the cameras 10 are not saved. However, when motion is not detected, the images are stored and an alarm may be generated. In another embodiment where the motion detector operates stand alone, when no motion is sensed, the system generates an alarm.

The server 20 also executes one or more software modules to analyze data from the patient. A module 50 monitors the patient's vital signs such as ECG/EKG and generates warnings should problems occur. In this module, vital signs can be collected and communicated to the server 20 using wired or wireless transmitters. In one embodiment, the server 20 feeds the data to a statistical analyzer such as a neural network which has been trained to flag potentially dangerous conditions. The neural network can be a back-propagation neural network, for example. In this embodiment, the statistical analyzer is trained with training data where certain signals are determined to be undesirable for the patient, given his age, weight, and physical limitations, among others. For example, the patient's glucose level should be within a well established range, and any value outside of this range is flagged by the statistical analyzer as a dangerous condition. As used herein, the dangerous condition can be specified as an event or a pattern that can cause physiological or psychological damage to the patient. Moreover, interactions between different vital signals can be accounted for so that the statistical analyzer can take into consideration instances where individually the vital signs are acceptable, but in certain combinations, the vital signs can indicate potentially dangerous conditions. Once trained, the data received by the server 20 can be appropriately scaled and processed by the statistical analyzer. In addition to statistical analyzers, the server 20 can process vital signs using rule-based inference engines, fuzzy logic, as well as conventional if-then logic. Additionally, the server can process vital signs using Hidden Markov Models (HMMs), dynamic time warping, or template matching, among others.

Through various software modules, the system reads video sequence and generates a 3D anatomy file out of the sequence. The proper bone and muscle scene structure are created for head and face. A based profile stock phase shape will be created by this scene structure. Every scene will then be normalized to a standardized viewport.

A module 52 monitors the patient ambulatory pattern and generates warnings should the patient's patterns indicate that the patient has fallen or is likely to fall. 3D detection is used to monitor the patient's ambulation. In the 3D detection process, by putting 3 or more known coordinate objects in a scene, camera origin, view direction and up vector can be calculated and the 3D space that each camera views can be defined.

In one embodiment with two or more cameras, camera parameters (e.g. field of view) are preset to fixed numbers. Each pixel from each camera maps to a cone space. The system identifies one or more 3D feature points (such as a birthmark or an identifiable body landmark) on the patient. The 3D feature point can be detected by identifying the same point from two or more different angles. By determining the intersection for the two or more cones, the system determines the position of the feature point. The above process can be extended to certain feature curves and surfaces, e.g. straight lines, arcs; flat surfaces, cylindrical surfaces. Thus, the system can detect curves if a feature curve is known as a straight line or arc. Additionally, the system can detect surfaces if a feature surface is known as a flat or cylindrical surface. The further the patient is from the camera, the lower the accuracy of the feature point determination. Also, the presence of more cameras would lead to more correlation data for increased accuracy in feature point determination. When correlated feature points, curves and surfaces are detected, the remaining surfaces are detected by texture matching and shading changes. Predetermined constraints are applied based on silhouette curves from different views. A different constraint can be applied when one part of the patient is occluded by another object. Further, as the system knows what basic organic shape it is detecting, the basic profile can be applied and adjusted in the process.

In a single camera embodiment, the 3D feature point (e.g. a birth mark) can be detected if the system can identify the same point from two frames. The relative motion from the two frames should be small but detectable. Other features curves and surfaces will be detected correspondingly, but can be tessellated or sampled to generate more feature points. A transformation matrix is calculated between a set of feature points from the first frame to a set of feature points from the second frame. When correlated feature points, curves and surfaces are detected, the rest of the surfaces will be detected by texture matching and shading changes.

Each camera exists in a sphere coordinate system where the sphere origin (0,0,0) is defined as the position of the camera. The system detects theta and phi for each observed object, but not the radius or size of the object. The radius is approximated by detecting the size of known objects and scaling the size of known objects to the object whose size is to be determined. For example, to detect the position of a ball that is 10 cm in radius, the system detects the ball and scales other features based on the known ball size. For human, features that are known in advance include head size and leg length, among others. Surface texture can also be detected, but the light and shade information from different camera views is removed. In either single or multiple camera embodiments, depending on frame rate and picture resolution, certain undetected areas such as holes can exist. For example, if the patient yawns, the patient's mouth can appear as a hole in an image. For 3D modeling purposes, the hole can be filled by blending neighborhood surfaces. The blended surfaces are behind the visible line.

In one embodiment shown in FIG. 2A, each camera is calibrated before 3D detection is done. Pseudo-code for one implementation of a camera calibration process is as follows:

Place a calibration sheet with known dots at a known distance (e.g. 1 meter), and perpendicular to a camera view.

Take snap shot of the sheet, and correlate the position of the dots to the camera image:

$$Dot1(x,y,1) \leftarrow \rightarrow pixel(x,y)$$

Place a different calibration sheet that contains known dots at another different known distance (e.g. 2 meters), and perpendicular to camera view.

Take another snapshot of the sheet, and correlate the position of the dots to the camera image:

$$Dot2(x,y,2) \leftarrow \rightarrow pixel(x,y)$$

Smooth the dots and pixels to minimize digitization errors. By smoothing the map using a global map function, step errors will be eliminated and each pixel will be mapped to a cone space.

For each pixel, draw a line from Dot1$(x,y,z)$ to Dot2$(x, y, z)$ defining a cone center where the camera can view.

One smoothing method is to apply a weighted filter for Dot1 and Dot2. A weight filter can be used. In one example, the following exemplary filter is applied.

1 2 1
2 4 2
1 2 1

Assuming Dot1_Left refers to the value of the dot on the left side of Dot1 and Dot1_Right refers to the value of the dot to the right of Dot1 and Dot1_Upper refers to the dot above Dot1, for example, the resulting smoothed Dot1 value is as follows:

$$\tfrac{1}{16} * (Dot1*4 + Dot1\_Left*2 + Dot1\_Right*2 + Dot1\_Upper*2 + Dot1\_Down*2 + Dot1\_UpperLeft + Dot1\_UpperRight + Dot1\_LowerLeft + Dot1\_LowerRight)$$

Similarly, the resulting smoothed Dot2 value is as follows:

$$\tfrac{1}{16} * (Dot2*4 + Dot2\_Left*2 + Dot2\_Right*2 + Dot2\_Upper*2 + Dot2\_Down*2 + Dot2\_UpperLeft + Dot2\_UpperRight + Dot2\_LowerLeft + Dot2\_LowerRight)$$

In another smoothing method, features from Dot1 sheet are mapped to a sub pixel level and features of Dot2 sheet are mapped to a sub pixel level and smooth them. To illustrate, Dot1 dot center (5, 5, 1) are mapped to pixel (1.05, 2.86), and Dot2 dot center (10, 10, 2) are mapped to pixel (1.15, 2.76). A predetermined correlation function is then applied.

FIG. 2B shows an exemplary calibration sheet having a plurality of dots. In this embodiment, the dots can be circular dots and square dots which are interleaved among each other. The dots should be placed relatively close to each other and each dot size should not be too large, so we can have as many dots as possible in one snapshot. However, the dots should not be placed too close to each other and the dot size should not be too small, so they are not identifiable.

A module 54 monitors patient activity and generates a warning if the patient has fallen. In one implementation, the system detects the speed of center of mass movement. If the center of mass movement is zero for a predetermined period, the patient is either sleeping or unconscious. The system then attempts to signal the patient and receive confirmatory signals indicating that the patient is conscious. If patient does not confirm, then the system generates an alarm. For example, if the patient has fallen, the system would generate an alarm signal that can be sent to friends, relatives or neighbors of the patient. Alternatively, a third party such as a call center can monitor the alarm signal. Besides monitoring for falls, the system performs video analysis of the patient. For example, during a particular day, the system can determine the amount of time for exercise, sleep, and entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the sensor for 13 minutes and don't show up anywhere else in the house, the system infers that patient had taken a bath or a shower. However, if a person falls and remains motionless for a predetermined period, the system would record the event and notify a designated person to get assistance.

Figure 3:
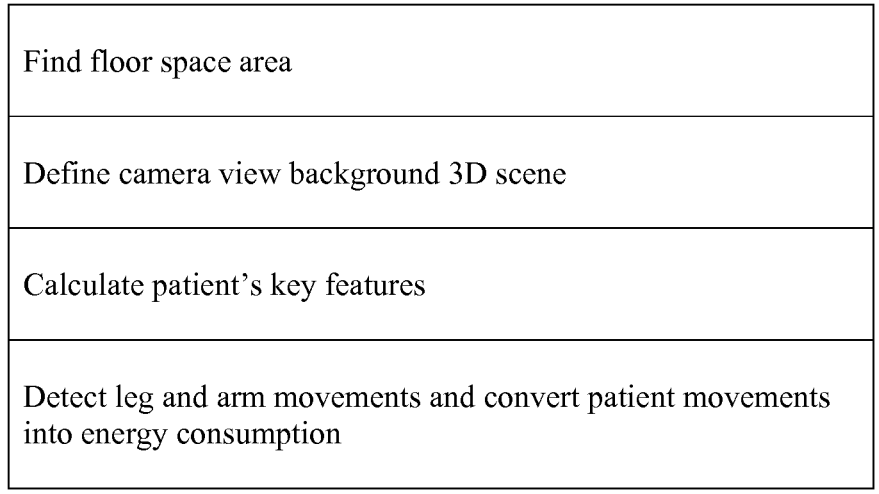
FIG. 3 illustrates a process for detecting patient exercise and activity.

An exercise energy detection process (shown in FIG. 3) performs the following operations:
Find floor space area
Define camera view background 3D scene
Calculate patient's key features
Detect patient movement and convert movement into energy expenditure (such as calories burned).

In one implementation, pseudo-code for determining the floor space area is as follows:
1. Sample the camera view space by M by N, e.g. M=1000, N=500.
2. Calculate all sample points the 3D coordinates in room coordinate system; where Z axis is pointing up. Refer to the 3D detection for how to calculate 3D positions.
3. Find the lowest Z value point (Zmin)
4. Find all points whose Z values are less than Zmin+Zto1; where Zto1 is a user adjustable value, e.g. 2 inches.
5. If rooms have different elevation levels, then excluding the lowest Z floor points, repeat step 2, 3 and 4 while keeping the lowest Z is within Zto12 of previous Z. In this example Zto12=2 feet, which means the floor level difference should be within 2 feet.
6. Detect stairs by finding approximate same flat area but within equal Z differences between them.
7. Optionally, additional information from the user can be used to define floor space more accurately, especially in single camera system where the coordinates are less accurate, e.g.:
   a. Import the CAD file from constructors' blue prints.
   b. Pick regions from the camera space to define the floor, then use software to calculate its room coordinates.
   c. User software to find all flat surfaces, e.g. floors, counter tops, then user pick the ones, which are actually floors and/or stairs.

In the implementation, pseudo-code for determining the camera view background 3D scene is as follows:
1. With the same sample points, calculate x, y coordinates and the Z depth and calculate 3D positions.
2. Determine background scene using one the following methods, among others:
   a. When there is nobody in the room.
   b. Retrieve and update the previous calculated background scene.
   c. Continuous updating every sample point when the furthest Z value was found, that is the background value.

In one implementation, pseudo-code for determining key features of the patient is as follows:
1. Foreground objects can be extracted by comparing each sample point's Z value to the background scene point's Z value, if it is smaller, then it is on the foreground.
2. In normal condition, the feet/shoe can be detected by finding the lowest Z point clouds close the floor in room space, its color will be extracted.
3. In normal condition, the hair/hat can be detected by finding the highest Z point clouds close the floor in room space, its color will be extracted.
4. The rest of the features can be determined by searching from either head or toe. E.g, hat, hair, face, eye, mouth, ear, earring, neck, lipstick, moustache, jacket, limbs, belt, ring, hand, etc.
5. The key dimension of features will be determined by retrieving the historic stored data or recalculated, e.g., head size, mouth width, arm length, leg length, waist, etc.
6. In abnormal conditions, features can be detected by detect individual features then correlated them to different body parts. E.g, if patient's skin is black, we can hardly get a yellow or white face, by detecting eye and nose, we know which part is the face, then we can detect other characteristics.

One embodiment can be used to detect falls—the pseudo-code for the embodiment is as follows:

1. The fall has to be detected in almost real time by tracking movements of key features very quickly. E.g. if patient has black hair/face, track the center of the black blob will know roughly where his head move to.
2. Then the center of mass will be tracked, center of mass is usually around belly button area, so the belt or borderline between upper and lower body closed will be good indications.
3. Patient's fall always coupled with rapid deceleration of center of mass. Software can adjust this threshold based on patient age, height and physical conditions.
4. Then if the fall is accidental and patient has difficult to get up, one or more of following will happen:
   a. Patient will move very slowly to find support object to get up.
   b. Patient will wave hand to camera ask for help. To detect this condition, the patient hand has to be detected first by finding a blob of points with his skin color. Hand motion can be tracked by calculate the motion of the center of the points, if it swings left and right, it means patient is waving to camera.
   c. Patient is unconscious, motionless. To detect this condition, extract the foreground object, calculate its motion vectors, if it is within certain tolerance, it means patient is not moving. In the mean time, test how long it last, if it past a user defined time threshold, it means patient is in great danger.

In one embodiment for fall detection, the system determines a patient fall-down as when the patient's knee, butt or hand is on the floor. The fall action is defined a quick deceleration of center of mass, which is around belly button area. An accidental fall action is defined when the patient falls down with limited movement for a predetermined period.

The system monitors the patients' fall relative to a floor. In one embodiment, the plan of the floor is specified in advance by the patient. Alternatively, the system can automatically determine the floor layout by examining the movement of the patient's feet and estimated the surfaces touched by the feet as the floor.

In one embodiment with in-door positioning, the user can create a facsimile of the floor plan during initialization by walking around the perimeter of each room and recording his/her movement through the in-door positioning system and when complete, press a button to indicate to the system the type of room such as living room, bed room, bath room, among others. Also, the user can calibrate the floor level by sitting down and then standing up (or vice versa) and allowing the accelerometer to sense the floor through the user motion. Periodically, the user can recalibrate the floor plan and/or the floor level.

The system detects a patient exercise activity by detecting a center of mass of an exemplary feature. Thus, the software can monitor the center of one or more objects, for example the head and toe, the patient's belt, the bottom line of the shirt, or the top line of the pants. Movements relative to the center of mass can be converted into exercise motion and energy expenditure can be determined.

In a fall detection warning embodiment, the detection of the patient exercise activity can be adjusted based on two thresholds:

a. Speed of deceleration of the center of mass.
b. The amount of time that the patient lies motionless on the floor after the fall.

If the center of mass movement ceases to move for a predetermined period, the system can generate the warning. In another embodiment, before generating the warning, the system can request the patient to confirm that he or she does not need assistance. The confirmation can be in the form of a button that the user can press to override the warning. Alternatively, the confirmation can be in the form of a single utterance that is then detected by a speech recognizer.

In another embodiment, the confirmatory signal is a patient gesture. The patient can nod his or her head to request help and can shake the head to cancel the help request. Alternatively, the patient can use a plurality of hand gestures to signal to the server 20 the actions that the patient desires.

By adding other detecting mechanism such as sweat detection, the system can know whether patient is uncomfortable or not. Other items that can be monitored include chest movement (frequency and amplitude) and rest length when the patient sits still in one area, among others.

Besides monitoring for exercise activities and falls, the system performs video analysis of the patient. For example, during a particular day, the system can determine the amount of time for exercise, sleep, entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the camera 10 view for a predetermined period and does not show up anywhere else in the house, the system infers that patient had taken a bath or a shower. However, if a person falls and remains motionless for a predetermined period, the system would record the event and notify a designated person to get assistance.

In one embodiment, changes in the patient's skin color can be detected by measuring the current light environment, properly calibrating color space between two photos, and then determining global color change between two states. Thus, when the patient's face turn red, based on the redness, a severity level warning is generated.

In another embodiment, changes in the patient's face are detected by analyzing a texture distortion in the images. If the patient perspires heavily, the texture will show small glisters, make-up smudges, or sweat/tear drippings. Another example is, when long stretched face will be detected as texture distortion. Agony will show certain wrinkle texture patterns, among others.

The system can also utilize high light changes. Thus, when the patient sweats or changes facial appearance, different high light areas are shown, glisters reflect light and pop up geometry generates more high light areas.

A module 62 analyzes facial changes such as facial asymmetries. The change will be detected by superimpose a newly acquired 3D anatomy structure to a historical (normal) 3D anatomy structure to detect face/eye sagging or excess stretch of facial muscles.

In one embodiment, the system determines a set of base 3D shapes, which are a set of shapes which can represent extremes of certain facial effects, e.g. frown, open mouth, smiling, among others. The rest of the 3D face shape can be generated by blending/interpolating these base shapes by applied different weight to each base shapes.

The base 3D shape can be captured using 1) a 3D camera such as cameras from Steinbichler, Genex Technology, Minolta 3D, Olympus 3D or 2) one or more 2D camera with preset camera field of view (FOV) parameters. To make it more accurate, one or more special markers can be placed on patient's face. For example, a known dimension square stick can be placed on the forehead for camera calibration purposes.

Using the above 3D detection method, facial shapes are then extracted. The proper features (e.g. a wrinkle) will be detected and attached to each base shape. These features can be animated or blended by changing the weight of different shape(s). The proper features change can be detected and determine what type of facial shape it will be.

Next, the system super-imposes two 3D facial shapes (historical or normal facial shapes and current facial shapes). By matching features and geometry of changing areas on the face, closely blended shapes can be matched and facial shape change detection can be performed. By overlaying the two shapes, the abnormal facial change such as sagging eyes or mouth can be detected.

The above processes are used to determine paralysis of specific regions of the face or disorders in the peripheral or central nervous system (trigeminal paralysis; CVA, among others). The software also detects eyelid positions for evidence of ptosis (incomplete opening of one or both eyelids) as a sign of innervation problems (CVA; Horner syndrome, for example). The software also checks eye movements for pathological conditions, mainly of neurological origin are reflected in aberrations in eye movement. Pupil reaction is also checked for abnormal reaction of the pupil to light (pupil gets smaller the stronger the light) may indicate various pathological conditions mainly of the nervous system. In patients treated for glaucoma pupillary status and motion pattern may be important to the follow-up of adequate treatment. The software also checks for asymmetry in tongue movement, which is usually indicative of neurological problems. Another check is neck veins: Engorgement of the neck veins may be an indication of heart failure or obstruction of normal blood flow from the head and upper extremities to the heart. The software also analyzes the face, which is usually a mirror of the emotional state of the observed subject. Fear, joy, anger, apathy are only some of the emotions that can be readily detected, facial expressions of emotions are relatively uniform regardless of age, sex, race, etc. This relative uniformity allows for the creation of computer programs attempting to automatically diagnose people's emotional states.

Speech recognition is performed to determine a change in the form of speech (slurred speech, difficulties in the formation of words, for example) may indicated neurological problems, such an observation can also indicate some outward effects of various drugs or toxic agents.

Figure 4:
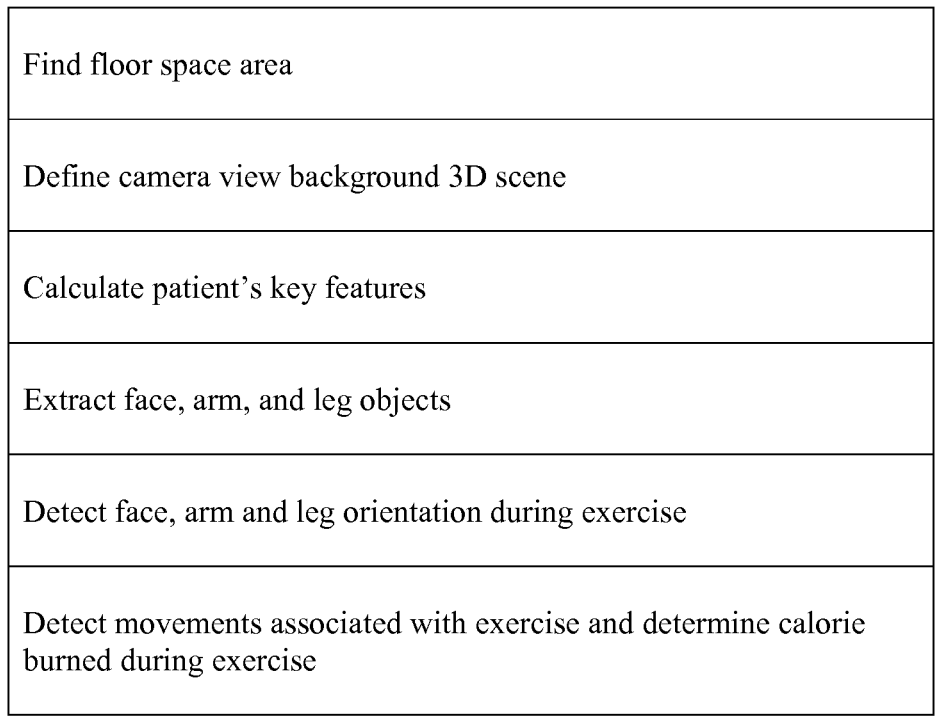
FIG. 4 illustrates a process for detecting patient movements for exercise tracking.

In one embodiment shown in FIG. 4, a facial expression analysis process performs the following operations:
    Find floor space area
    Define camera view background 3D scene
    Calculate patient's key features
    Extract face, arm, and leg objects
    Detect face, arm and leg orientation during exercise
    Detect movements associated with exercise and determine calorie burned during exercise The first three steps are already discussed above. The patient's key features provide information on the location of the face, and once the face area has been determined, other features can be detected by detecting relative position to each other and special characteristics of the features:
    Eye: pupil can be detected by applying Chamfer matching algorithm, by using stock pupil objects.
    Hair: located on the top of the head, using previous stored hair color to locate the hair point clouds.
    Birthmarks, wrinkles and tattoos: pre store all these features then use Chamfer matching to locate them.
    Nose: nose bridge and nose holes usually show special characteristics for detection, sometime depend on the view angle, is side view, special silhouette will be shown.
    Eye browse, Lips and Moustache: All these features have special colors, e.g. red lipstick; and base shape, e.g. patient has no expression with mouth closed. Software will locate these features by color matching, then try to deform the base shape based on expression, and match shape with expression, we can detect objects and expression at the same time.
    Arms and Legs, Teeth, earring, necklace: All these features can be detected by color and style, which will give extra information.

In one implementation, pseudo-code for detecting facial orientation is as follows:
    Detect forehead area
    Use the previously determined features and superimpose them on the base face model to detect a patient face orientation.

Depending on where patient is facing, for a side facing view, silhouette edges will provide unique view information because there is a one to one correspondent between the view and silhouette shape.

Once the patient's face has been aligned to the right view, exemplary pseudo code to detect facial expression is as follows:
    1. Detect shape change. The shape can be match by superimpose different expression shapes to current shape, and judge by minimum discrepancy. E.g. wide mouth open.
    2. Detect occlusion. Sometime the expression can be detected by occlusal of another objects, e.g., teeth show up means mouth is open.
    3. Detect texture map change. The expression can relate to certain texture changes, if patient smile, certain wrinkles patents will show up.
    4. Detect highlight change. The expression can relate to certain high light changes, if patient sweats or cries, different highlight area will show up.

Similar operations can be done to detect arm and leg movements for energy expenditure estimation.

Speech recognition can be performed in one embodiment to determine a change in the form of speech (slurred speech, difficulties in the formation of words, for example) may indicated neurological problems, such an observation can also indicate some outward effects of various drugs or toxic agents.

A module communicates with a third party such as the police department, a security monitoring center, or a call center. The module operates with a POTS telephone and can use a broadband medium such as DSL or cable network if available. The module 80 requires that at least the telephone is available as a lifeline support. In this embodiment, duplex sound transmission is done using the POTS telephone network. The broadband network, if available, is optional for high resolution video and other advanced services transmission.

During operation, the module checks whether broadband network is available. If broadband network is available, the module 80 allows high resolution video, among others, to be broadcasted directly from the server 20 to the third party or indirectly from the server 20 to the remote server 200 to the third party. In parallel, the module 80 allows sound to be transmitted using the telephone circuit. In this manner, high resolution video can be transmitted since sound data is separately sent through the POTS network.

If broadband network is not available, the system relies on the POTS telephone network for transmission of voice and images. In this system, one or more images are compressed for burst transmission, and at the request of the third party or the remote server 200, the telephone's sound system is placed on hold for a brief period to allow transmission of images over the POTS network. In this manner, existing POTS lifeline telephone can be used to monitor patients. The resolution and quantity of images are selectable by the third party. Thus, using only the lifeline as a communication medium, the person monitoring the patient can elect to only listen, to view one high resolution image with duplex telephone voice transmission, to view a few low resolution images, to view a compressed stream of low resolution video with digitized voice, among others.

During installation or while no live person in the scene, each camera will capture its own environment objects and store it as background images, the software then detect the live person in the scene, changes of the live person, so only the portion of live person will be send to the local server, other compression techniques will be applied, e.g. send changing file, balanced video streaming based on change.

The local server will control and schedule how the video/picture will be send, e.g. when the camera is view an empty room, no pictures will be sent, the local server will also determine which camera is at the right view, and request only the corresponding video be sent. The local server will determine which feature it is interested in looking at, e.g. face and request only that portion be sent.

With predetermined background images and local server controlled streaming, the system will enable higher resolution and more camera system by using narrower bandwidth.

Through this module, a police officer, a security agent, or a healthcare agent such as a physician at a remote location can engage, in interactive visual communication with the patient. The patient's health data or audio-visual signal can be remotely accessed. The patient also has access to a video transmission of the third party. Should the patient experience health symptoms requiring intervention and immediate care, the health care practitioner at the central station may summon help from an emergency services provider. The emergency services provider may send an ambulance, fire department personnel, family member, or other emergency personnel to the patient's remote location. The emergency services provider may, perhaps, be an ambulance facility, a police station, the local fire department, or any suitable support facility.

Communication between the patient's remote location and the central station can be initiated by a variety of techniques. One method is by manually or automatically placing a call on the telephone to the patient's home or from the patient's home to the central station.

Alternatively, the system can ask a confirmatory question to the patient through text to speech software. The patient can be orally instructed by the health practitioner to conduct specific physical activities such as specific arm movements, walking, bending, among others. The examination begins during the initial conversation with the monitored subject. Any changes in the spontaneous gestures of the body, arms and hands during speech as well as the fulfillment of nonspecific tasks are important signs of possible pathological events. The monitoring person can instruct the monitored subject to perform a series of simple tasks which can be used for diagnosis of neurological abnormalities. These observations may yield early indicators of the onset of a disease.

A network 100 such as the Internet receives images from the server 20 and passes the data to one or more remote servers 200. The images are transmitted from the server 200 over a secure communication link such as virtual private network (VPN) to the remote server(s) 200.

In one embodiment where cameras are deployed, the server 200 collects data from a plurality of cameras and uses the 3D images technology to determine if the patient needs help. The system can transmit video (live or archived) to the friend, relative, neighbor, or call center for human review. At each viewer site, after a viewer specifies the correct URL to the client browser computer, a connection with the server 200 is established and user identity authenticated using suitable password or other security mechanisms. The server 200 then retrieves the document from its local disk or cache memory storage and transmits the content over the network. In the typical scenario, the user of a Web browser requests that a media stream file be downloaded, such as sending, in particular, the URL of a media redirection file from a Web server. The media redirection file (MRF) is a type of specialized Hypertext Markup Language (HTML) file that contains instructions for how to locate the multimedia file and in what format the multimedia file is in. The Web server returns the MRF file to the user's browser program. The browser program then reads the MRF file to determine the location of the media server containing one or more multimedia content files. The browser then launches the associated media player application program and passes the MRF file to it. The media player reads the MRF file to obtain the information needed to open a connection to a media server, such as a URL, and the required protocol information, depending upon the type of medial content is in the file. The streaming media content file is then routed from the media server down to the user.

In the camera embodiment, the transactions between the server 200 and one of the remote servers 200 are detailed. The server 200 compares one image frame to the next image frame. If no difference exists, the duplicate frame is deleted to minimize storage space. If a difference exists, only the difference information is stored as described in the JPEG standard. This operation effectively compresses video information so that the camera images can be transmitted even at telephone modem speed of 64 k or less. More aggressive compression techniques can be used. For example, patient movements can be clusterized into a group of known motion vectors, and patient movements can be described using a set of vectors. Only the vector data is saved. During view back, each vector is translated into a picture object which is suitably rasterized. The information can also be compressed as motion information.

Next, the server 200 transmits the compressed video to the remote server 200. The server 200 stores and caches the video data so that multiple viewers can view the images at once since the server 200 is connected to a network link such as telephone line modem, cable modem, DSL modem, and ATM transceiver, among others.

In one implementation, the servers 200 use RAID-5 striping and parity techniques to organize data in a fault tolerant and efficient manner. The RAID (Redundant Array of Inexpensive Disks) approach is well described in the literature and has various levels of operation, including RAID-5, and the data organization can achieve data storage in a fault tolerant and load balanced manner. RAID-5 provides that the stored data is spread among three or more disk drives, in a redundant manner, so that even if one of the disk drives fails, the data stored on the drive can be recovered in an efficient and error free manner from the other storage locations. This method also advantageously makes use of each of the disk drives in relatively equal and substantially parallel operations. Accordingly, if one has a six gigabyte cluster volume which spans three disk drives, each disk drive would be responsible for servicing two gigabytes of the cluster volume. Each two gigabyte drive would be comprised of one-third redundant information, to provide the redundant, and thus fault tolerant, operation required for the RAID-5 approach. For additional physical security, the server can be stored in a Fire Safe or other secured box, so there is no chance to erase the recorded data, this is very important for forensic analysis.

The system can also monitor the patient's gait pattern and generate warnings should the patient's gait patterns indicate that the patient is likely to fall. The system will detect patient skeleton structure, stride and frequency; and based on this information to judge whether patient has joint problem, asymmetrical bone structure, among others. The system can store historical gait information, and by overlaying current structure to the historical (normal) gait information, gait changes can be detected. In the camera embodiment, an estimate of the gait pattern is done using the camera. In a camera-less embodiment, the gait can be sensed by providing a sensor on the floor and a sensor near the head and the variance in the two sensor positions are used to estimate gait characteristics.

The system also provides a patient interface 90 to assist the patient in easily accessing information. In one embodiment, the patient interface includes a touch screen; voice-activated text reading; one touch telephone dialing; and video conferencing. The touch screen has large icons that are pre-selected to the patient's needs, such as his or her favorite web sites or application programs. The voice activated text reading allows a user with poor eye-sight to get information from the patient interface 90. Buttons with pre-designated dialing numbers, or video conferencing contact information allow the user to call a friend or a healthcare provider quickly.

In one embodiment, medicine for the patient is tracked using radio frequency identification (RFID) tags. In this embodiment, each drug container is tracked through an RFID tag that is also a drug label. The RF tag is an integrated circuit that is coupled with a mini-antenna to transmit data. The circuit contains memory that stores the identification Code and other pertinent data to be transmitted when the chip is activated or interrogated using radio energy from a reader. A reader consists of an RF antenna, transceiver and a microprocessor. The transceiver sends activation signals to and receives identification data from the tag. The antenna may be enclosed with the reader or located outside the reader as a separate piece. RFID readers communicate directly with the RFID tags and send encrypted usage data over the patient's network to the server 200 and eventually over the Internet 100. The readers can be built directly into the walls or the cabinet doors.

In one embodiment, capacitively coupled RFID tags are used. The capacitive RFID tag includes a silicon microprocessor that can store 96 bits of information, including the pharmaceutical manufacturer, drug name, usage instruction and a 40-bit serial number. A conductive carbon ink acts as the tag's antenna and is applied to a paper substrate through conventional printing means. The silicon chip is attached to printed carbon-ink electrodes on the back of a paper label, creating a low-cost, disposable tag that can be integrated on the drug label. The information stored on the drug labels is written in a Medicine Markup Language (MML), which is based on the eXtensible Markup Language (XML). MML would allow all computers to communicate with any computer system in a similar way that Web servers read Hyper Text Markup Language (HTML), the common language used to create Web pages.

After receiving the medicine container, the patient places the medicine in a medicine cabinet, which is also equipped with a tag reader. This smart cabinet then tracks all medicine stored in it. It can track the medicine taken, how often the medicine is restocked and can let the patient know when a particular medication is about to expire. At this point, the server 200 can order these items automatically. The server 200 also monitors drug compliance, and if the patient does not remove the bottle to dispense medication as prescribed, the server 200 sends a warning to the healthcare provider.

The user's habits can be determined by the system. This is done by tracking location, ambulatory travel vectors and time in a database. Thus, if the user typically sleeps between 10 pm to 6 am, the location would reflect that the user's location maps to the bedroom between 10 pm and 6 am. In one exemplary system, the system builds a schedule of the user's activity as follows:

| Location | Time Start | Time End | Heart Rate |
|---|---|---|---|
| Bed room | 10pm | 6am | 60 - 80 |
| Gym room | 6am | 7am | 90 - 120 |
| Bath room | 7am | 7:30am | 85 - 120 |
| Dining room | 7:30am | 8:45am | 80 - 90 |
| Home Office | 8:45am | 11:30am | 85 - 100 |

The habit tracking is adaptive in that it gradually adjusts to the user's new habits. If there are sudden changes, the system flags these sudden changes for follow up. For instance, if the user spends three hours in the bathroom, the system prompts the third party (such as a call center) to follow up with the patient to make sure he or she does not need help.

In one embodiment, data driven analyzers may be used to track the patient's habits. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient's habits or ambulation patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfilling the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j)(O(t)]$, where the $b(j)(O(t))$ term of the output symbol matrix is the probability of outputting observation $O(t)$, given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability $b(j) O(t)$ corresponds to the probability assigned by the model that the feature frame symbol is $O(t)$. The model arrangement is a matrix $A=[a(i,j)]$ of transition probabilities and a technique of computing $B=b(j) O(t)$, the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The system allows patients to conduct a low-cost, comprehensive, real-time monitoring of their vital parameters such as ambulation and falls. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

The wearable appliance is small, easily worn by the patient during periods of exercise or day-to-day activities, and non-invasively measures blood pressure can be done in a matter of seconds without affecting the patient. An on-board or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

The wearable appliance provides an in-depth, cost-effective mechanism to evaluate a patient's health condition. Certain cardiac conditions can be controlled, and in some cases predicted, before they actually occur. Moreover, data from the patient can be collected and analyzed while the patient participates in their normal, day-to-day activities.

Software programs associated with the Internet-accessible website, secondary software system, and the personal computer analyze the blood pressure, and heart rate, and pulse oximetry values to characterize the patient's cardiac condition. These programs, for example, may provide a report that features statistical analysis of these data to determine averages, data displayed in a graphical format, trends, and comparisons to doctor-recommended values.

When the appliance cannot communicate with the mesh network, the appliance simply stores information in memory and continues to make measurements. The watch component automatically transmits all the stored information (along with a time/date stamp) when it comes in proximity to the wireless mesh network, which then transmits the information through the wireless network.

In one embodiment, the server provides a web services that communicate with third party software through an interface. To generate vital parameters such as blood pressure information for the web services software interface, the patient continuously wears the blood-pressure monitor for a short period of time, e.g. one to two weeks after visiting a medical professional during a typical 'check up' or after signing up for a short-term monitoring program through the website. In this case, the wearable device such as the watch measures mobility through the accelerometer and blood pressure in a near-continuous, periodic manner such as every fifteen minutes. This information is then transmitted over the mesh network to a base station that communicates over the Internet to the server.

To view information sent from the blood-pressure monitor and fall detector on the wearable appliance, the patient or an authorized third party such as family members, emergency personnel, or medical professional accesses a patient user interface hosted on the web server 200 through the Internet 100 from a remote computer system. The patient interface displays vital information such as ambulation, blood pressure and related data measured from a single patient. The system may also include a call center, typically staffed with medical professionals such as doctors, nurses, or nurse practioners, whom access a care-provider interface hosted on the same website on the server 200. The care-provider interface displays vital data from multiple patients.

The wearable appliance has an indoor positioning system and processes these signals to determine a location (e.g., latitude, longitude, and altitude) of the monitor and, presumably, the patient. This location could be plotted on a map by the server, and used to locate a patient during an emergency, e.g. to dispatch an ambulance.

In one embodiment, the web page hosted by the server 200 includes a header field that lists general information about the patient (e.g. name, age, and ID number, general location, and information concerning recent measurements); a table that lists recently measured blood pressure data and suggested (i.e. doctor-recommended) values of these data; and graphs that plot the systolic and diastolic blood pressure data in a time-dependent manner. The header field additionally includes a series of tabs that each link to separate web pages that include, e.g., tables and graphs corresponding to a different data measured by the wearable device such as calorie consumption/dissipation, ambulation pattern, sleeping pattern, heart rate, pulse oximetry, and temperature. The table lists a series of data fields that show running average values of the patient's daily, monthly, and yearly vital parameters. The levels are compared to a series of corresponding 'suggested' values of vital parameters that are extracted from a database associated with the web site. The suggested values depend on, among other things, the patient's age, sex, and weight. The table then calculates the difference between the running average and suggested values to give the patient an idea of how their data compares to that of a healthy patient. The web software interface may also include security measures such as authentication, authorization, encryption, credential presentation, and digital signature resolution. The interface may also be modified to conform to industry-mandated, XML schema definitions, while being 'backwards compatible' with any existing XML schema definitions.

The system provides for self-registration of appliances by the user. Data can be synchronized between the Repository and appliance(s) via the base station 20. The user can preview the readings received from the appliance(s) and reject erroneous readings. The user or treating professional can set up the system to generate alerts against received data, based on pre-defined parameters. The system can determine trends in received data, based on user defined parameters.

Appliance registration is the process by which a patient monitoring appliance is associated with one or more users of the system. This mechanism is also used when provisioning appliances for a user by a third party, such as a clinician (or their respective delegate). In one implementation, the user (or delegate) logs into the portal to select one or more appliances and available for registration. In turn, the base station server 20 broadcasts a query to all nodes in the mesh network to retrieve identification information for the appliance such as manufacturer information, appliance model information, appliance serial number and optionally a hub number (available on hub packaging). The user may register more than one appliance at this point. The system optionally sets up a service subscription for appliance(s) usage. This includes selecting service plans and providing payment information. The appliance(s) are then associated with this user's account and a control file with appliance identification information is synchronized between the server 200 and the base station 20 and each appliance on initialization. In one embodiment, each appliance 8 transmits data to the base station 20 in an XML format for ease of interfacing and is either kept encrypted or in a non-readable format on the base station 20 for security reasons.

The base station 20 frequently collects and synchronizes data from the appliances 8. The base station 20 may use one of various transportation methods to connect to the repository on the server 200 using a PC as conduit or through a connection established using an embedded modem (connected to a phone line), a wireless router (DSL or cable wireless router), a cellular modem, or another network-connected appliance (such as, but not limited to, a web-phone, video-phone, embedded computer, PDA or handheld computer).

In one embodiment, users may set up alerts or reminders that are triggered when one or more reading meet a certain set of conditions, depending on parameters defined by the user. The user chooses the condition that they would like to be alerted to and by providing the parameters (e.g. threshold value for the reading) for alert generation. Each alert may have an interval which may be either the number of data points or a time duration in units such as hours, days, weeks or months. The user chooses the destination where the alert may be sent. This destination may include the user's portal, e-mail, pager, voice-mail or any combination of the above.

Trends are determined by applying mathematical and statistical rules (e.g. moving average and deviation) over a set of reading values. Each rule is configurable by parameters that are either automatically calculated or are set by the user.

The user may give permission to others as needed to read or edit their personal data or receive alerts. The user or clinician could have a list of people that they want to monitor and have it show on their "My Account" page, which serves as a local central monitoring station in one embodiment. Each person may be assigned different access rights which may be more or less than the access rights that the patient has. For example, a doctor or clinician could be allowed to edit data for example to annotate it, while the patient would have read-only privileges for certain pages. An authorized person could set the reminders and alerts parameters with limited access to others. In one embodiment, the base station server 20 serves a web page customized by the user or the user's representative as the monitoring center that third parties such as family, physicians, or caregivers can log in and access information. In another embodiment, the base station 20 communicates with the server 200 at a call center so that the call center provides all services. In yet another embodiment, a hybrid solution where authorized representatives can log in to the base station server 20 access patient information while the call center logs into both the server 200 and the base station server 20 to provide complete care services to the patient.

The server 200 may communicate with a business process outsourcing (BPO) company or a call center to provide central monitoring in an environment where a small number of monitoring agents can cost effectively monitor multiple people 24 hours a day. A call center agent, a clinician or a nursing home manager may monitor a group or a number of users via a summary "dashboard" of their readings data, with ability to drill-down into details for the collected data. A clinician administrator may monitor the data for and otherwise administer a number of users of the system. A summary "dashboard" of readings from all Patients assigned to the Administrator is displayed upon log in to the Portal by the Administrator. Readings may be color coded to visually distinguish normal vs. readings that have generated an alert, along with description of the alert generated. The Administrator may drill down into the details for each Patient to further examine the readings data, view charts etc. in a manner similar to the Patient's own use of the system. The Administrator may also view a summary of all the appliances registered to all assigned Patients, including but not limited to all appliance identification information. The Administrator has access only to information about Patients that have been assigned to the Administrator by a Super Administrator. This allows for segmenting the entire population of monitored Patients amongst multiple Administrators. The Super Administrator may assign, remove and/or reassign Patients amongst a number of Administrators.

In one embodiment, a patient using an Internet-accessible computer and web browser, directs the browser to an appropriate URL and signs up for a service for a short-term (e.g., 1 month) period of time. The company providing the service completes an accompanying financial transaction (e.g. processes a credit card), registers the patient, and ships the patient a wearable appliance for the short period of time. The registration process involves recording the patient's name and contact information, a number associated with the monitor (e.g. a serial number), and setting up a personalized website. The patient then uses the monitor throughout the monitoring period, e.g. while working, sleeping, and exercising. During this time the monitor measures data from the patient and wirelessly transmits it through the channel to a data center. There, the data are analyzed using software running on computer servers to generate a statistical report. The computer servers then automatically send the report to the patient using email, regular mail, or a facsimile machine at different times during the monitoring period. When the monitoring period is expired, the patient ships the wearable appliance back to the monitoring company.

Different web pages may be designed and accessed depending on the end-user. As described above, individual users have access to web pages that only their ambulation and blood pressure data (i.e., the patient interface), while organizations that support a large number of patients (nursing homes or hospitals) have access to web pages that contain data from a group of patients using a care-provider interface. Other interfaces can also be used with the web site, such as interfaces used for: insurance companies, members of a particular company, clinical trials for pharmaceutical companies, and e-commerce purposes. Vital patient data displayed on these web pages, for example, can be sorted and analyzed depending on the patient's medical history, age, sex, medical condition, and geographic location. The web pages also support a wide range of algorithms that can be used to analyze data once they are extracted from the data packets. For example, an instant message or email can be sent out as an 'alert' in response to blood pressure indicating a medical condition that requires immediate attention. Alternatively, the message could be sent out when a data parameter (e.g. systolic blood pressure) exceeds a predetermined value. In some cases, multiple parameters (e.g., fall detection, positioning data, and blood pressure) can be analyzed simultaneously to generate an alert message. In general, an alert message can be sent out after analyzing one or more data parameters using any type of algorithm. These algorithms range from the relatively simple (e.g., comparing blood pressure to a recommended value) to the complex (e.g., predictive medical diagnoses using 'data mining' techniques). In some cases data may be 'fit' using algorithms such as a linear or non-linear least-squares fitting algorithm.

In one embodiment, a physician, other health care practitioner, or emergency personnel is provided with access to patient medical information through the server 200. In one embodiment, if the wearable appliance detects that the patient needs help, or if the patient decides help is needed, the system can call his or her primary care physician. If the patient is unable to access his or her primary care physician (or another practicing physician providing care to the patient) a call from the patient is received, by an answering service or a call center associated with the patient or with the practicing physician. The call center determines whether the patient is exhibiting symptoms of an emergency condition by polling vital patient information generated by the wearable device, and if so, the answering service contacts 911 emergency service or some other emergency service. The call center can review falls information, blood pressure information, and other vital information to determine if the patient is in need of emergency assistance. If it is determined that the patient in not exhibiting symptoms of an emergent condition, the answering service may then determine if the patient is exhibiting symptoms of a non-urgent condition. If the patient is exhibiting symptoms of a non-urgent condition, the answering service will inform the patient that he or she may log into the server 200 for immediate information on treatment of the condition. If the answering service determines that the patient is exhibiting symptoms that are not related to a non-urgent condition, the answering service may refer the patient to an emergency room, a clinic, the practicing physician (when the practicing physician is available) for treatment.

In another embodiment, the wearable appliance permits direct access to the call center when the user pushes a switch or button on the appliance, for instance. In one implementation, telephones and switching systems in call centers are integrated with the home mesh network to provide for, among other things, better routing of telephone calls, faster delivery of telephone calls and associated information, and improved service with regard to client satisfaction through computer-telephony integration (CTI). CTI implementations of various design and purpose are implemented both within individual call-centers and, in some cases, at the telephone network level. For example, processors running CTI software applications may be linked to telephone switches, service control points (SCPs), and network entry points within a public or private telephone network. At the call-center level, CTI-enhanced processors, data servers, transaction servers, and the like, are linked to telephone switches and, in some cases, to similar CTI hardware at the network level, often by a dedicated digital link CTI processors and other hardware within a call-center is commonly referred to as customer premises equipment (CPE). It is the CTI processor and application software is such centers that provides computer enhancement to a call center. In a CTI-enhanced call center, telephones at agent stations are connected to a central telephony switching apparatus, such as an automatic call distributor (ACD) switch or a private branch exchange (PBX). The agent stations may also be equipped with computer terminals such as personal computer/video display unit's (PC/VDU's) so that agents manning such stations may have access to stored data as well as being linked to incoming callers by telephone equipment. Such stations may be interconnected through the PC/VDUs by a local area network (LAN). One or more data or transaction servers may also be connected to the LAN that interconnects agent stations. The LAN is, in turn, typically connected to the CTI processor, which is connected to the call switching apparatus of the call center.

When a call from a patient arrives at a call center, whether or not the call has been pre-processed at an SCP, the telephone number of the calling line and the medical record are made available to the receiving switch at the call center by the network provider. This service is available by most networks as caller-ID information in one of several formats such as Automatic Number Identification (ANI). Typically the number called is also available through a service such as Dialed Number Identification Service (DNIS). If the call center is computer-enhanced (CTI), the phone number of the calling party may be used as a key to access additional medical and/or historical information from a customer information system (CIS) database at a server on the network that connects the agent workstations. In this manner information pertinent to a call may be provided to an agent, often as a screen pop on the agent's PC/VDU.

The call center enables any of a first plurality of physician or health care practitioner terminals to be in audio communication over the network with any of a second plurality of patient wearable appliances. The call center will route the call to a physician or other health care practitioner at a physician or health care practitioner terminal and information related to the patient (such as an electronic medical record) will be received at the physician or health care practitioner terminal via the network. The information may be forwarded via a computer or database in the practicing physician's office or by a computer or database associated with the practicing physician, a health care management system or other health care facility or an insurance provider. The physician or health care practitioner is then permitted to assess the patient, to treat the patient accordingly, and to forward updated information related to the patient (such as examination, treatment and prescription details related to the patient's visit to the patient terminal) to the practicing physician via the network 200.

In one embodiment, the system informs a patient of a practicing physician of the availability of the web services and referring the patient to the web site upon agreement of the patient. A call from the patient is received at a call center. The call center enables physicians to be in audio communication over the network with any patient wearable appliances, and the call is routed to an available physician at one of the physician so that the available physician may carry on a two-way conversation with the patient. The available physician is permitted to make an assessment of the patient and to treat the patient. The system can forward information related to the patient to a health care management system associated with the physician. The health care management system may be a healthcare management organization, a point of service health care system, or a preferred provider organization. The health care practitioner may be a nurse practitioner or an internist.

The available health care practitioner can make an assessment of the patient and to conduct an examination of the patient over the network, including optionally by a visual study of the patient. The system can make an assessment in accordance with a protocol. The assessment can be made in accordance with a protocol stored in a database and/or making an assessment in accordance with the protocol may include displaying in real time a relevant segment of the protocol to the available physician. Similarly, permitting the physician to prescribe a treatment may include permitting the physician to refer the patient to a third party for treatment and/or referring the patient to a third party for treatment may include referring the patient to one or more of a primary care physician, specialist, hospital, emergency room, ambulance service or clinic. Referring the patient to a third party may additionally include communicating with the third party via an electronic link included in a relevant segment of a protocol stored in a protocol database resident on a digital storage medium and the electronic link may be a hypertext link. When a treatment is being prescribed by a physician, the system can communicate a prescription over the network to a pharmacy and/or communicating the prescription over the network to the pharmacy may include communicating to the pharmacy instructions to be given to the patient pertaining to the treatment of the patient. Communicating the prescription over the network to the pharmacy may also include communicating the prescription to the pharmacy via a hypertext link included in a relevant segment of a protocol stored in a database resident on a digital storage medium. In accordance with another related embodiment, permitting the physician to conduct the examination may be accomplished under conditions such that the examination is conducted without medical instruments at the patient terminal where the patient is located.

In another embodiment, a system for delivering medical examination, diagnosis, and treatment services from a physician to a patient over a network includes a first plurality of health care practitioners at a plurality of terminals, each of the first plurality of health care practitioner terminals including a display device that shows information collected by the wearable appliances and a second plurality of patient terminals or wearable appliances in audiovisual communication over a network with any of the first plurality of health care practitioner terminals. A call center is in communication with the patient wearable appliances and the health care practitioner terminals, the call center routing a call from a patient at one of the patient terminals to an available health care practitioner at one of the health care practitioner terminals, so that the available health care practitioner may carry on a two-way conversation with the patient. A protocol database resident on a digital storage medium is accessible to each of the health care practitioner terminals. The protocol database contains a plurality of protocol segments such that a relevant segment of the protocol may be displayed in real time on the display device of the health care practitioner terminal of the available health care practitioner for use by the available health care practitioner in making an assessment of the patient. The relevant segment of the protocol displayed in real time on the display device of the health care practitioner terminal may include an electronic link that establishes communication between the available health care practitioner and a third party and the third party may be one or more of a primary care physician, specialist, hospital, emergency room, ambulance service, clinic or pharmacy.

In accordance with other related embodiment, the patient wearable appliance may include establish a direct connection to the call center by pushing a button on the appliance. Further, the protocol database may be resident on a server that is in communication with each of the health care practitioner terminals and each of the health care practitioner terminals may include a local storage device and the protocol database is replicated on the local storage device of one or more of the physician terminals.

In another embodiment, a system for delivering medical examination, diagnosis, and treatment services from a physician to a patient over a network includes a first plurality of health care practitioner terminals, each of the first plurality of health care practitioner terminals including a display device and a second plurality of patient terminals in audiovisual communication over a network with any of the first plurality of health care practitioner terminals. Each of the second plurality of patient terminals includes a camera having pan, tilt and zoom modes, such modes being controlled from the first plurality of health care practitioner terminals. A call center is in communication with the patient terminals and the health care practitioner terminals and the call center routes a call from a patient at one of the patient terminals to an available health care practitioner at one of the health care practitioner terminals, so that the available health care practitioner may carry on a two-way conversation with the patient and visually observe the patient.

In one embodiment, the information is store in a secure environment, with security levels equal to those of online banking, social security number input, and other confidential information. Conforming to Health Insurance Portability and Accountability Act (HIPAA) requirements, the system creates audit trails, requires logins and passwords, and provides data encryption to ensure the patient information is private and secure. The HIPAA privacy regulations ensure a national floor of privacy protections for patients by limiting the ways that health plans, pharmacies, hospitals and other covered entities can use patients' personal medical information. The regulations protect medical records and other individually identifiable health information, whether it is on paper, in computers or communicated orally.

Due to its awareness of the patient's position, the server 200 can optionally control a mobility assistance device such as a smart cane or robot. The robotic smart cane sends video from its camera to the server 20, which in turn coordinates the position of the robot, as determined by the cameras 10 mounted in the home as well as the robot camera. The robot position, as determined by the server 20, is then transmitted to the robot for navigation. The robot has a frame with an extended handle. The handle includes handle sensors mounted thereon to detect the force places on each handle to receive as input the movement desired by the patient. In one embodiment, the robot has a control navigation system that accepts patient command as well as robot self-guidance command. The mobility is a result of give-and-take between the patient's self-propulsion and the walker's automated reactions. Thus, when the patient moves the handle to the right, the robot determines that the patient is interested in turning and actuates the drive systems appropriately. However, if the patient is turning into an obstacle, as determined by the cameras and the server 20, the drive system provides gentle resistance that tells the patient of an impending collision.

If, for example, a patient does not see a coffee table ahead, the walker will detect it, override the patient's steering to avoid it, and thereby prevent a possible fall. Onboard software processes the data from 180 degrees of approaching terrain and steers the front wheel toward openings and away from obstacles.

The control module executes software that enables the robot to move around its environment safely. The software performs localization, mapping, path planning and obstacle avoidance. In one embodiment, images from a plurality of wall-mounted cameras 10 are transmitted to the server 20. The server 20 collects images of the robot and triangulates the robot position by cross-referencing the images. The information is then correlated with the image from the robot-mounted camera and optical encoders that count the wheel rotations to calculate traveled distance for range measurement. In this process, a visual map of unique "landmarks" created as the robot moves along its path is annotated with the robot's position to indicate the position estimate of the landmark. The current image, seen from the robot, is compared with the images in the database to find matching landmarks. Such matches are used to update the position of the robot according to the relative position of the matching landmark. By repeatedly updating the position of landmarks based on new data, the software incrementally improves the map by calculating more accurate estimates for the position of the landmarks. An improved map results in more accurate robot position estimates. Better position estimates contribute to better estimates for the landmark positions and so on. If the environment changes so much that the robot no longer recognizes previous landmarks, the robot automatically updates the map with new landmarks. Outdated landmarks that are no longer recognized can easily be deleted from the map by simply determining if they were seen or matched when expected.

Using the obstacle avoidance algorithm, the robot generates corrective movements to avoid obstacles not represented in the path planner such as open/closed doors, furniture, people, and more. The robot rapidly detects obstacles using its sensors and controls its speed and heading to avoid obstacles.

The hazard avoidance mechanisms provide a reflexive response to hazardous situations to insure the robot's safety and guarantee that it does not damage itself or the environment. Mechanisms for hazard avoidance include collision detection using not one but a complementary set of sensors and techniques. For instance, collision avoidance can be provided using contact sensing, motor load sensing, and vision. The combination of multiple sources for collision detection guarantees safe collision avoidance. Collision detection provides a last resort for negotiating obstacles in case obstacle avoidance fails to do so in the first place, which can be caused by moving objects or software and hardware failures.

If the walker is in motion (as determined by the wheel encoder), the force applied to the brake pads is inversely proportional to the distance to obstacles. If the walker is stopped, the brakes should be fully applied to provide a stable base on which the patient can rest. When the walker is stopped and the patient wishes to move again, the brakes should come off slowly to prevent the walker from lurching forward The walker should mostly follow the patient's commands, as this is crucial for patient acceptance. For the safety braking and the safety braking and steering control systems, the control system only influences the motion when obstacles or cliffs are near the patient. In other words, the walker is, typically, fully patient controlled. For all other situations, the control system submits to the patient's desire. This does not mean that the control system shuts down, or does not provide the usual safety features. In fact, all of the control systems fall back on their emergency braking to keep the patient safe. When the control system has had to brake to avoid an obstacle or has given up trying to lead the patient on a particular path, the patient must disengage the brakes (via a pushbutton) or re-engage the path following (again via a pushbutton) to regain control or allow collaboration again. This lets the patient select the walker's mode manually when they disagree with the control system's choices.

FIG. 5 shows an exemplary process to monitor patient. First, the process sets up mesh network appliances (1000). Next, the process determines patient position using in-door positioning system (1002). The process then determines patient movement using accelerometer output (1004). Sharp accelerations may be used to indicate fall. Further, the z axis accelerometer changes can indicate the height of the appliance from the floor and if the height is near zero, the system infers that the patient had fallen. The system can also determine vital parameter including patient heart rate (1006). The system determines if patient needs assistance based on in-door position, fall detection and vital parameter (1008). If a fall is suspected, the system confirms the fall by communicating with the patient prior to calling a third party such as the patient's physician, nurse, family member, 911, 511, 411, or a paid call center to get assistance for the patient (1010). If confirmed or if the patient is non-responsive, the system contacts the third party and sends voice over mesh network to appliance on the patient to allow one or more third parties to talk with the patient (1012). If needed, the system calls and/or conferences emergency personnel into the call (1014).

In one embodiment, if the patient is outside of the mesh network range such as when the user is traveling away from his/her home, the system continuously records information into memory until the home mesh network is reached or until the monitoring appliance reaches an interne access point. While the wearable appliance is outside of the mesh network range, the device searches for a cell phone with an expansion card plugged into a cell phone expansion slot such as the SDIO slot. If the wearable appliance detects a cell phone that is mesh network compatible, the wearable appliance communicates with the cell phone and provides information to the server 200 using the cellular connection. In one embodiment, a Zigbee SDIO card from C-guys, Inc., enables device-to-device communications for PDAs and smart phones. C-guys' ZigBee SDIO card includes the company's CG-100 SDIO application interface controller, which is designed to convert an application signal to an SD signal (or vice versa). The ZigBee card can provide signal ranges of up to 10 m in the 2.4 GHz band and data rates of up to 200 kbps. The card has peer-to-peer communications mode and supports direct application to PDAs or any SD supported hand-held cell phones. In this embodiment, the PDA or cell phone can provide a GPS position information instead of the indoor position information generated by the mesh network appliances 8. The cell phone GPS position information, accelerometer information and vital information such as heart rate information is transmitted using the cellular channel to the server 200 for processing as is normal. In another embodiment where the phone works through WiFi (802.11) or WiMAX (802.16) or ultra-wideband protocol instead of the cellular protocol, the wearable appliance can communicate over these protocols using a suitable mesh network interface to the phone. In instances where the wearable appliance is outside of its home base and a dangerous condition such as a fall is detected, the wearable appliance can initiate a distress call to the authorized third party using cellular, WiFi, WiMAX, or UWB protocols as is available.

FIG. 6A shows a portable embodiment of the present invention where the voice recognizer is housed in a wrist-watch. As shown in FIG. 6, the device includes a wrist-watch sized case 1380 supported on a wrist band 1374. The case 1380 may be of a number of variations of shape but can be conveniently made a rectangular, approaching a box-like configuration. The wrist-band 1374 can be an expansion band or a wristwatch strap of plastic, leather or woven material. The processor or CPU of the wearable appliance is connected to a radio frequency (RF) transmitter/receiver (such as a Bluetooth device, a Zigbee device, a WiFi device, a WiMAX device, or an 802.X transceiver, among others.

In one embodiment, the back of the device is a conductive metal electrode 1381 that in conjunction with a second electrode 1383 mounted on the wrist band 1374, enables differential EKG or ECG to be measured. The electrical signal derived from the electrodes is typically 1 mV peak-peak. In one embodiment where only one electrode 1381 or 1383 is available, an amplification of about 1000 is necessary to render this signal usable for heart rate detection. In the embodiment with electrodes 1381 and 1383 available, a differential amplifier is used to take advantage of the identical common mode signals from the EKG contact points, the common mode noise is automatically cancelled out using a matched differential amplifier. In one embodiment, the differential amplifier is a Texas Instruments INA321 instrumentation amplifier that has matched and balanced integrated gain resistors. This device is specified to operate with a minimum of 2.7V single rail power supply. The INA321 provides a fixed amplification of 5× for the EKG signal. With its CMRR specification of 94 dB extended up to 3 KHz the INA321 rejects the common mode noise signals including the line frequency and its harmonics. The quiescent current of the INA321 is 40 mA and the shut down mode current is less than 1 mA. The amplified EKG signal is internally fed to the on chip analog to digital converter. The ADC samples the EKG signal with a sampling frequency of 512 Hz. Precise sampling period is achieved by triggering the ADC conversions with a timer that is clocked from a 32.768 kHz low frequency crystal oscillator. The sampled EKG waveform contains some amount of super imposed line frequency content. This line frequency noise is removed by digitally filtering the samples. In one implementation, a 17-tap low pass FIR filter with pass band upper frequency of 6 Hz and stop band lower frequency of 30 Hz is implemented in this application. The filter coefficients are scaled to compensate the filter attenuation and provide additional gain for the EKG signal at the filter output. This adds up to a total amplification factor of greater than 1000× for the EKG signal.

The wrist band 1374 can also contain other electrical devices such as ultrasound transducer, optical transducer or electromagnetic sensors, among others. In one embodiment, the transducer is an ultrasonic transducer that generates and transmits an acoustic wave upon command from the CPU during one period and listens to the echo returns during a subsequent period. In use, the transmitted bursts of sonic energy are scattered by red blood cells flowing through the subject's radial artery, and a portion of the scattered energy is directed back toward the ultrasonic transducer 84. The time required for the return energy to reach the ultrasonic transducer varies according to the speed of sound in the tissue and according to the depth of the artery. Typical transit times are in the range of 6 to 7 microseconds. The ultrasonic transducer is used to receive the reflected ultrasound energy during the dead times between the successive transmitted bursts. The frequency of the ultrasonic transducer's transmit signal will differ from that of the return signal, because the scattering red blood cells within the radial artery are moving. Thus, the return signal, effectively, is frequency modulated by the blood flow velocity.

A driving and receiving circuit generates electrical pulses which, when applied to the transducer, produce acoustic energy having a frequency on the order of 8 MHz, a pulse width or duration of approximately 8 microseconds, and a pulse repetition interval (PRI) of approximately 16 µs, although other values of frequency, pulse width, and PRI may be used. In one embodiment, the transducer 84 emits an 8 microsecond pulse, which is followed by an 8 microsecond "listen" period, every 16 microseconds. The echoes from these pulses are received by the ultrasonic transducer 84 during the listen period. The ultrasonic transducer can be a ceramic piezoelectric device of the type well known in the art, although other types may be substituted.

An analog signal representative of the Doppler frequency of the echo is received by the transducer and converted to a digital representation by the ADC, and supplied to the CPU for signal processing. Within the CPU, the digitized Doppler frequency is scaled to compute the blood flow velocity within the artery based on the Doppler frequency. Based on the real time the blood flow velocity, the CPU applies the vital model to the corresponding blood flow velocity to produce the estimated blood pressure value.

Prior to operation, calibration is done using a calibration device and the monitoring device to simultaneously collect blood pressure values (systolic, diastolic pressures) and a corresponding blood flow velocity generated by the monitoring device. The calibration device is attached to the base station and measures systolic and diastolic blood pressure using a cuff-based blood pressure monitoring device that includes a motor-controlled pump and data-processing electronics. While the cuff-based blood pressure monitoring device collects patient data, the transducer collects patient data in parallel and through the watch's radio transmitter, blood flow velocity is sent to the base station for generating a computer model that converts the blood flow velocity information into systolic and diastolic blood pressure values and this information is sent wirelessly from the base station to the watch for display and to a remote server if needed. This process is repeated at a later time (e.g., 15 minutes later) to collect a second set of calibration parameters. In one embodiment, the computer model fits the blood flow velocity to the systolic/diastolic values. In another embodiment, the computer trains a neural network or HMM to recognize the systolic and diastolic blood pressure values.

After the computer model has been generated, the system is ready for real-time blood pressure monitoring. In an acoustic embodiment, the transducer directs ultrasound at the patient's artery and subsequently listens to the echoes therefrom. The echoes are used to determine blood flow, which is fed to the computer model to generate the systolic and diastolic pressure values as well as heart rate value. The CPU's output signal is then converted to a form useful to the user such as a digital or analog display, computer data file, or audible indicator. The output signal can drive a speaker to enable an operator to hear a representation of the Doppler signals and thereby to determine when the transducer is located approximately over the radial artery. The output signal can also be wirelessly sent to a base station for subsequent analysis by a physician, nurse, caregiver, or treating professional. The output signal can also be analyzed for medical attention and medical treatment.

It is noted that while the above embodiment utilizes a preselected pulse duration of 8 microseconds and pulse repetition interval of 16 microseconds, other acoustic sampling techniques may be used in conjunction with the invention. For example, in a second embodiment of the ultrasonic driver and receiver circuit (not shown), the acoustic pulses are range-gated with a more complex implementation of the gate logic. As is well known in the signal processing arts, range-gating is a technique by which the pulse-to-pulse interval is varied based on the receipt of range information from earlier emitted and reflected pulses. Using this technique, the system may be "tuned" to receive echoes falling within a specific temporal window which is chosen based on the range of the echo-producing entity in relation to the acoustic source. The delay time before the gate is turned on determines the depth of the sample volume. The amount of time the gate is activated establishes the axial length of the sample volume. Thus, as the acoustic source (in this case the ultrasonic transducer 84) is tuned to the echo-producing entity (red blood cells, or arterial walls), the pulse repetition interval is shortened such that the system may obtain more samples per unit time, thereby increasing its resolution. It will be recognized that other acoustic processing techniques may also be used, all of which are considered to be equivalent.

In one optical embodiment, the transducer can be an optical transducer. The optical transducer can be a light source and a photo-detector embedded in the wrist band portions 1374. The light source can be light-emitting diodes that generate red ($\lambda \sim 630$ nm) and infrared ($\lambda \cdot 900$ nm) radiation, for example. The light source and the photo-detector are slidably adjustable and can be moved along the wrist band to optimize beam transmission and pick up. As the heart pumps blood through the patient's finger, blood cells absorb and transmit varying amounts of the red and infrared radiation depending on how much oxygen binds to the cells' hemoglobin. The photo-detector detects transmission at the predetermined wavelengths, for example red and infrared wavelengths, and provides the detected transmission to a pulse-oximetry circuit embedded within the wrist-watch. The output of the pulse-oximetry circuit is digitized into a time-dependent optical waveform, which is then sent back to the pulse-oximetry circuit and analyzed to determine the user's vital signs.

In the electromagnetic sensor embodiment, the wrist band 1374 is a flexible plastic material incorporated with a flexible magnet. The magnet provides a magnetic field, and one or more electrodes similar to electrode 1383 are positioned on the wrist band to measure voltage drops which are proportional to the blood velocity. The electromagnetic embodiment may be mounted on the upper arm of the patient, on the ankle or on the neck where peripheral blood vessels pass through and their blood velocity may be measured with minimal interruptions. The flexible magnet produces a pseudo-uniform (non-gradient) magnetic field. The magnetic field can be normal to the blood flow direction when wrist band 1374 is mounted on the user's wrist or may be a rotative pseudo-uniform magnetic field so that the magnetic field is in a transversal direction in respect to the blood flow direction. The electrode output signals are processed to obtain a differential measurement enhancing the signal to noise ratio. The flow information is derived based on the periodicity of the signals. The decoded signal is filtered over several periods and then analyzed for changes used to estimate artery and vein blood flow. Systemic stroke volume and cardiac output may be calculated from the peripheral SV index value.

The wrist-band 1374 further contains an antenna 1376 for transmitting or receiving radio frequency signals. The wrist-band 1374 and the antenna 1376 inside the band are mechanically coupled to the top and bottom sides of the wrist-watch housing 1380. Further, the antenna 1376 is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing 1380 contains the processor and associated peripherals to provide the human-machine interface. A display 1382 is located on the front section of the housing 1380. A speaker 1384, a microphone 1388, and a plurality of push-button switches 1386 and 1390 are also located on the front section of housing 1380.

The electronic circuitry housed in the watch case 1380 detects adverse conditions such as falls or seizures. In one implementation, the circuitry can recognize speech, namely utterances of spoken words by the user, and converting the utterances into digital signals. The circuitry for detecting and processing speech to be sent from the wristwatch to the base station 20 over the mesh network includes a central processing unit (CPU) connected to a ROM/RAM memory via a bus. The CPU is a preferably low power 16-bit or 32-bit microprocessor and the memory is preferably a high density, low-power RAM. The CPU is coupled via the bus to processor wake-up logic, one or more accelerometers to detect sudden movement in a patient, an ADC 102 which receives speech input from the microphone. The ADC converts the analog signal produced by the microphone into a sequence of digital values representing the amplitude of the signal produced by the microphone at a sequence of evenly spaced times. The CPU is also coupled to a digital to analog (D/A) converter, which drives the speaker to communicate with the user. Speech signals from the microphone are first amplified, pass through an antialiasing filter before being sampled. The front-end processing includes an amplifier, a bandpass filter to avoid antialiasing, and an analog-to-digital (A/D) converter or a CODEC. To minimize space, the ADC, the DAC and the interface for wireless transceiver and switches may be integrated into one integrated circuit to save space. In one embodiment, the wrist watch acts as a walkie-talkie so that voice is received over the mesh network by the base station 20 and then delivered to a call center over the POTS or PSTN network. In another embodiment, voice is provided to the call center using the Internet through suitable VOIP techniques. In one embodiment, speech recognition such as a speech recognizer is discussed in U.S. Pat. No. 6,070,140 by the inventor of the instant invention, the content of which is incorporated by reference.

Figure 6B:
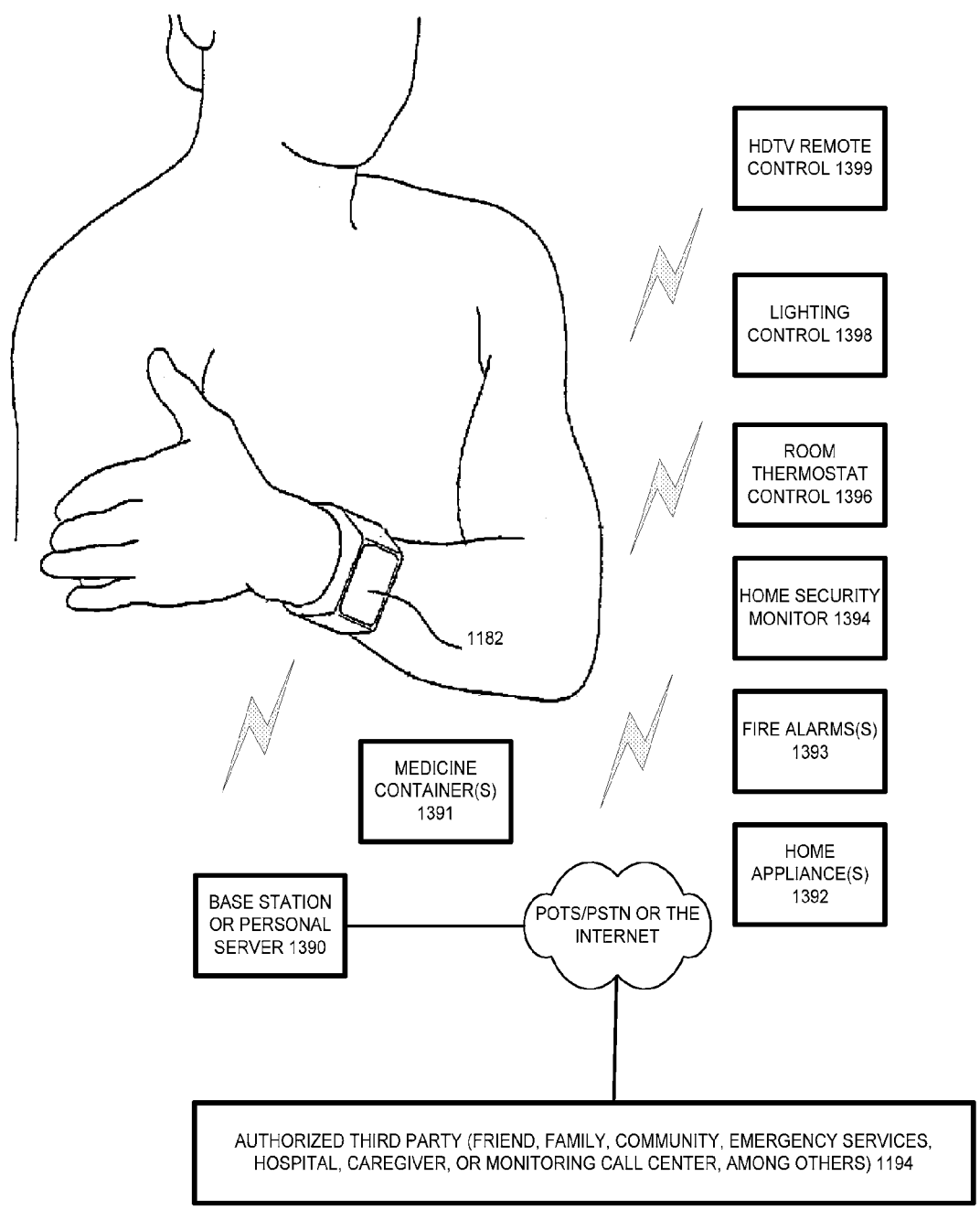
FIG. 6B shows an exemplary mesh network working with the wearable appliance of FIG. 6A.

FIG. 6B shows an exemplary mesh network working with the wearable appliance of FIG. 6A. Data collected and communicated on the display 1382 of the watch as well as voice is transmitted to a base station 1390 for communicating over a network to an authorized party 1394. The watch and the base station is part of a mesh network that may communicate with a medicine cabinet to detect opening or to each medicine container 1391 to detect medication compliance. Other devices include mesh network thermometers, scales, or exercise devices. The mesh network also includes a plurality of home/room appliances 1392-1399. The ability to transmit voice is useful in the case the patient has fallen down and cannot walk to the base station 1390 to request help. Hence, in one embodiment, the watch captures voice from the user and transmits the voice over the Zigbee mesh network to the base station 1390. The base station 1390 in turn dials out to an authorized third party to allow voice communication and at the same time transmits the collected patient vital parameter data and identifying information so that help can be dispatched quickly, efficiently and error-free. In one embodiment, the base station 1390 is a POTS telephone base station connected to the wired phone network. In a second embodiment, the base station 1390 can be a cellular telephone connected to a cellular network for voice and data transmission. In a third embodiment, the base station 1390 can be a WiMAX or 802.16 standard base station that can communicate VOIP and data over a wide area network. Alternatively, the base station can communicate over POTS and a wireless network such as cellular or WiMAX or both.

In one embodiment, the processor and transceiver on the watch and the base station conform to the Zigbee protocol. ZigBee is a cost-effective, standards-based wireless networking solution that supports low data-rates, low-power consumption, security, and reliability. Single chip Zigbee controllers with wireless transceivers built-in include the Chipcon/Ember CC2420: Single-chip 802.15.4 radio transceiver and the FreeScale single chip Zigbee and microcontroller. In various embodiments, the processor communicates with a Z axis accelerometer measures the patient's up and down motion and/or an X and Y axis accelerometer measures the patient's forward and side movements. In one embodiment, EKG and/or blood pressure parameters can be captured by the processor. The controllers upload the captured data when the memory is full or while in wireless contact with other Zigbee nodes.

The wristwatch device can also be used to control home automation. The user can have flexible management of lighting, heating and cooling systems from anywhere in the home. The watch automates control of multiple home systems to improve conservation, convenience and safety. The watch can capture highly detailed electric, water and gas utility usage data and embed intelligence to optimize consumption of natural resources. The system is convenient in that it can be installed, upgraded and networked without wires. The patient can receive automatic notification upon detection of unusual events in his or her home. For example, if smoke or carbon monoxide detectors detect a problem, the wrist-watch can buzz or vibrate to alert the user and the central hub triggers selected lights to illuminate the safest exit route.

In another embodiment, the watch serves a key fob allowing the user to wirelessly unlock doors controlled by Zigbee wireless receiver. In this embodiment, when the user is within range, the door Zigbee transceiver receives a request to unlock the door, and the Zigbee transceiver on the door transmits an authentication request using suitable security mechanism. Upon entry, the Zigbee doorlock device sends access signals to the lighting, air-conditioning and entertainment systems, among others. The lights and temperature are automatically set to pre-programmed preferences when the user's presence is detected.

Although Zigbee is mentioned as an exemplary protocol, other protocols such as UWB, Bluetooth, WiFi and WiMAX can be used as well.

While the foregoing addresses the needs of the elderly, the system can assist infants as well. Much attention has been given to ways to reduce a risk of dying from Sudden Infant Death Syndrome (SIDS), an affliction which threatens infants who have died in their sleep for heretofore unknown reasons. Many different explanations for this syndrome and ways to prevent the syndrome are found in the literature. It is thought that infants which sleep on their backs may be at risk of death because of the danger of formula regurgitation and liquid aspiration into the lungs. It has been thought that infants of six (6) months or less do not have the motor skills or body muscular development to regulate movements responsive to correcting breathing problems that may occur during sleep.

In an exemplary system to detect and minimize SIDS problem in an infant patient, a diaper pad is used to hold an array of integrated sensors and the pad can be placed over a diaper, clothing, or blanket. The integrated sensors can provide data for measuring position, temperature, sound, vibration, movement, and optionally other physical properties through additional sensors. Each pad can have sensors that provide one or more of the above data. The sensors can be added or removed as necessary depending on the type of data being collected.

The sensor should be water proof and disposable. The sensor can be switch on/off locally or remotely. The sensor can be removable or clip on easily. The sensor can store or beam out information for analysis purpose, e.g. store body temperature every 5 seconds. The sensor can be turn-on for other purposed, e.g. diaper wet, it will beep and allow a baby care provider to take care of the business in time. The array of sensors can be self selective, e.g., when one sensor can detect strong heart beat, it will turn off others to do so.

The sensor can be used for drug delivery system, e.g. when patient has abdomen pain, soothing drug can be applied, based on the level of pain the sensor detects, different dose of drugs will be applied.

The array of sensors may allow the selection and analysis of zones of sensors in the areas of interest such as the abdomen area. Each sensor array has a low spatial resolution: approximately 10 cm between each sensor. In addition to lower cost due to the low number of sensors, it is also possible to modify the data collection rate from certain sensors that are providing high-quality data. Other sensors may include those worn on the body, such as in watch bands, finger rings, or adhesive sensors, but telemetry, not wires, would be used to communicate with the controller.

The sensor can be passive device such as a reader, which mounted near the crib can active it from time to time. In any emergency situation, the sensor automatically signals a different state which the reader can detect.

The sensor can be active and powered by body motion or body heat. The sensor can detect low battery situation and warn the user to provide a replacement battery.

In one embodiment, a plurality of sensors attached to the infant collects the vital parameters. For example, the sensors can be attached to the infant's clothing (shirt or pant), diaper, undergarment or bed sheet, bed linen, or bed spread.

The patient may wear one or more sensors, for example devices for sensing ECG, EKG, blood pressure, sugar level, weight, temperature and pressure, among others. In one embodiment, an optical temperature sensor can be used. In another embodiment, a temperature thermistor can be used to sense patient temperature. In another embodiment, a fat scale sensor can be used to detect the patient's fat content. In yet another embodiment, a pressure sensor such as a MEMS sensor can be used to sense pressure on the patient.

In one embodiment, the sensors are mounted on the patient's wrist (such as a wristwatch sensor) and other convenient anatomical locations. Exemplary sensors include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors can individually transmit data to the server 20 using wired or wireless transmission. Alternatively, all sensors can be fed through a common bus into a single transceiver for wired or wireless transmission. The transmission can be done using a magnetic medium such as a floppy disk or a flash memory card, or can be done using infrared or radio network link, among others.

In one embodiment, the sensors for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The heartbeat detector can be one of: EKG detector, ECG detector, optical detector, ultrasonic detector, or microphone/digital stethoscope for picking up heart sound. In one embodiment, one EKG/ECG contact point is provided on the back of the wrist watch case and one or more EKG/ECG contact points are provided on the surface of the watch so that when a user's finger or skin touches the contact points, an electrical signal indicative of heartbeat activity is generated. An electrocardiogram (ECG) or EKG is a graphic tracing of the voltage generated by the cardiac or heart muscle during a heartbeat. It provides very accurate evaluation of the performance of the heart. The heart generates an electrochemical impulse that spreads out in the heart in such a fashion as to cause the cells to contract and relax in a timely order and thus give the heart a pumping characteristic. This sequence is initiated by a group of nerve cells called the sinoatrial (SA) node resulting in a polarization and depolarization of the cells of the heart. Because this action is electrical in nature and because the body is conductive with its fluid content, this electrochemical action can be measured at the surface of the body. An actual voltage potential of approximately 1 mV develops between various body points. This can be measured by placing electrode contacts on the body. The four extremities and the chest wall have become standard sites for applying the electrodes. Standardizing electrocardiograms makes it possible to compare them as taken from person to person and from time to time from the same person. The normal electrocardiogram shows typical upward and downward deflections that reflect the alternate contraction of the atria (the two upper chambers) and of the ventricles (the two lower chambers) of the heart. The voltages produced represent pressures exerted by the heart muscles in one pumping cycle. The first upward deflection, P, is due to atria contraction and is known as the atrial complex. The other deflections, Q, R, S, and T, are all due to the action of the ventricles and are known as the ventricular complexes. Any deviation from the norm in a particular electrocardiogram is indicative of a possible heart disorder.

The CPU measures the time duration between the sequential pulses and converts each such measurement into a corresponding timing measurement indicative of heart rate. The CPU also processes a predetermined number of most recently occurring timing measurements in a prescribed fashion, to produce an estimate of heartbeat rate for display on a display device on the watch and/or for transmission over the wireless network. This estimate is updated with the occurrence of each successive pulse.

In one embodiment, the CPU produces the estimate of heartbeat rate by first averaging a plurality of measurements, then adjusting the particular one of the measurements that differs most from the average to be equal to that average, and finally computing an adjusted average based on the adjusted set of measurements. The process may repeat the foregoing operations a number of times so that the estimate of heartbeat rate is substantially unaffected by the occurrence of heartbeat artifacts.

In one EKG or ECG detector, the heartbeat detection circuitry includes a differential amplifier for amplifying the signal transmitted from the EKG/ECG electrodes and for converting it into single-ended form, and a bandpass filter and a 60 Hz notch filter for removing background noise. The CPU measures the time durations between the successive pulses and estimates the heartbeat rate. The time durations between the successive pulses of the pulse sequence signal provides an estimate of heartbeat rate. Each time duration measurement is first converted to a corresponding rate, preferably expressed in beats per minute (bpm), and then stored in a file, taking the place of the earliest measurement previously stored. After a new measurement is entered into the file, the stored measurements are averaged, to produce an average rate measurement. The CPU optionally determines which of the stored measurements differs most from the average, and replaces that measurement with the average.

Upon initiation, the CPU increments a period timer used in measuring the time duration between successive pulses. This timer is incremented in steps of about two milliseconds in one embodiment. It is then determined whether or not a pulse has occurred during the previous two milliseconds. If it has not, the CPU returns to the initial step of incrementing the period timer. If a heartbeat has occurred, on the other hand, the CPU converts the time duration measurement currently stored in the period timer to a corresponding heartbeat rate, preferably expressed in bpm. After the heartbeat rate measurement is computed, the CPU determines whether or not the computed rate is intermediate prescribed thresholds of 20 bpm and 240 bpm. If it is not, it is assumed that the detected pulse was not in fact a heartbeat and the period timer is cleared.

In an optical heartbeat detector embodiment, an optical transducer is positioned on a finger, wrist, or ear lobe. The ear, wrist or finger pulse oximeter waveform is then analyzed to extract the beat-to-beat amplitude, area, and width (half height) measurements. The oximeter waveform is used to generate heartbeat rate in this embodiment. In one implementation, a reflective sensor such as the Honeywell HLC1395 can be used. The device emits lights from a window in the infrared spectrum and receives reflected light in a second window. When the heart beats, blood flow increases temporarily and more red blood cells flow through the windows, which increases the light reflected back to the detector. The light can be reflected, refracted, scattered, and absorbed by one or more detectors. Suitable noise reduction is done, and the resulting optical waveform is captured by the CPU.

In another optical embodiment, blood pressure is estimated from the optical reading using a mathematical model such as a linear correlation with a known blood pressure reading. In this embodiment, the pulse oximeter readings are compared to the blood-pressure readings from a known working blood pressure measurement device during calibration. Using these measurements the linear equation is developed relating oximeter output waveform such as width to blood-pressure (systolic, mean and pulse pressure). In one embodiment, a transform (such as a Fourier analysis or a Wavelet transform) of the oximeter output can be used to generate a model to relate the oximeter output waveform to the blood pressure. Other non-linear math model or relationship can be determined to relate the oximeter waveform to the blood pressure.

In one implementation, the pulse oximeter probe and a blood pressure cuff are placed on the corresponding contralateral limb to the oscillometric (Dinamap 8100; Critikon, Inc, Tampa, Fla., USA) cuff site. The pulse oximeter captures data on plethysmographic waveform, heart rate, and oxygen saturation. Simultaneous blood pressure measurements were obtained from the oscillometric device, and the pulse oximeter. Systolic, diastolic, and mean blood pressures are recorded from the oscillometric device. This information is used derive calibration parameters relating the pulse oximeter output to the expected blood pressure. During real time operation, the calibration parameters are applied to the oximeter output to predict blood pressure in a continuous or in a periodic fashion. In yet another embodiment, the device includes an accelerometer or alternative motion-detecting device to determine when the patient' hand is at rest, thereby reducing motion-related artifacts introduced to the measurement during calibration and/or operation. The accelerometer can also function as a falls detection device.

In an ultrasonic embodiment, a piezo film sensor element is placed on the wristwatch band. The sensor can be the SDT1-028K made by Measurement Specialties, Inc. The sensor should have features such as: (a) it is sensitive to low level mechanical movements, (b) it has an electrostatic shield located on both sides of the element (to minimize 50/60 Hz AC line interference), (c) it is responsive to low frequency movements in the 0.7-12 Hz range of interest. A filter/amplifier circuit has a three-pole low pass filter with a lower (−3 dB) cutoff frequency at about 12-13 Hz. The low-pass filter prevents unwanted 50/60 Hz AC line interference from entering the sensor. However, the piezo film element has a wide band frequency response so the filter also attenuates any extraneous sound waves or vibrations that get into the piezo element. The DC gain is about +30 dB.

Waveform averaging can be used to reduce noise. It reinforces the waveform of interest by minimizing the effect of any random noise. These pulses were obtained when the arm was motionless. If the arm was moved while capturing the data the waveform did not look nearly as clean. That's because motion of the arm causes the sonic vibrations to enter the piezo film through the arm or by way of the cable. An accelerometer is used to detect arm movement and used to remove inappropriate data capture.

In one embodiment that can determine blood pressure, two piezo film sensors and filter/amplifier circuits can be configured as a non-invasive velocity type blood pressure monitor. One sensor can be on the wrist and the other can be located on the inner left elbow at the same location where Korotkoff sounds are monitored during traditional blood pressure measurements with a spygmometer. The correlation between pulse delay and blood pressure is well known in the art of non-invasive blood pressure monitors.

In yet another embodiment, an ultrasonic transducer generates and transmits an acoustic wave into the user's body such as the wrist or finger. The transducer subsequently receives pressure waves in the form of echoes resulting from the transmitted acoustic waves. In one embodiment, an ultrasonic driving and receiving circuit generates electrical pulses which, when applied to the transducer produce acoustic energy having a frequency on the order of 8 MHz, a pulse width or duration of approximately 8 microseconds, and a pulse repetition interval (PRI) of approximately 16 microseconds, although other values of frequency, pulse width, and PRI may be used. Hence, the transducer emits an 8 microsecond ultrasonic pulse, which is followed by an 8 microsecond "listen" period, every 16 microseconds. The echoes from these pulses are received by the ultrasonic transducer during the listen period. The ultrasonic transducer can be a ceramic piezoelectric device of the type well known in the art, although other types may be substituted. The transducer converts the received acoustic signal to an electrical signal, which is then supplied to the receiving section of the ultrasonic driver and receiver circuit 616, which contains two receiver circuits. The output of the first receiver circuit is an analog signal representative of the Doppler frequency of the echo received by the transducer which is digitized and supplied to the CPU. Within the CPU, the digitized Doppler frequency is scaled to compute the blood velocity within the artery based on the Doppler frequency. The time-frequency distribution of the blood velocity is then computed. Finally, the CPU maps in time the peak of the time-frequency distribution to the corresponding pressure waveform to produce the estimated mean arterial pressure (MAP). The output of the ultrasonic receiver circuit is an analog echo signal proportional to absorption of the transmitted frequencies by blood or tissue. This analog signal is digitized and process so that each group of echoes, generated for a different transversal position, is integrated to determine a mean value. The mean echo values are compared to determine the minimum value, which is caused by direct positioning over the artery. In one embodiment, the device includes an accelerometer or alternative motion-detecting device to determine when the patient' hand is at rest, thereby reducing motion-related artifacts introduced to the measurement.

In yet another ultrasonic embodiment, a transducer includes a first and a second piezoelectric crystal, wherein the crystals are positioned at an angle to each other, and wherein the angle is determined based on the distance of the transducer to the living subject. The first piezoelectric crystal is energized by an original ultrasonic frequency signal, wherein the original ultrasonic frequency signal is reflected off the living subject and received by the second piezoelectric crystal. More specifically, the system includes a pair of piezoelectric crystals at an angle to each other, wherein the angle is determined by the depth of the object being monitored. If the object is the radial artery of a human subject (e.g., adult, infant), the angle of the two crystals with respect to the direction of the blood flow would be about 5 to about 20 degrees. One of the crystals is energized at an ultrasonic frequency. The signal is then reflected back by the user's wrist and picked up by the second crystal. The frequency received is either higher or lower than the original frequency depending upon the direction and the speed of the fluidic mass flow. For example, when blood flow is monitored, the direction of flow is fixed. Thus, the Doppler frequency which is the difference between the original and the reflected frequency depends only upon the speed of the blood flow. Ultrasonic energy is delivered to one of the two piezoelectric elements in the module by the power amplifier. The other element picks up the reflected ultrasonic signal as Doppler frequencies.

In a digital stethoscope embodiment, a microphone or a piezoelectric transducer is placed near the wrist artery to pick up heart rate information. In one embodiment, the microphone sensor and optionally the EKG sensor are place on the wrist band 1374 of the watch to analyze the acoustic signal or signals emanating from the cardiovascular system and, optionally can combine the sound with an electric signal (EKG) emanating from the cardiovascular system and/or an acoustic signal emanating from the respiratory system. The system can perform automated auscultation of the cardiovascular system, the respiratory system, or both. For example, the system can differentiate pathological from benign heart murmurs, detect cardiovascular diseases or conditions that might otherwise escape attention, recommend that the patient go through for a diagnostic study such as an echocardiography or to a specialist, monitor the course of a disease and the effects of therapy, decide when additional therapy or intervention is necessary, and providing a more objective basis for the decision(s) made. In one embodiment, the analysis includes selecting one or more beats for analysis, wherein each beat comprises an acoustic signal emanating from the cardiovascular system; performing a time-frequency analysis of beats selected for analysis so as to provide information regarding the distribution of energy, the relative distribution of energy, or both, over different frequency ranges at one or more points in the cardiac cycle; and processing the information to reach a clinically relevant conclusion or recommendation. In another implementation, the system selects one or more beats for analysis, wherein each beat comprises an acoustic signal emanating from the cardiovascular system; performs a time-frequency analysis of beats selected for analysis so as to provide information regarding the distribution of energy, the relative distribution of energy, or both, over different frequency ranges at one or more points in the cardiac cycle; and present information derived at least in part from the acoustic signal, wherein the information comprises one or more items selected from the group consisting of: a visual or audio presentation of a prototypical beat, a display of the time-frequency decomposition of one or more beats or prototypical beats, and a playback of the acoustic signal at a reduced rate with preservation of frequency content.

In an electromagnetic embodiment where the wrist band incorporates a flexible magnet to provide a magnetic field and one or more electrodes positioned on the wrist band to measure voltage drops which are proportional to the blood velocity, instantaneously variation of the flow can be detected but not artery flow by itself. To estimate the flow of blood in the artery, the user or an actuator such as motorized cuff temporarily stops the blood flow in the vein by applying external pressure or by any other method. During the period of time in which the vein flow is occluded, the decay of the artery flow is measured. This measurement may be used for zeroing the sensor and may be used in a model for estimating the steady artery flow. The decay in artery flow due to occlusion of veins is measured to arrive at a model the rate of artery decay. The system then estimates an average artery flow before occlusion. The blood flow can then be related to the blood pressure.

In another embodiment, an ionic flow sensor is used with a driving electrode that produces a pulsatile current. The pulsatile current causes a separation of positive and negative charges that flows in the blood of the arteries and veins passing in the wrist area. Using electrophoresis principle, the resistance of the volume surrounded by the source first decreases and then increases. The difference in resistance in the blood acts as a mark that moves according to the flow of blood so that marks are flowing in opposite directions by arteries and veins.

In the above embodiments, accelerometer information is used to detect that the patient is at rest prior to making a blood pressure measurement and estimation. Further, a temperature sensor may be incorporated so that the temperature is known at any minute. The processor correlates the temperature measurement to the blood flow measurement for calibration purposes.

In another embodiment, the automatic identification of the first, second, third and fourth heart sounds (S1, S2, S3, S4) is done. In yet another embodiment, based on the heart sound, the system analyzes the patient for mitral valve prolapse. The system performs a time-frequency analysis of an acoustic signal emanating from the subject's cardiovascular system and examines the energy content of the signal in one or more frequency bands, particularly higher frequency bands, in order to determine whether a subject suffers from mitral valve prolapse.

FIG. 7 shows an exemplary mesh network that includes the wrist-watch of FIG. 6 in communication with a mesh network including a telephone such as a wired telephone as well as a cordless telephone. In one embodiment, the mesh network is an IEEE 802.15.4 (ZigBee) network. IEEE 802.15.4 defines two device types; the reduced function device (RFD) and the full function device (FFD). In ZigBee these are referred to as the ZigBee Physical Device types. In a ZigBee network a node can have three roles: ZigBee Coordinator, ZigBee Router, and ZigBee End Device. These are the ZigBee Logical Device types. The main responsibility of a ZigBee Coordinator is to establish a network and to define its main parameters (e.g. choosing a radio-frequency channel and defining a unique network identifier). One can extend the communication range of a network by using ZigBee Routers. These can act as relays between devices that are too far apart to communicate directly. ZigBee End Devices do not participate in routing. An FFD can talk to RFDs or other FFDs, while an RFD can talk only to an FFD. An RFD is intended for applications that are extremely simple, such as a light switch or a passive infrared sensor; they do not have the need to send large amounts of data and may only associate with a single FFD at a time. Consequently, the RFD can be implemented using minimal resources and memory capacity and have lower cost than an FFD. An FFD can be used to implement all three ZigBee Logical Device types, while an RFD can take the role as an End Device.

One embodiment supports a multicluster-multihop network assembly to enable communication among every node in a distribution of nodes. The algorithm should ensure total connectivity, given a network distribution that will allow total connectivity. One such algorithm of an embodiment is described in U.S. Pat. No. 6,832,251, the content of which is incorporated by referenced. The '251 algorithm runs on each node independently. Consequently, the algorithm does not have global knowledge of network topology, only local knowledge of its immediate neighborhood. This makes it well suited to a wide variety of applications in which the topology may be time-varying, and the number of nodes may be unknown. Initially, all nodes consider themselves remotes on cluster zero. The assembly algorithm floods one packet (called an assembly packet) throughout the network. As the packet is flooded, each node modifies it slightly to indicate what the next node should do. The assembly packet tells a node whether it is a base or a remote, and to what cluster it belongs. If a node has seen an assembly packet before, it will ignore all further assembly packets.

The algorithm starts by selecting (manually or automatically) a start node. For example, this could be the first node to wake up. This start node becomes a base on cluster 1, and floods an assembly packet to all of its neighbors, telling them to be remotes on cluster 1. These remotes in turn tell all their neighbors to be bases on cluster 2. Only nodes that have not seen an assembly packet before will respond to this request, so nodes that already have decided what to be will not change their status. The packet continues on, oscillating back and forth between "become base/become remote", and increasing the cluster number each time. Since the packet is flooded to all neighbors at every step, it will reach every node in the network. Because of the oscillating nature of the "become base/become remote" instructions, no two bases will be adjacent. The basic algorithm establishes a multi-cluster network with all gateways between clusters, but self-assembly time is proportional with the size of the network. Further, it includes only single hop clusters. Many generalizations are possible, however. If many nodes can begin the network nucleation, all that is required to harmonize the clusters is a mechanism that recognizes precedence (e.g., time of nucleation, size of sub-network), so that conflicts in boundary clusters are resolved. Multiple-hop clusters can be enabled by means of establishing new clusters from nodes that are N hops distant from the master.

Having established a network in this fashion, the masters can be optimized either based on number of neighbors, or other criteria such as minimum energy per neighbor communication. Thus, the basic algorithm is at the heart of a number of variations that lead to a scalable multi-cluster network that establishes itself in time, and that is nearly independent of the number of nodes, with clusters arranged according to any of a wide range of optimality criteria. Network synchronism is established at the same time as the network connections, since the assembly packet(s) convey timing information outwards from connected nodes.

The network nodes can be mesh network appliances to provide voice communications, home security, door access control, lighting control, power outlet control, dimmer control, switch control, temperature control, humidity control, carbon monoxide control, fire alarm control, blind control, shade control, window control, oven control, cooking range control, personal computer control, entertainment console control, television control, projector control, garage door control, car control, pool temperature control, water pump control, furnace control, heater control, thermostat control, electricity meter monitor, water meter monitor, gas meter monitor, or remote diagnostics. The telephone can be connected to a cellular telephone to answer calls directed at the cellular telephone. The connection can be wired or wireless using Bluetooth or ZigBee. The telephone synchronizes calendar, contact, emails, blogs, or instant messaging with the cellular telephone. Similarly, the telephone synchronizes calendar, contact, emails, blogs, or instant messaging with a personal computer. A web server can communicate with the Internet through the POTS to provide information to an authorized remote user who logs into the server. A wireless router such as 802.11 router, 802.16 router, WiFi router, WiMAX router, Bluetooth router, X10 router can be connected to the mesh network.

A mesh network appliance can be connected to a power line to communicate X10 data to and from the mesh network. X10 is a communication protocol that allows up to 256 X10 products to talk to each other using the existing electrical wiring in the home. Typically, the installation is simple, a transmitter plugs (or wires) in at one location in the home and sends its control signal (on, off, dim, bright, etc.) to a receiver which plugs (or wires) into another location in the home. The mesh network appliance translates messages intended for X10 device to be relayed over the ZigBee wireless network, and then transmitted over the power line using a ZigBee to X10 converter appliance.

An in-door positioning system links one or more mesh network appliances to provide location information. Inside the home or office, the radio frequency signals have negligible multipath delay spread (for timing purposes) over short distances. Hence, radio strength can be used as a basis for determining position. Alternatively, time of arrival can be used to determine position, or a combination of radio signal strength and time of arrival can be used. Position estimates can also be achieved in an embodiment by beamforming, a method that exchanges time-stamped raw data among the nodes. While the processing is relatively more costly, it yields processed data with a higher signal to noise ratio (SNR) for subsequent classification decisions, and enables estimates of angles of arrival for targets that are outside the convex hull of the participating sensors. Two such clusters of ZigBee nodes can then provide for triangulation of distant targets. Further, beamforming enables suppression of interfering sources, by placing nulls in the synthetic beam pattern in their directions. Another use of beamforming is in self-location of nodes when the positions of only a very small number of nodes or appliances are known such as those sensors nearest the wireless stations. In one implementation where each node knows the distances to its neighbors due to their positions, and some small fraction of the nodes (such as those nearest a PC with GPS) of the network know their true locations. As part of the network-building procedure, estimates of the locations of the nodes that lie within or near the convex hull of the nodes with known position can be quickly generated. To start, the shortest distance (multihop) paths are determined between each reference node. All nodes on this path are assigned a location that is the simple linear average of the two reference locations, as if the path were a straight line. A node which lies on the intersection of two such paths is assigned the average of the two indicated locations. All nodes that have been assigned locations now serve as references. The shortest paths among these new reference nodes are computed, assigning locations to all intermediate nodes as before, and continuing these iterations until no further nodes get assigned locations. This will not assign initial position estimates to all sensors. The remainder can be assigned locations based on pairwise averages of distances to the nearest four original reference nodes. Some consistency checks on location can be made using trigonometry and one further reference node to determine whether or not the node likely lies within the convex hull of the original four reference sensors.

In two dimensions, if two nodes have known locations, and the distances to a third node are known from the two nodes, then trigonometry can be used to precisely determine the location of the third node. Distances from another node can resolve any ambiguity. Similarly, simple geometry produces precise calculations in three dimensions given four reference nodes. But since the references may also have uncertainty, an alternative procedure is to perform a series of iterations where successive trigonometric calculations result only in a delta of movement in the position of the node. This process can determine locations of nodes outside the convex hull of the reference sensors. It is also amenable to averaging over the positions of all neighbors, since there will often be more neighbors than are strictly required to determine location. This will reduce the effects of distance measurement errors.

Alternatively, the network can solve the complete set of equations of intersections of hyperbola as a least squares optimization problem.

In yet another embodiment, any or all of the nodes may include transducers for acoustic, infrared (IR), and radio frequency (RF) ranging. Therefore, the nodes have heterogeneous capabilities for ranging. The heterogeneous capabilities further include different margins of ranging error. Furthermore, the ranging system is re-used for sensing and communication functions. For example, wideband acoustic functionality is available for use in communicating, bistatic sensing, and ranging. Such heterogeneous capability of the sensors 40 can provide for ranging functionality in addition to communications functions. As one example, repeated use of the communications function improves position determination accuracy over time. Also, when the ranging and the timing are conducted together, they can be integrated in a self-organization protocol in order to reduce energy consumption. Moreover, information from several ranging sources is capable of being fused to provide improved accuracy and resistance to environmental variability. Each ranging means is exploited as a communication means, thereby providing improved robustness in the presence of noise and interference. Those skilled in the art will realize that there are many architectural possibilities, but allowing for heterogeneity from the outset is a component in many of the architectures.

Figure 8:
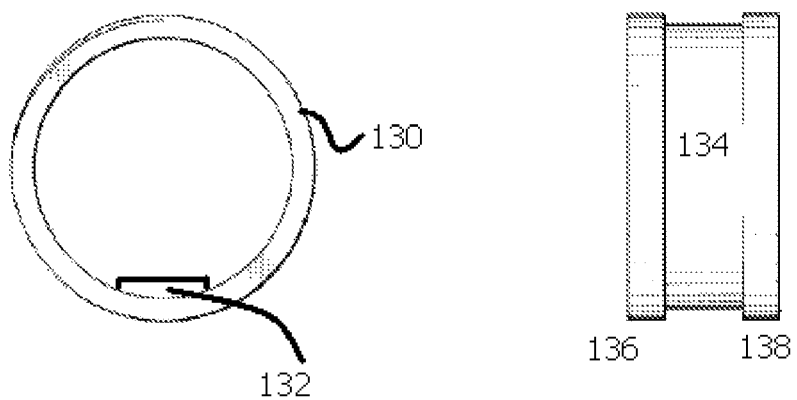
FIGS. 8-14 show various exemplary wearable appliances to monitor a patient.

Turning now to FIGS. 8-13, various exemplary monitoring devices are shown. In FIG. 8, a ring 130 has an opening 132 for transmitting and receiving acoustic energy to and from the sensor 84 in an acoustic implementation. In an optical implementation, a second opening (not shown) is provided to emit an optical signal from an LED, for example, and an optical detector can be located at the opening 132 to receive the optical signal passing through the finger wearing the ring 130. In another implementation, the ring has an electrically movable portion 134 and rigid portions 136-138 connected thereto. The electrically movable portion 134 can squeeze the finger as directed by the CPU during an applanation sweep to determine the arterial blood pressure.

Figure 9:
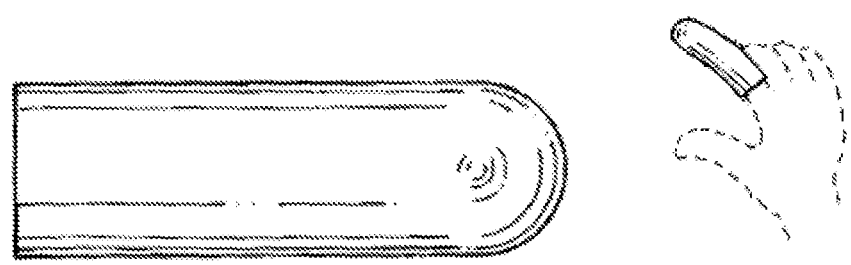

FIG. 9 shows an alternate finger cover embodiment where a finger-mounted module housing the photo-detector and light source. The finger mounted module can be used to measure information that is processed to determine the user's blood pressure by measuring blood flow in the user's finger and sending the information through a wireless connection to the base station. In one implementation, the housing is made from a flexible polymer material.

Figure 10:
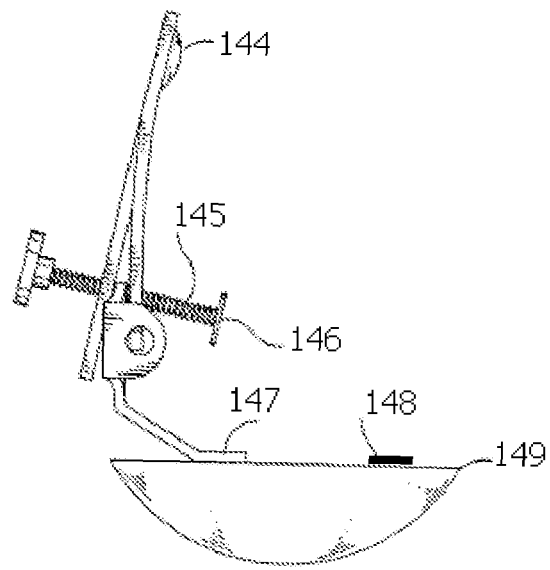

In an embodiment to be worn on the patient's ear lobe, the monitoring device can be part of an earring jewelry clipped to the ear lobe. In the implementation of FIG. 10, the monitoring device has a jewelry body 149 that contains the monitoring electronics and power source. The surface of the body 149 is an ornamental surface such as jade, ivory, pearl, silver, or gold, among others. The body 149 has an opening 148 that transmits energy such as optical or acoustic energy through the ear lobe to be detected by a sensor 144 mounted on a clamp portion that is secured to the body 149 at a base 147. The energy detected through the sensor 144 is communicated through an electrical connector to the electronics in the jewelry body 149 for processing the received energy and for performing wireless communication with a base station. In FIG. 2E, a bolt 145 having a stop end 146 allows the user to adjust the pressure of the clamp against the ear lobe. In other implementations, a spring biased clip is employed to retain the clip on the wearer's ear lobe. A pair of members, which snap together under pressure, are commonly used and the spring pressure employed should be strong enough to suit different thicknesses of the ear lobe.

Figure 11:
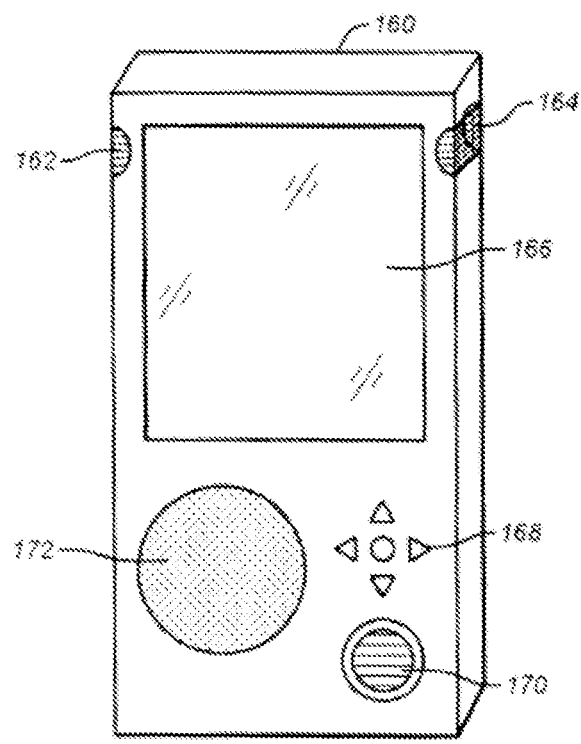
Figure 12:
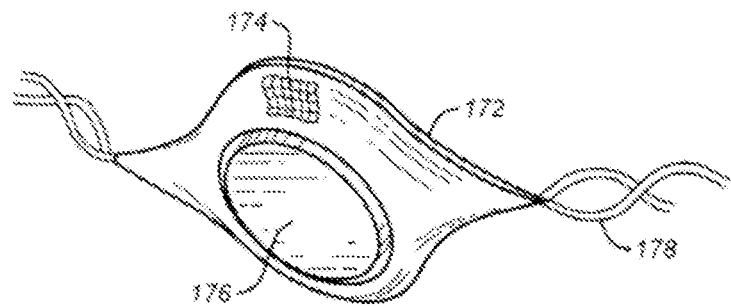

FIGS. 11 and 12 show two additional embodiments of the monitoring device. In FIG. 11, a wearable monitoring device is shown. The monitoring device has a body 160 comprising microphone ports 162, 164 and 170 arranged in a first order noise cancelling microphone arrangement. The microphones 162 and 164 are configured to optimally receive distant noises, while the microphone 170 is optimized for capturing the user's speech. A touch sensitive display 166 and a plurality of keys 168 are provided to capture hand inputs. Further, a speaker 172 is provided to generate a verbal feedback to the user.

Turning now to FIG. 12, a jewelry-sized monitoring device is illustrated. In this embodiment, a body 172 houses a microphone port 174 and a speaker port 176. The body 172 is coupled to the user via the necklace 178 so as to provide a personal, highly accessible personal computer. Due to space limitations, voice input/output is an important user interface of the jewelry-sized computer. Although a necklace is disclosed, one skilled in the art can use a number of other substitutes such as a belt, a brace, a ring, or a band to secure the jewelry-sized computer to the user.

Figure 13:
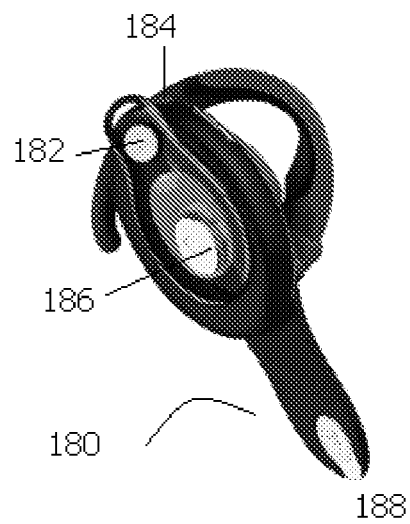

FIG. 13 shows an exemplary ear phone embodiment 180. The ear phone 180 has an optical transmitter 182 which emits LED wavelengths that are received by the optical receiver 184. The blood oximetry information is generated and used to determine blood pulse or blood pressure. Additionally, a module 186 contains mesh network communication electronics, accelerometer, and physiological sensors such as EKG/ECG sensors or temperature sensors or ultrasonic sensors. In addition, a speaker (not shown) is provided to enable voice communication over the mesh network, and a microphone 188 is provided to pick up voice during verbal communication and pick up heart sound when the user is not using the microphone for voice communication. The ear phone optionally has an ear canal temperature sensor for sensing temperature in a human.

Figure 14:
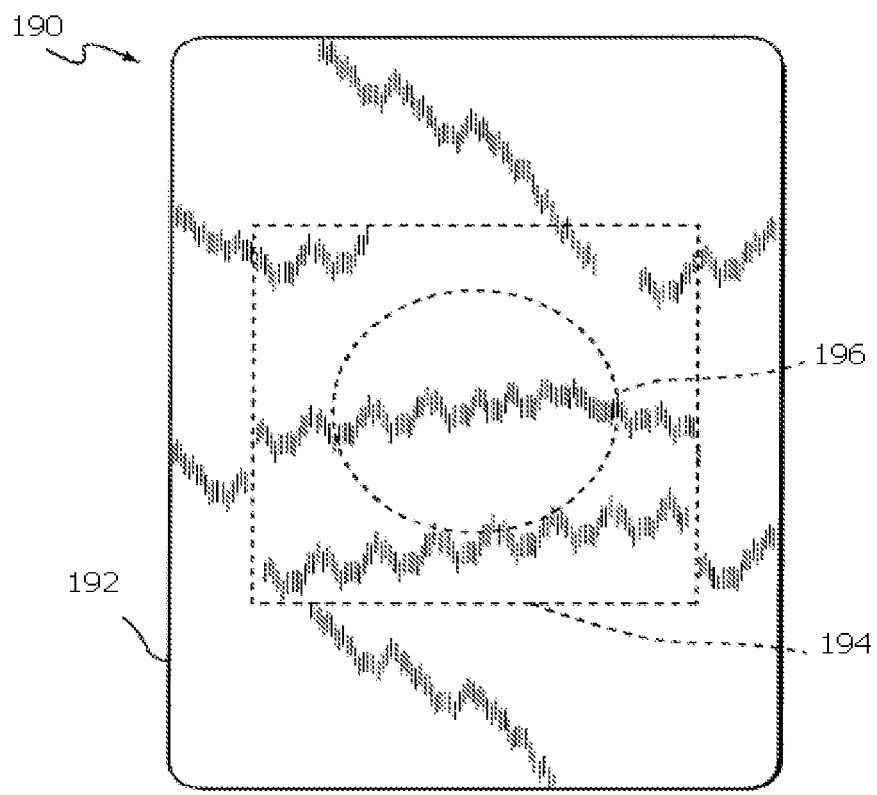

FIG. 14 shows an exemplary adhesive patch embodiment. The patch may be applied to a persons skin by anyone including the person themselves or an authorized person such as a family member or physician. The adhesive patch is shown generally at 190 having a gauze pad 194 attached to one side of a backing 192, preferably of plastic, and wherein the pad can have an impermeable side 194 coating with backing 192 and a module 196 which contains electronics for communicating with the mesh network and for sensing acceleration and EKG/ECG, heart sound, microphone, optical sensor, or ultrasonic sensor in contacts with a wearer's skin. In one embodiment, the module 196 has a skin side that may be coated with a conductive electrode lotion or gel to improve the contact. The entire patch described above may be covered with a plastic or foil strip to retain moisture and retard evaporation by a conductive electrode lotion or gel provided improve the electrode contact. In one embodiment, an acoustic sensor (microphone or piezoelectric sensor) and an electrical sensor such as EKG sensor contact the patient with a conductive gel material. The conductive gel material provides transmission characteristics so as to provide an effective acoustic impedance match to the skin in addition to providing electrical conductivity for the electrical sensor. The acoustic transducer can be directed mounted on the conductive gel material substantially with or without an intermediate air buffer. The entire patch is then packaged as sterile as are other over-the-counter adhesive bandages. When the patch is worn out, the module 196 may be removed and a new patch backing 192 may be used in place of the old patch. One or more patches may be applied to the patient's body and these patches may communicate wirelessly using the mesh network or alternatively they may communicate through a personal area network using the patient's body as a communication medium.

The term "positional measurement," as that term is used herein, is not limited to longitude and latitude measurements, or to metes and bounds, but includes information in any form from which geophysical positions can be derived. These include, but are not limited to, the distance and direction from a known benchmark, measurements of the time required for certain signals to travel from a known source to the geophysical location where the signals may be electromagnetic or other forms, or measured in terms of phase, range, Doppler or other units.

Figure 15A:
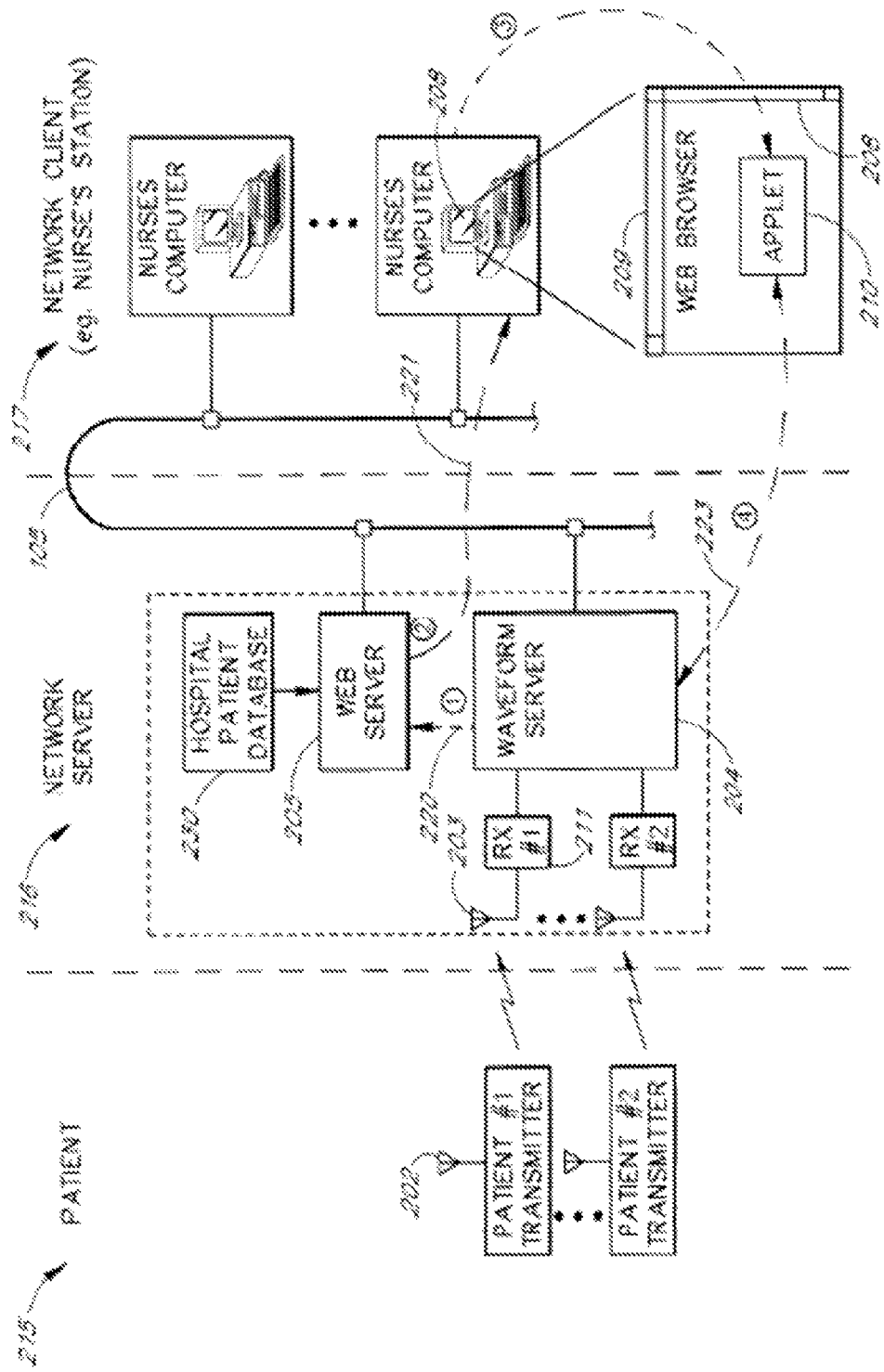
FIGS. 15A-15B show exemplary systems for performing patient monitoring.

FIG. 15A shows a system block diagram of the network-based patient monitoring system in a hospital or nursing home setting. The system has a patient component 215, a server component 216, and a client component 217. The patient component 215 has one or more mesh network patient transmitters 202 for transmitting data to the central station. The central server comprises one or more Web servers 205, one or more waveform servers 204 and one or more mesh network receivers 211. The output of each mesh network receiver 211 is connected to at least one of the waveform servers 204. The waveform servers 204 and Web the servers 205 are connected to the network 105. The Web servers 205 are also connected to a hospital database 230. The hospital database 230 contains patient records. In the embodiment of FIG. 15A, a plurality of nurse stations provide a plurality of nurse computer user interface 208. The user interface 208 receives data from an applet 210 that communicates with the waveform server 204 and updates the display of the nurse computers for treating patients.

The network client component 217 comprises a series of workstations 106 connected to the network 105. Each workstation 106 runs a World Wide Web (WWW or Web) browser application 208. Each Web browser can open a page that includes one or more media player applets 210. The waveform servers 204 use the network 105 to send a series of messages 220 to the Web servers 205. The Web servers 205 use the network 105 to communicate messages, shown as a path 221, to the workstations 106. The media player applets running on the workstations 106 use the network 105 to send messages over a path 223 directly to the waveform servers 204.

Figure 15B:
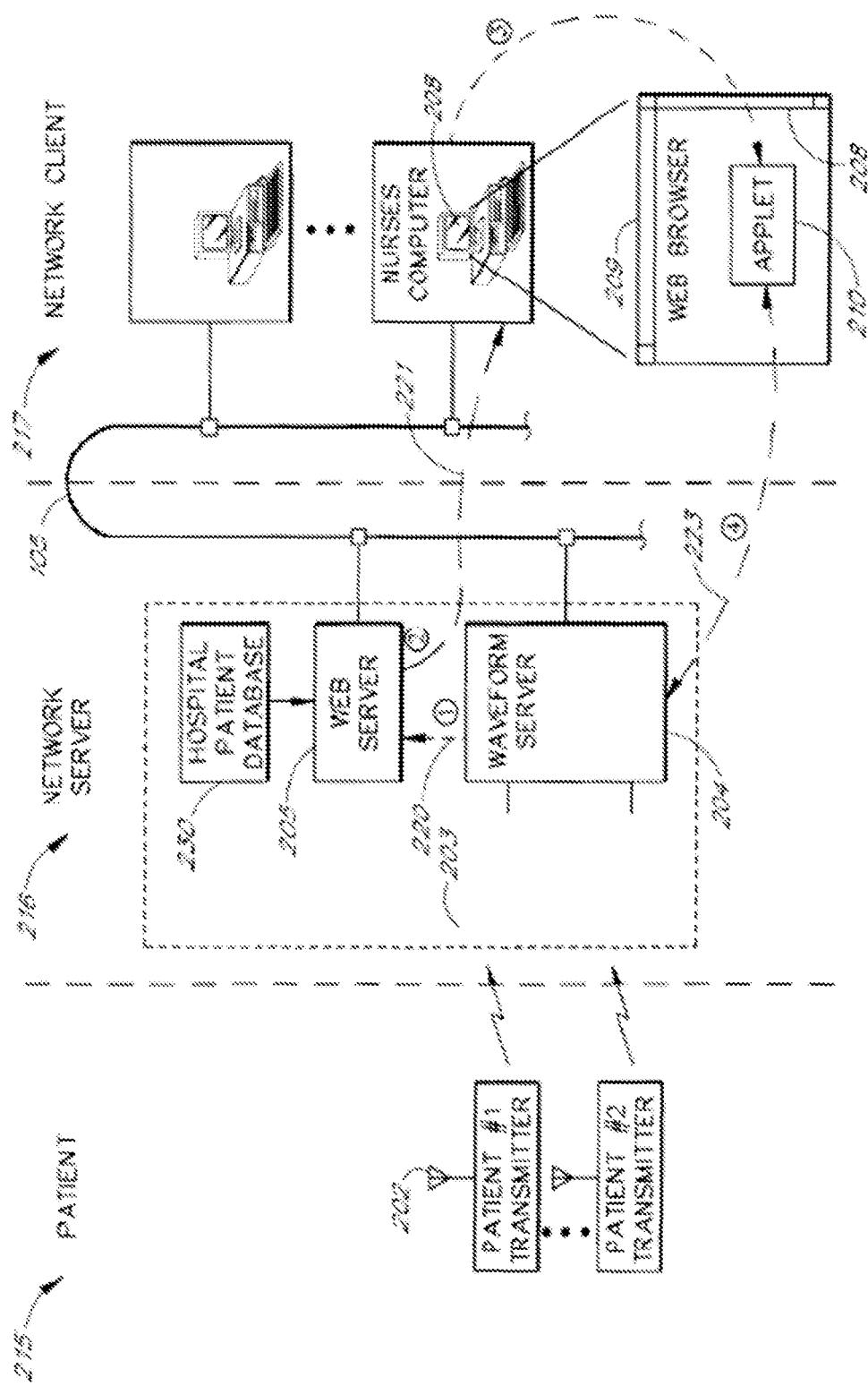

FIG. 15B shows a variation of the system of FIG. 15A for call center monitoring. In this embodiment, the patient appliances 202 wirelessly communicate to home base stations (not shown) which are connected to the POTS or PSTN network for voice as well as data transmission. The data is captured by the waveform server 204 and the voice is passed through to the call center agent computer 207 where the agent can communicate by voice with the patient. The call center agent can forward the call to a professional such as a nurse or doctor or emergency service personnel if necessary. Hence, the system can include a patient monitoring appliance coupled to the POTS or PSTN through the mesh network. The patient monitoring appliance monitors drug usage and patient falls. The patient monitoring appliance monitors patient movement. A call center can call to the telephone to provide a human response.

In one exemplary monitoring service providing system, such as an emergency service providing system, the system includes a communication network (e.g., the Public Switch Telephone Network or PSTN or POTS), a wide area communication network (e.g., TCP/IP network) in call centers. The communication network receives calls destined for one of the call centers. In this regard, each call destined for one of the call centers is preferably associated with a particular patient, a call identifier or a call identifier of a particular set of identifiers. A call identifier associated with an incoming call may be an identifier dialed or otherwise input by the caller. For example, the call centers may be locations for receiving calls from a particular hospital or nursing home.

To network may analyze the automatic number information (ANI) and/or automatic location information (ALI) associated with the call. In this regard, well known techniques exist for analyzing the ANI and ALI of an incoming call to identify the call as originating from a particular calling device or a particular calling area. Such techniques may be employed by the network to determine whether an incoming call originated from a calling device within an area serviced by the call centers. Moreover, if an incoming call originated from such an area and if the incoming call is associated with the particular call identifier referred to above, then the network preferably routes the call to a designated facility.

When a call is routed to the facility, a central data manager, which may be implemented in software, hardware, or a combination thereof, processes the call according to techniques that will be described in more detail hereafter and routes the call, over the wide area network, to one of the call centers depending on the ANI and/or ALI associated with the call. In processing the call, the central data manager may convert the call from one communication protocol to another communication protocol, such as voice over internet protocol (VoIP), for example, in order to increase the performance and/or efficiency of the system. The central data manager may also gather information to help the call centers in processing the call. There are various techniques that may be employed by the central data manager to enhance the performance and/or efficiency of the system, and examples of such techniques will be described in more detail hereafter.

Various benefits may be realized by utilizing a central facility to intercept or otherwise receive a call from the network and to then route the call to one of the call centers via WAN. For example, serving multiple call centers with a central data manager, may help to reduce total equipment costs. In this regard, it is not generally necessary to duplicate the processing performed by the central data manager at each of the call centers. Thus, equipment at each of the call centers may be reduced. As more call centers are added, the equipment savings enabled by implementing equipment at the central data manager instead of the call centers generally increases. Furthermore, the system is not dependent on any telephone company's switch for controlling the manner in which data is communicated to the call centers. In this regard, the central data manager may receive a call from the network and communicate the call to the destination call centers via any desirable communication technique, such as VoIP, for example. Data security is another possible benefit of the exemplary system 10 as the central data manager is able to store the data for different network providers associated with network on different partitions.

Figure 15C:
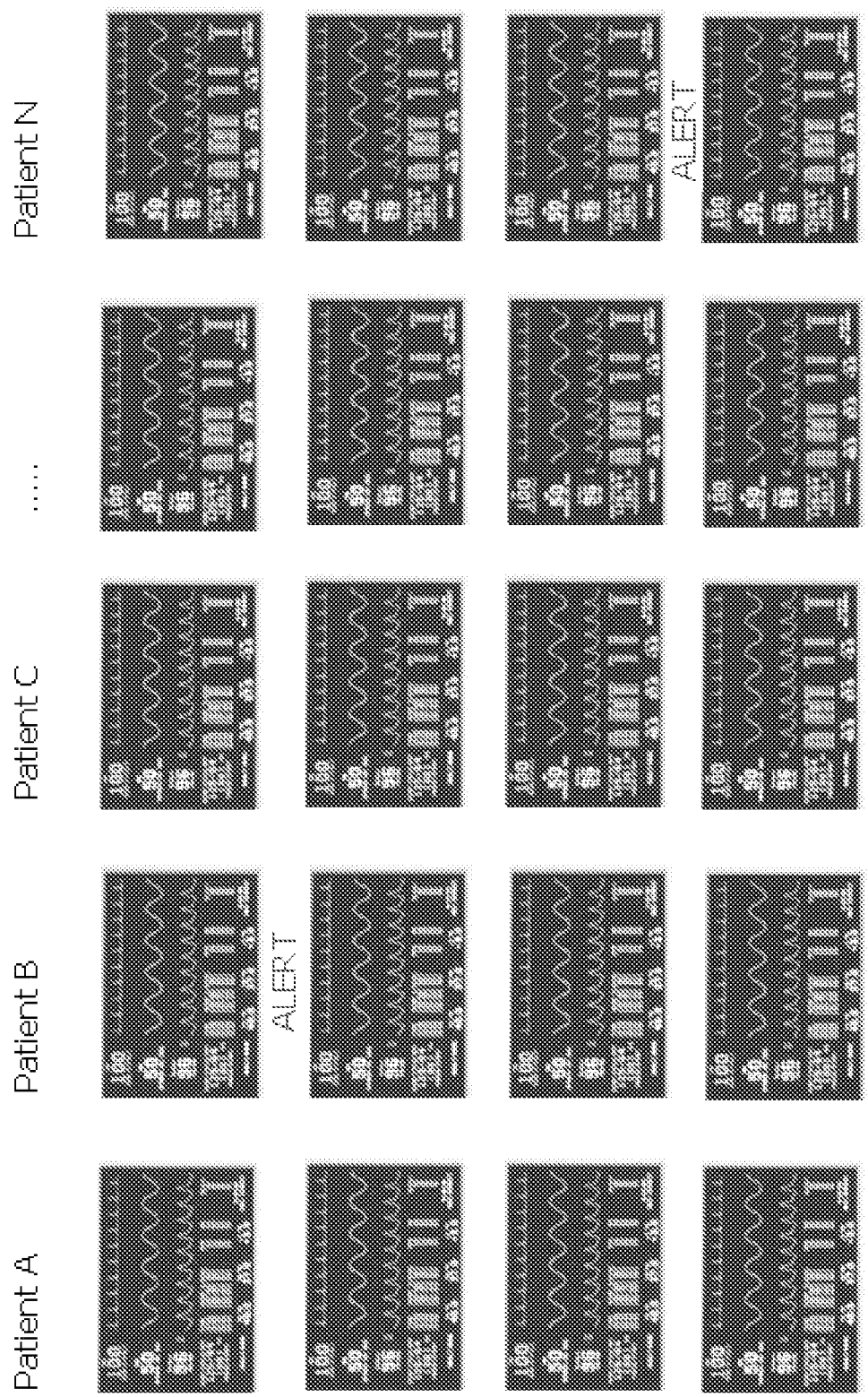
FIG. 15C shows an exemplary interface to monitor a plurality of persons.
Figure 15D:
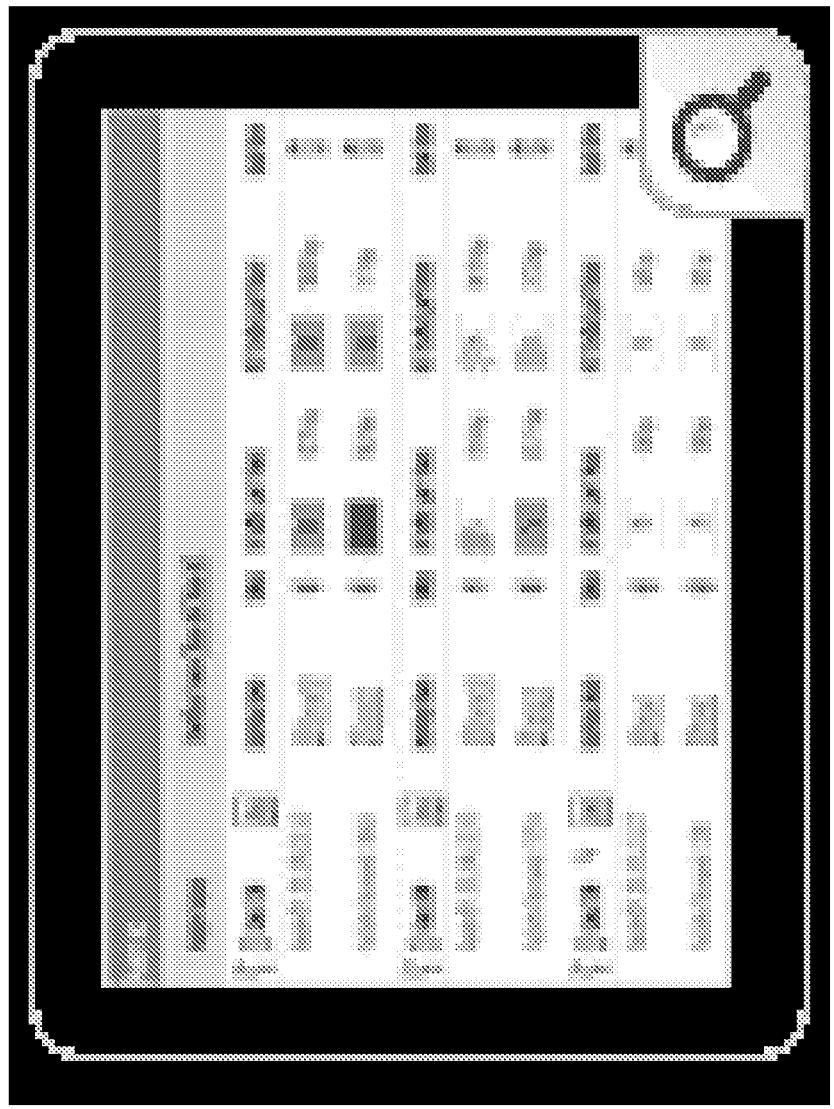
FIG. 15D shows an exemplary dash-board that provides summary information on the status of a plurality of persons.

While the patient interface 90 (FIG. 1A) can provide information for a single person, FIG. 15C shows an exemplary interface to monitor a plurality of persons, while FIG. 15D shows an exemplary dash-board that provides summary information on the status of a plurality of persons. As shown in FIG. 1C, for professional use such as in hospitals, nursing homes, or retirement homes, a display can track a plurality of patients. In FIG. 15C, a warning (such as sound or visual warning in the form of light or red flashing text) can be generated to point out the particular patient that may need help or attention. In FIG. 15D, a magnifier glass can be dragged over a particular individual icon to expand and show detailed vital parameters of the individual and if available, images from the camera 10 trained on the individual for real time video feedback. The user can initiate voice communication with the user for confirmation purposes by clicking on a button provided on the interface and speaking into a microphone on the professional's workstation.

Figure 15E:
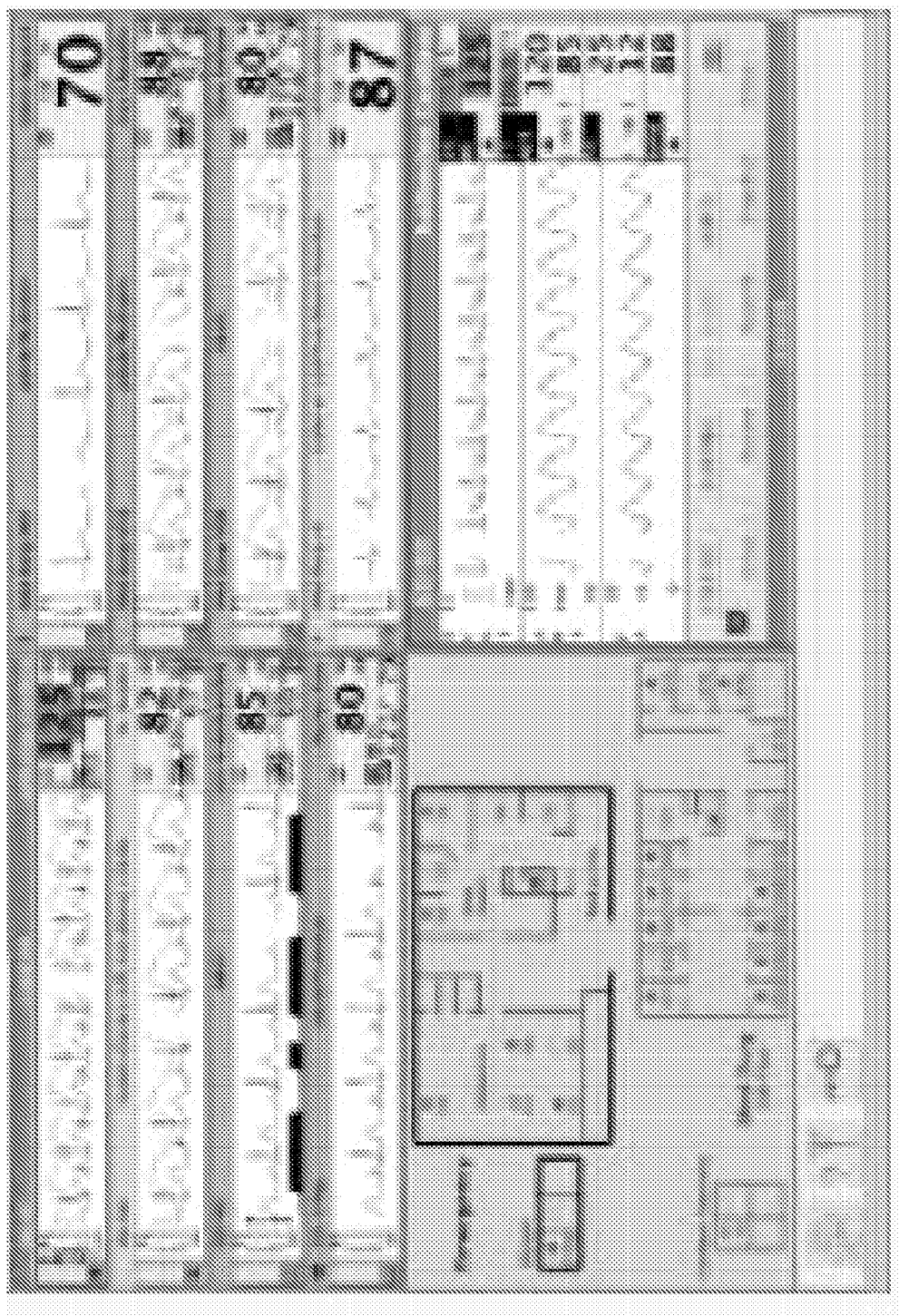
FIG. 15E shows an exemplary multi-station vital parameter user interface for a professional embodiment.
Figures 15F, 16A:
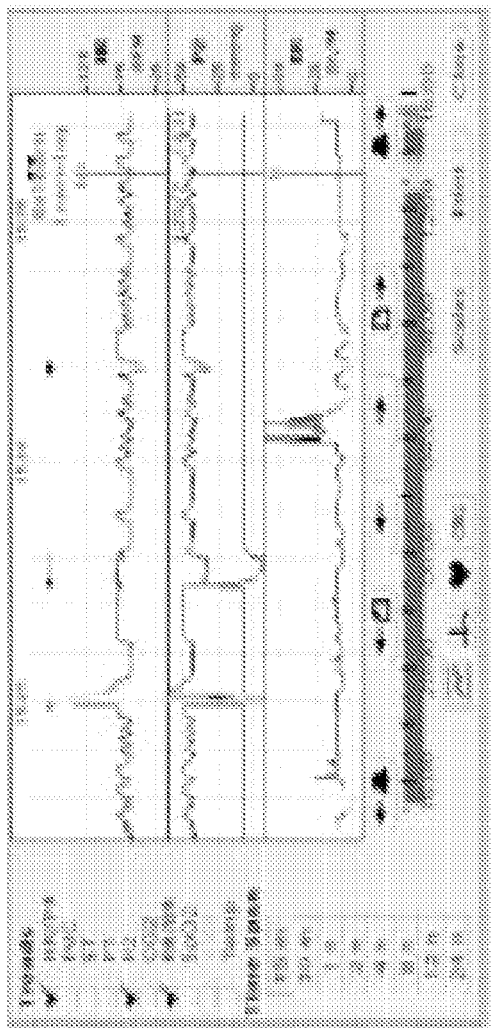

In one embodiment for professional users such as hospitals and nursing homes, a Central Monitoring Station provides alarm and vital sign oversight for a plurality of patients from a single computer workstation. FIG. 15E shows an exemplary multi-station vital parameter user interface for a professional embodiment, while FIG. 15F shows an exemplary trending pattern display. The clinician interface uses simple point and click actions with a computer mouse or trackball. The clinician can initiate or change monitoring functions from either the Central Station or the bedside monitor. One skilled in the art will recognize that patient data such as EKG data can be shown either by a scrolling waveform that moves along the screen display, or by a moving bar where the waveform is essentially stationary and the bar moves across the screen.

In one embodiment, software for the professional monitoring system provides a login screen to enter user name and password, together with database credentials. In Select Record function, the user can select a person, based on either entered or pre-selected criteria. From here navigate to their demographics, medical record, etc. The system can show a persons demographics, includes aliases, people involved in their care, friends and family, previous addresses, home and work locations, alternative numbers and custom fields. The system can show all data elements of a persons medical record. These data elements are not 'hard wired', but may be configured in the data dictionary to suit your particular requirements. It is possible to create views of the record that filter it to show (for instance) just the medications or diagnosis, etc. Any data element can be can be designated 'plan able' in the data dictionary and then scheduled. A Summary Report can be done. Example of a report displayed in simple format, selecting particular elements and dates. As many of these reports as required can be created, going across all data in the system based on some criteria, with a particular selection of fields and sorting, grouping and totaling criteria. Reports can be created that can format and analyze any data stored on the server. The system supports OLE controls and can include graphs, bar codes, etc. These can be previewed on screen, printed out or exported in a wide variety of formats. The system also maintains a directory of all organizations the administrator wishes to record as well as your own. These locations are then used to record the location for elements of the medical record (where applicable), work addresses for people involved in the care and for residential addresses for people in residential care. The data elements that form the medical record are not 'hard wired' (ie predefined) but may be customized by the users to suit current and future requirements.

In one embodiment, the wearable appliance can store patient data in its data storage device such as flash memory. The data can include Immunizations and dates; medications (prescriptions and supplements); physician names, addresses, phone numbers, email addresses; location and details of advance directives; insurance company, billing address, phone number, policy number; emergency contacts, addresses, home/business/pager phone numbers, email addresses. The data can include color or black and white photo of the wearer of the device; a thumb print, iris print of other distinguishing physical characteristic; dental records;

sample ECG or Cardiac Echo Scan; blood type; present medication being taken; drug interaction precautions; drug and/or allergic reaction precautions; a description of serious preexisting medical conditions; Emergency Medical Instructions, which could include: administering of certain suggested drugs or physical treatments; calling emergency physician numbers listed; bringing the patient to a certain type of clinic or facility based on religious beliefs; and living will instructions in the case of seriously ill patients; Organ Donor instructions; Living Will instructions which could include: instructions for life support or termination of treatment; notification of next of kin and/or friends including addresses and telephone numbers; ECG trace; Cardiac Echo Scan; EEG trace; diabetes test results; x-ray scans, among others. The wearable appliance stores the wearer's medical records and ID information. In one embodiment, to start the process new/original medical information is organized and edited to fit into the BWD page format either in physicians office or by a third party with access to a patient's medical records using the base unit storage and encrypting software which can be stored in a normal pc or other compatible computer device. The system can encrypt the records so as to be secure and confidential and only accessible to authorized individuals with compatible de-encrypting software. In the event the wearer is stricken with an emergency illness a Paramedic, EMT or Emergency Room Technician can use a wireless interrogator to rapidly retrieve and display the stored medical records in the wearable appliance and send the medical records via wireless telemetry to a remote emergency room or physicians office for rapid and life saving medical intervention in a crisis situation. In a Non-emergency Situation, the personal health information service is also helpful as it eliminates the hassle of repeatedly filling out forms when changing health plans or seeing a new physician; stores vaccination records to schools or organizations without calling the pediatrician; or enlists the doctor's or pharmacist's advice about multiple medications without carrying all the bottles to a personal visit.

In one embodiment, a plurality of body worn sensors with in-door positioning can be used as an Emergency Department and Urgent Care Center Tracking System. The system tracks time from triage to MD assessment, identifies patients that have not yet been registered, records room usage, average wait time, and average length of stay. The system allows user defined "activities" so that hospitals can track times and assist in improving patient flow and satisfaction. The system can set custom alerts and send email/pager notifications to better identify long patient wait times and record the number of these alert occurrences. The system can manage room usage by identifying those rooms which are under/over utilized. The hospital administrator can set manual or automatic alerts and generate custom reports for analysis of patient flow. The system maximizes revenue by streamlining processes and improving throughput; improves charge capture by ensuring compliance with regulatory standards; increases accountability by collecting clear, meaningful data; enhances risk management and QA; and decreases liability.

FIG. 16A shows ant exemplary process to continuously determine blood pressure of a patient. The process generates a blood pressure model of a patient (2002); determines a blood flow velocity using a piezoelectric transducer (2004); and provides the blood flow velocity to the blood pressure model to continuously estimate blood pressure (2006).

FIG. 16B shows another exemplary process to continuously determine blood pressure of a patient. First, during an initialization mode, a monitoring device and calibration device are attached to patient (2010). The monitoring device generates patient blood flow velocity, while actual blood pressure is measured by a calibration device (2012). Next, the process generates a blood pressure model based on the blood flow velocity and the actual blood pressure (2014). Once this is done, the calibration device can be removed (2016). Next, during an operation mode, the process periodically samples blood flow velocity from the monitoring device on a real-time basis (18) and provides the blood flow velocity as input information to the blood pressure model to estimate blood pressure (20). This process can be done in continuously or periodically as specified by a user.

In one embodiment, to determine blood flow velocity, acoustic pulses are generated and transmitted into the artery using an ultrasonic transducer positioned near a wrist artery. These pulses are reflected by various structures or entities within the artery (such as the artery walls, and the red blood cells within the subject's blood), and subsequently received as frequency shifts by the ultrasonic transducer. Next, the blood flow velocity is determined. In this process, the frequencies of those echoes reflected by blood cells within the blood flowing in the artery differ from that of the transmitted acoustic pulses due to the motion of the blood cells. This well known "Doppler shift" in frequency is used to calculate the blood flow velocity. In one embodiment for determining blood flow velocity, the Doppler frequency is used to determine mean blood velocity. For example, U.S. Pat. No. 6,514, 211, the content of which is incorporated by reference, discusses blood flow velocity using a time-frequency representation.

In one implementation, the system can obtain one or more numerical calibration curves describing the patient's vital signs such as blood pressure. The system can then direct energy such as infrared or ultrasound at the patient's artery and detecting reflections thereof to determine blood flow velocity from the detected reflections. The system can numerically fit or map the blood flow velocity to one or more calibration parameters describing a vital-sign value. The calibration parameters can then be compared with one or more numerical calibration curves to determine the blood pressure.

Additionally, the system can analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

In one embodiment, feed forward artificial neural networks (NNs) are used to classify valve-related heart disorders. The heart sounds are captured using the microphone or piezoelectric transducer. Relevant features were extracted using several signal processing tools, discrete wavelet transfer, fast fourier transform, and linear prediction coding. The heart beat sounds are processed to extract the necessary features by: a) denoising using wavelet analysis, b) separating one beat out of each record c) identifying each of the first heart sound (FHS) and the second heart sound (SHS). Valve problems are classified according to the time separation between the FHS and th SHS relative to cardiac cycle time, namely whether it is greater or smaller than 20% of cardiac cycle time. In one embodiment, the NN comprises 6 nodes at both ends, with one hidden layer containing 10 nodes. In another embodiment, linear predictive code (LPC) coefficients for each event were fed to two separate neural networks containing hidden neurons.

In another embodiment, a normalized energy spectrum of the sound data is obtained by applying a Fast Fourier Transform. The various spectral resolutions and frequency ranges were used as inputs into the NN to optimize these parameters to obtain the most favorable results.

In another embodiment, the heart sounds are denoised using six-stage wavelet decomposition, thresholding, and then reconstruction. Three feature extraction techniques were used: the Decimation method, and the wavelet method. Classification of the heart diseases is done using Hidden Markov Models (HMMs).

In yet another embodiment, a wavelet transform is applied to a window of two periods of heart sounds. Two analyses are realized for the signals in the window: segmentation of first and second heart sounds, and the extraction of the features. After segmentation, feature vectors are formed by using he wavelet detail coefficients at the sixth decomposition level. The best feature elements are analyzed by using dynamic programming.

In another embodiment, the wavelet decomposition and reconstruction method extract features from the heart sound recordings. An artificial neural network classification method classifies the heart sound signals into physiological and pathological murmurs. The heart sounds are segmented into four parts: the first heart sound, the systolic period, the second heart sound, and the diastolic period. The following features can be extracted and used in the classification algorithm: a) Peak intensity, peak timing, and the duration of the first heart sound b) the duration of the second heart sound c) peak intensity of the aortic component of S2(A2) and the pulmonic component of S2 (P2), the splitting interval and the reverse flag of A2 and P2, and the timing of A2 d) the duration, the three largest frequency components of the systolic signal and the shape of the envelope of systolic murmur e) the duration the three largest frequency components of the diastolic signal and the shape of the envelope of the diastolic murmur.

In one embodiment, the time intervals between the ECG R-waves are detected using an envelope detection process. The intervals between R and T waves are also determined. The Fourier transform is applied to the sound to detect S1 and S2. To expedite processing, the system applies Fourier transform to detect S1 in the interval 0.1-0.5 R-R. The system looks for S2 the intervals R-T and 0.6 R-R. S2 has an aortic component A2 and a pulmonary component P2. The interval between these two components and its changes with respiration has clinical significance. A2 sound occurs before P2, and the intensity of each component depends on the closing pressure and hence A2 is louder than P2. The third heard sound S3 results from the sudden halt in the movement of the ventricle in response to filling in early diastole after the AV valves and is normally observed in children and young adults. The fourth heart sound S4 is caused by the sudden halt of the ventricle in response to filling in presystole due to atrial contraction.

In yet another embodiment, the S2 is identified and a normalized splitting interval between A2 and P2 is determined. If there is no overlap, A2 and P2 are determined from the heart sound. When overlap exists between A2 and P2, the sound is dechirped for identification and extraction of A2 and P2 from S2. The A2-P2 splitting interval (SI) is calculated by computing the cross-correlation function between A2 and P2 and measuring the time of occurrence of its maximum amplitude. SI is then normalized (NSI) for heart rate as follows: NSI=SI/cardiac cycle time. The duration of the cardiac cycle can be the average interval of QRS waves of the ECG. It could also be estimated by computing the mean interval between a series of consecutive S1 and S2 from the heart sound data. A non linear regressive analysis maps the relationship between the normalized NSI and PAP. A mapping process such as a curve-fitting procedure determines the curve that provides the best fit with the patient data. Once the mathematical relationship is determined, NSI can be used to provide an accurate quantitative estimate of the systolic and mean PAP relatively independent of heart rate and systemic arterial pressure.

In another embodiment, the first heart sound (S1) is detected using a time-delayed neural network (TDNN). The network consists of a single hidden layer, with time-delayed links connecting the hidden units to the time-frequency energy coefficients of a Morlet wavelet decomposition of the input phonocardiogram (PCG) signal. The neural network operates on a 200 msec sliding window with each time-delay hidden unit spanning 100 msec of wavelet data.

In yet another embodiment, a local signal analysis is used with a classifier to detect, characterize, and interpret sounds corresponding to symptoms important for cardiac diagnosis. The system detects a plurality of different heart conditions. Heart sounds are automatically segmented into a segment of a single heart beat cycle. Each segment are then transformed using 7 level wavelet decomposition, based on Coifman 4th order wavelet kernel. The resulting vectors 4096 values, are reduced to 256 element feature vectors, this simplified the neural network and reduced noise.

In another embodiment, feature vectors are formed by using the wavelet detail and approximation coefficients at the second and sixth decomposition levels. The classification (decision making) is performed in 4 steps: segmentation of the first and second heart sounds, normalization process, feature extraction, and classification by the artificial neural network.

In another embodiment using decision trees, the system distinguishes (1) the Aortic Stenosis (AS) from the Mitral Regurgitation (MR) and (2) the Opening Snap (OS), the Second Heart Sound Split (A2_P2) and the Third Heart Sound (S3). The heart sound signals are processed to detect the first and second heart sounds in the following steps: a) wavelet decomposition, b) calculation of normalized average Shannon Energy, c) a morphological transform action that amplifies the sharp peaks and attenuates the broad ones d) a method that selects and recovers the peaks corresponding to S1 and S2 and rejects others e) algorithm that determines the boundaries of S1 and S2 in each heart cycle f) a method that distinguishes S1 from S2.

In one embodiment, once the heart sound signal has been digitized and captured into the memory, the digitized heart sound signal is parameterized into acoustic features by a feature extractor. The output of the feature extractor is delivered to a sound recognizer. The feature extractor can include the short time energy, the zero crossing rates, the level crossing rates, the filter-bank spectrum, the linear predictive coding (LPC), and the fractal method of analysis. In addition, vector quantization may be utilized in combination with any representation techniques. Further, one skilled in the art may use an auditory signal-processing model in place of the spectral models to enhance the system's robustness to noise and reverberation.

In one embodiment of the feature extractor, the digitized heart sound signal series $s(n)$ is put through a low-order filter, typically a first-order finite impulse response filter, to spectrally flatten the signal and to make the signal less susceptible to finite precision effects encountered later in the signal processing. The signal is pre-emphasized preferably using a fixed pre-emphasis network, or preemphasizer. The signal can also be passed through a slowly adaptive pre-emphasizer. The preemphasized heart sound signal is next presented to a frame blocker to be blocked into frames of N samples with adjacent frames being separated by M samples. In one implementation, frame 1 contains the first 400 samples. The frame 2 also contains 400 samples, but begins at the 300th sample and continues until the 700th sample. Because the adjacent frames overlap, the resulting LPC spectral analysis will be correlated from frame to frame. Each frame is windowed to minimize signal discontinuities at the beginning and end of each frame. The windower tapers the signal to zero at the beginning and end of each frame. Preferably, the window used for the autocorrelation method of LPC is the Hamming window. A noise canceller operates in conjunction with the autocorrelator to minimize noise. Noise in the heart sound pattern is estimated during quiet periods, and the temporally stationary noise sources are damped by means of spectral subtraction, where the autocorrelation of a clean heart sound signal is obtained by subtracting the autocorrelation of noise from that of corrupted heart sound. In the noise cancellation unit, if the energy of the current frame exceeds a reference threshold level, the heart is generating sound and the autocorrelation of coefficients representing noise is not updated. However, if the energy of the current frame is below the reference threshold level, the effect of noise on the correlation coefficients is subtracted off in the spectral domain. The result is half-wave rectified with proper threshold setting and then converted to the desired autocorrelation coefficients. The output of the autocorrelator and the noise canceller are presented to one or more parameterization units, including an LPC parameter unit, an FFT parameter unit, an auditory model parameter unit, a fractal parameter unit, or a wavelet parameter unit, among others. The LPC parameter is then converted into cepstral coefficients. The cepstral coefficients are the coefficients of the Fourier transform representation of the log magnitude spectrum. A filter bank spectral analysis, which uses the short-time Fourier transformation (STFT) may also be used alone or in conjunction with other parameter blocks. FFT is well known in the art of digital signal processing. Such a transform converts a time domain signal, measured as amplitude over time, into a frequency domain spectrum, which expresses the frequency content of the time domain signal as a number of different frequency bands. The FFT thus produces a vector of values corresponding to the energy amplitude in each of the frequency bands. The FFT converts the energy amplitude values into a logarithmic value which reduces subsequent computation since the logarithmic values are more simple to perform calculations on than the longer linear energy amplitude values produced by the FFT, while representing the same dynamic range. Ways for improving logarithmic conversions are well known in the art, one of the simplest being use of a look-up table. In addition, the FFT modifies its output to simplify computations based on the amplitude of a given frame. This modification is made by deriving an average value of the logarithms of the amplitudes for all bands. This average value is then subtracted from each of a predetermined group of logarithms, representative of a predetermined group of frequencies. The predetermined group consists of the logarithmic values, representing each of the frequency bands. Thus, utterances are converted from acoustic data to a sequence of vectors of k dimensions, each sequence of vectors identified as an acoustic frame, each frame represents a portion of the utterance. Alternatively, auditory modeling parameter unit can be used alone or in conjunction with others to improve the parameterization of heart sound signals in noisy and reverberant environments. In this approach, the filtering section may be represented by a plurality of filters equally spaced on a log-frequency scale from 0 Hz to about 3000 Hz and having a prescribed response corresponding to the cochlea. The nerve fiber firing mechanism is simulated by a multilevel crossing detector at the output of each cochlear filter. The ensemble of the multilevel crossing intervals corresponding to the firing activity at the auditory nerve fiber-array. The interval between each successive pair of same direction, either positive or negative going, crossings of each predetermined sound intensity level is determined and a count of the inverse of these interspike intervals of the multilevel detectors for each spectral portion is stored as a function of frequency. The resulting histogram of the ensemble of inverse interspike intervals forms a spectral pattern that is representative of the spectral distribution of the auditory neural response to the input sound and is relatively insensitive to noise The use of a plurality of logarithmically related sound intensity levels accounts for the intensity of the input signal in a particular frequency range. Thus, a signal of a particular frequency having high intensity peaks results in a much larger count for that frequency than a low intensity signal of the same frequency. The multiple level histograms of the type described herein readily indicate the intensity levels of the nerve firing spectral distribution and cancel noise effects in the individual intensity level histograms. Alternatively, the fractal parameter block can further be used alone or in conjunction with others to represent spectral information. Fractals have the property of self similarity as the spatial scale is changed over many orders of magnitude. A fractal function includes both the basic form inherent in a shape and the statistical or random properties of the replacement of that shape in space. As is known in the art, a fractal generator employs mathematical operations known as local affine transformations. These transformations are employed in the process of encoding digital data representing spectral data. The encoded output constitutes a "fractal transform" of the spectral data and consists of coefficients of the affine transformations. Different fractal transforms correspond to different images or sounds.

Alternatively, a wavelet parameterization block can be used alone or in conjunction with others to generate the parameters. Like the FFT, the discrete wavelet transform (DWT) can be viewed as a rotation in function space, from the input space, or time domain, to a different domain. The DWT consists of applying a wavelet coefficient matrix hierarchically, first to the full data vector of length N, then to a smooth vector of length N/2, then to the smooth-smooth vector of length N/4, and so on. Most of the usefulness of wavelets rests on the fact that wavelet transforms can usefully be severely truncated, or turned into sparse expansions. In the DWT parameterization block, the wavelet transform of the heart sound signal is performed. The wavelet coefficients are allocated in a non-uniform, optimized manner. In general, large wavelet coefficients are quantized accurately, while small coefficients are quantized coarsely or even truncated completely to achieve the parameterization. Due to the sensitivity of the low-order cepstral coefficients to the overall spectral slope and the sensitivity of the high-order cepstral coefficients to noise variations, the parameters generated may be weighted by a parameter weighing block, which is a tapered window, so as to minimize these sensitivities. Next, a temporal derivator measures the dynamic changes in the spectra. Power features are also generated to enable the system to distinguish heart sound from silence.

After the feature extraction has been performed, the heart sound parameters are next assembled into a multidimensional vector and a large collection of such feature signal vectors can be used to generate a much smaller set of vector quantized (VQ) feature signals by a vector quantizer that cover the range of the larger collection. In addition to reducing the storage space, the VQ representation simplifies the computation for determining the similarity of spectral analysis vectors and reduces the similarity computation to a look-up table of similarities between pairs of codebook vectors. To reduce the quantization error and to increase the dynamic range and the precision of the vector quantizer, the preferred embodiment partitions the feature parameters into separate codebooks, preferably three. In the preferred embodiment, the first, second and third codebooks correspond to the cepstral coefficients, the differenced cepstral coefficients, and the differenced power coefficients.

With conventional vector quantization, an input vector is represented by the codeword closest to the input vector in terms of distortion. In conventional set theory, an object either belongs to or does not belong to a set. This is in contrast to fuzzy sets where the membership of an object to a set is not so clearly defined so that the object can be a part member of a set. Data are assigned to fuzzy sets based upon the degree of membership therein, which ranges from 0 (no membership) to 1.0 (full membership). A fuzzy set theory uses membership functions to determine the fuzzy set or sets to which a particular data value belongs and its degree of membership therein.

To handle the variance of heart sound patterns of individuals over time and to perform speaker adaptation in an automatic, self-organizing manner, an adaptive clustering technique called hierarchical spectral clustering is used. Such speaker changes can result from temporary or permanent changes in vocal tract characteristics or from environmental effects. Thus, the codebook performance is improved by collecting heart sound patterns over a long period of time to account for natural variations in speaker behavior. In one embodiment, data from the vector quantizer is presented to one or more recognition models, including an HMM model, a dynamic time warping model, a neural network, a fuzzy logic, or a template matcher, among others. These models may be used singly or in combination.

In dynamic processing, at the time of recognition, dynamic programming slides, or expands and contracts, an operating region, or window, relative to the frames of heart sound so as to align those frames with the node models of each S1-S4 pattern to find a relatively optimal time alignment between those frames and those nodes. The dynamic processing in effect calculates the probability that a given sequence of frames matches a given word model as a function of how well each such frame matches the node model with which it has been time-aligned. The word model which has the highest probability score is selected as corresponding to the heart sound.

Dynamic programming obtains a relatively optimal time alignment between the heart sound to be recognized and the nodes of each word model, which compensates for the unavoidable differences in speaking rates which occur in different utterances of the same word. In addition, since dynamic programming scores words as a function of the fit between word models and the heart sound over many frames, it usually gives the correct word the best score, even if the word has been slightly misspoken or obscured by background sound. This is important, because humans often mispronounce words either by deleting or mispronouncing proper sounds, or by inserting sounds which do not belong.

In dynamic time warping (DTW), the input heart sound A, defined as the sampled time values $A=a(1) \ldots a(n)$, and the vocabulary candidate B, defined as the sampled time values $B=b(1) \ldots b(n)$, are matched up to minimize the discrepancy in each matched pair of samples. Computing the warping function can be viewed as the process of finding the minimum cost path from the beginning to the end of the words, where the cost is a function of the discrepancy between the corresponding points of the two words to be compared. Dynamic programming considers all possible points within the permitted domain for each value of i. Because the best path from the current point to the next point is independent of what happens beyond that point. Thus, the total cost of $[i(k), j(k)]$ is the cost of the point itself plus the cost of the minimum path to it. Preferably, the values of the predecessors can be kept in an M×N array, and the accumulated cost kept in a 2.times.N array to contain the accumulated costs of the immediately preceding column and the current column. However, this method requires significant computing resources. For the heart sound recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of heart sound against a given word model if the partial probability score for that comparison drops below a given threshold. This greatly reduces computation, since the dynamic programming of a given portion of heart sound against most words produces poor dynamic programming scores rather quickly, enabling most words to be pruned after only a small percent of their comparison has been performed. To reduce the computations involved, one embodiment limits the search to that within a legal path of the warping.

A Hidden Markov model can be used in one embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j)(O(t)]$, where the $b(j)(O(t))$ term of the output symbol matrix is the probability of outputting observation $O(t)$, given that the model is in state j. The first state is always constrained to be the initial state for the first time frame of the utterance, as only a prescribed set of left-to-right state transitions are possible. A predetermined final state is defined from which transitions to other states cannot occur. Transitions are restricted to reentry of a state or entry to one of the next two states. Such transitions are defined in the model as transition probabilities. For example, a heart sound pattern currently having a frame of feature signals in state 2 has a probability of reentering state 2 of $a(2,2)$, a probability $a(2,3)$ of entering state 3 and a probability of $a(2,4)=1-a(2,1)-a(2,2)$ of entering state 4. The probability $a(2,1)$ of entering state 1 or the probability $a(2,5)$ of entering state 5 is zero and the sum of the probabilities $a(2,1)$ through $a(2,5)$ is one. Although the preferred embodiment restricts the flow graphs to the present state or to the next two states, one skilled in the art can build an HMM model without any transition restrictions.

The Markov model is formed for a reference pattern from a plurality of sequences of training patterns and the output symbol probabilities are multivariate Gaussian function probability densities. The heart sound traverses through the feature extractor. During learning, the resulting feature vector series is processed by a parameter estimator, whose output is provided to the hidden Markov model. The hidden Markov model is used to derive a set of reference pattern templates, each template representative of an identified S1-S4 pattern in a vocabulary set of reference patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator.

One exemplary data flows between a user with a cell phone or mobile device in an interactive conversation with third party devices or doctors is discussed next. A patient is first registered with the system. After the user enrolls, the system starts communicating with the patient by sending the patient one or more instructions and/or reminders. Using a computer such as a mobile device the user communicates with the physician communicator engine and receives in return a custom response. At the same time, and depending on selected rules triggered by the patient response, the system sends notifications to third-party devices such as devices owned by family members or caregivers. The system can also send notifications to doctors, doctor's staff, or other authorized service providers who then send in response results that are automatically processed by the system to alter the behavior of some rules.

Figure 17A:
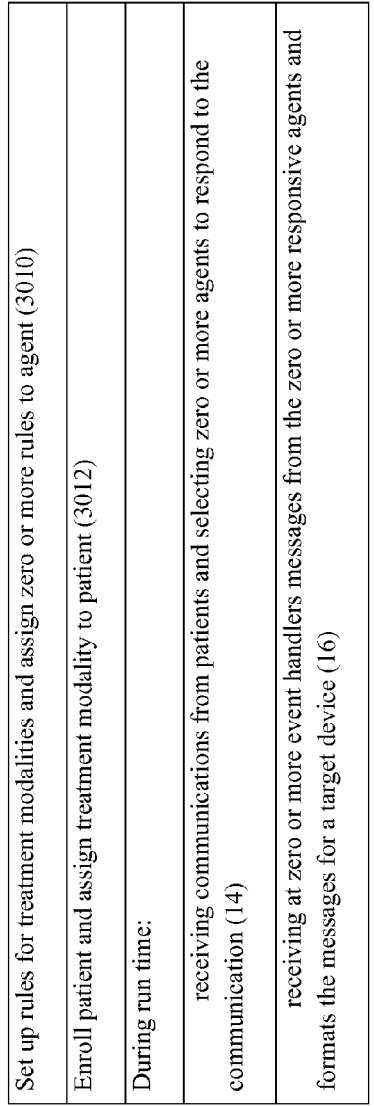
FIG. 17A shows an exemplary process for automated interactive communication between clinicians and patients.

FIG. 17A shows an exemplary process for automated interactive communication between clinicians and patients. The process includes code to:

Set up rules for treatment modalities and assign zero or more rules to agent (3010)

Enroll patient and assign treatment modality to patient (3012)

During run time:

receiving communications from patients and selecting zero or more agents to respond to the communication (3014)

receiving at zero or more event handlers messages from the zero or more responsive agents and formats the messages for a target device (3016)

Figure 17C:
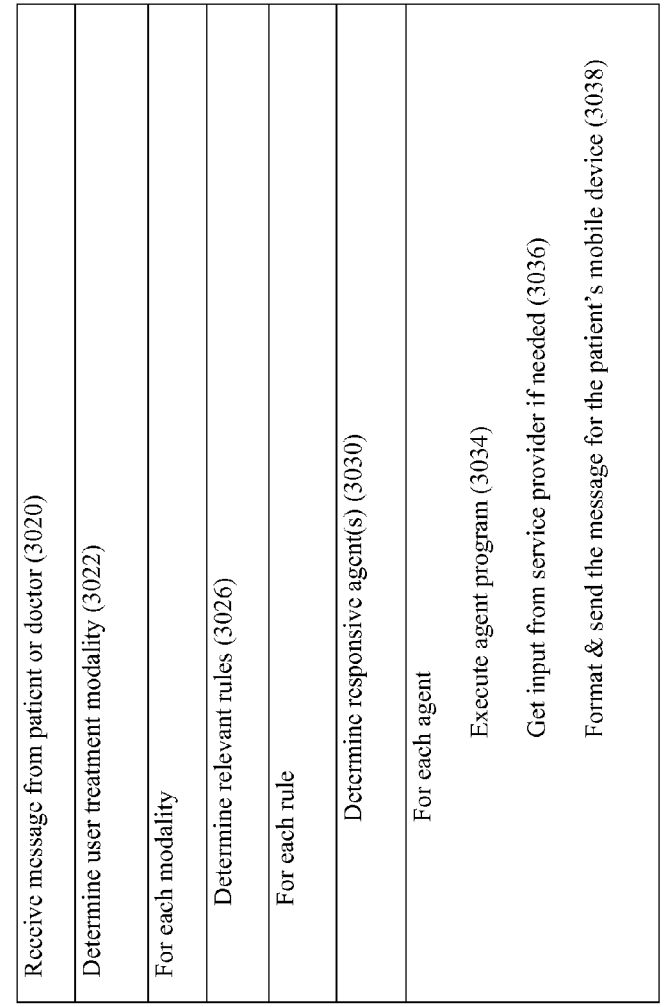
FIG. 17C shows in more details the event handler of FIG. 17A.
Figure 17B:
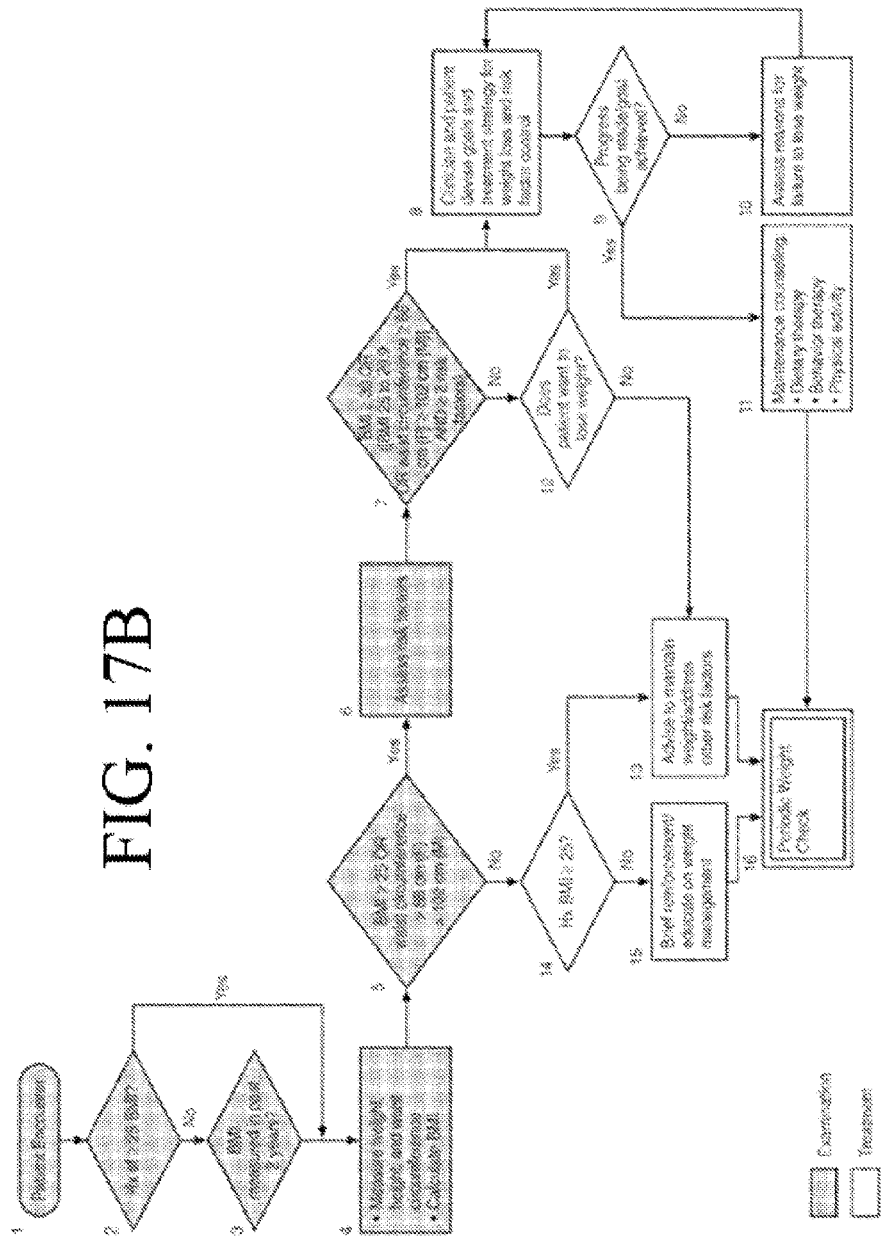
FIG. 17B shows one exemplary weight loss treatment algorithm using the process of FIG. 17A.

FIG. 17B shows an exemplary process for applying the agents of FIG. 17A to a weight loss treatment scenario. The general goals of weight loss and management are: (1) at a minimum, to prevent further weight gain; (2) to reduce body weight; and (3) to maintain a lower body weight over the long term. The initial goal of weight loss therapy is to reduce body weight by approximately 10 percent from baseline. If this goal is achieved, further weight loss can be attempted, if indicated through further evaluation. A reasonable time line for a 10 percent reduction in body weight is 6 months of therapy. For overweight patients with BMIs in the typical range of 27 to 35, a decrease of 300 to 500 kcal/day will result in weight losses of about ½ to 1 lb/week and a 10 percent loss in 6 months. For more severely obese patients with BMIs >35, deficits of up to 500 to 1,000 kcal/day will lead to weight losses of about 1 to 2 lb/week and a 10 percent weight loss in 6 months. Weight loss at the rate of 1 to 2 lb/week (calorie deficit of 500 to 1,000 kcal/day) commonly occurs for up to 6 months. After 6 months, the rate of weight loss usually declines and weight plateaus because of a lesser energy expenditure at the lower weight.

After 6 months of weight loss treatment, efforts to maintain weight loss should be put in place. If more weight loss is needed, another attempt at weight reduction can be made. This will require further adjustment of the diet and physical activity prescriptions.

Dietary Therapy: A diet that is individually planned and takes into account the patient's overweight status in order to help create a deficit of 500 to 1,000 kcal/day should be an integral part of any weight loss program. Depending on the patient's risk status, the low-calorie diet (LCD) recommended should be consistent with the NCEP's Step I or Step II Diet. Besides decreasing saturated fat, total fats should be 30 percent or less of total calories. Reducing the percentage of dietary fat alone will not produce weight loss unless total calories are also reduced. Isocaloric replacement of fat with carbohydrates will reduce the percentage of calories from fat but will not cause weight loss. Reducing dietary fat, along with reducing dietary carbohydrates, usually will be needed to produce the caloric deficit needed for an acceptable weight loss. When fat intake is reduced, priority should be given to reducing saturated fat to enhance lowering of LDL-cholesterol levels. Frequent contacts with the practitioner during dietary therapy help to promote weight loss and weight maintenance at a lower weight.

An increase in physical activity is an important component of weight loss therapy, although it will not lead to substantially greater weight loss over 6 months. Most weight loss occurs because of decreased caloric intake. Sustained physical activity is most helpful in the prevention of weight regain. In addition, it has a benefit in reducing cardiovascular and diabetes risks beyond that produced by weight reduction alone. For most obese patients, exercise should be initiated slowly, and the intensity should be increased gradually. The exercise can be done all at one time or intermittently over the day. Initial activities may be walking or swimming at a slow pace. The patient can start by walking 30 minutes for 3 days a week and can build to 45 minutes of more intense walking at least 5 days a week. With this regimen, an additional expenditure of 100 to 200 calories per day can be achieved. All adults should set a long-term goal to accumulate at least 30 minutes or more of moderate-intensity physical activity on most, and preferably all, days of the week. This regimen can be adapted to other forms of physical activity, but walking is particularly attractive because of its safety and accessibility. Patients should be encouraged to increase "every day" activities such as taking the stairs instead of the elevator. With time, depending on progress and functional capacity, the patient may engage in more strenuous activities. Competitive sports, such as tennis and volleyball, can provide an enjoyable form of exercise for many, but care must be taken to avoid injury. Reducing sedentary time is another strategy to increase activity by undertaking frequent, less strenuous activities.

The communication system of FIG. 1A is used to provide Behavior Therapy. The system automatically sends messages using rule-based agents to communicate with patients. The agents can use learning principles such as reinforcement provide tools for overcoming barriers to compliance with dietary therapy and/or increased physical activity to help patient in achieving weight loss and weight maintenance. Specific communication message include self-monitoring of both eating habits and physical activity, stress management, stimulus control, problem solving, contingency management, cognitive restructuring, and social support through the social network system.

Pharmacotherapy can be used if behavior therapy does not work. In carefully selected patients, appropriate drugs can augment LCDs, physical activity, and behavior therapy in weight loss. Drugs such as sibutramine and orlistat can be used as long as potential side effects with drugs are considered. With sibutramine, increases in blood pressure and heart rate may occur. Sibutramine should not be used in patients with a history of hypertension, CHD, congestive heart failure, arrhythmias, or history of stroke. With orlistat, fat soluble vitamins may require replacement because of partial malabsorption. Weight loss surgery is one option for weight reduction in a limited number of patients with clinically severe obesity, i.e., BMIs >=40 or >=35 with comorbid conditions. Weight loss surgery should be reserved for patients in whom efforts at medical therapy have failed and who are suffering from the complications of extreme obesity. Gastrointestinal surgery (gastric restriction [vertical gastric banding] or gastric bypass is an intervention weight loss option for motivated subjects with acceptable operative risks. An integrated program must be in place to provide guidance on diet, physical activity, and behavioral and social support both prior to and after the surgery.

The agents are adaptive to the patient and allow for program modifications based on patient responses and preferences. For example, the agent can be modified for weight reduction after age 65 to address risks associated with obesity treatment that are unique to older adults or those who smoke.

FIG. 17C shows in more details the event handler of FIG. 17A. The process includes code to:
Receive message from patient or doctor (3020)
Determine user treatment modality (3022)
For each modality
Determine relevant rules (3026)
For each rule
  Determine responsive agent(s) (3030)
  For each agent
    Execute agent program (3034)
    Get input from service provider if needed (3036)
    Format & send the message for the patient's mobile device (3038)

The system processes a communication from a patient according to one or more treatment scenarios. Each treatment scenario is composed of one or more rules to be processed in a sequence that can be altered when invoking certain agents.

The if-then rules can be described to the system using a graphical user interface that runs on a web site, a computer, or a mobile device, and the resulting rules are then processed by a rules engine. In one embodiment, the if-then rules are entered as a series of dropdown selectors whose possible values are automatically determined and populated for user selection to assist user in accurately specifying the rules.

In one embodiment, the rules engine is Jess, which is a rule engine and scripting environment written entirely in Sun's Java language by Ernest Friedman-Hill at Sandia National Laboratories in Livermore, Calif. and downloadable at http://www.jessrules.com/jess/index.shtml. With Jess, the system can "reason" using knowledge supplied in the form of declarative rules. Jess is small, light, and one of the fastest rule engines available. Jess uses an enhanced version of the Rete algorithm to process rules. Rete is a very efficient mechanism for solving the difficult many-to-many matching problem (see for example "Rete: A Fast Algorithm for the Many Pattern/Many Object Pattern Match Problem", Charles L. Forgy, Artificial Intelligence 19 (1982), 17-37.) Jess has many unique features including backwards chaining and working memory queries, and of course Jess can directly manipulate and reason about Java objects. Jess is also a powerful Java scripting environment, from which Java objects, call Java methods, can implement Java interfaces without compiling any Java code.

The user can dynamically create an if/then/else statement. A dropdown selector can be used to select a column, then a dropdown to select the conditional operator (=, >, <, !=, among others) and then a text box in which to enter a column, text or number value. The system can add multiple conditions. The rules can be saved as serialized object in a database. After entering parameter values, a new set of rules can be generated and inserted within the current active scenario. The corresponding rules can then be modified directly by accessing the individual agents within the rules.

In one embodiment, the agent can be self-modifying. The agent receives parameters from its callers. The agent in turn executes one or more functions. It can include an adaptive self-modifying function, and the third-party extension interfaces. The adaptive self-modifying function is capable of modifying the agent parameters and/or the agent function at run time, thereby changing the behavior of the agent.

FIG. 17D shows an exemplary modality of the rules engine to serve obese patients that the doctor can review and approve. In this scenario, the engine executes 3 master agents:
Run blood pressure master agent (3050)
Run diabetic master agent (3052)
Run weight loss agent (3054).

The blood pressure master agent in turn invokes the following agents:
If blood pressure is between 130-139/85-89 mm Hg then run agent high_blood_pressure
If blood pressure is between 140-159/90-99 mm Hg then run agent stage1_blood_pressure
If blood pressure is above 159/99 mm Hg then run agent drug_treatment_for_blood_pressure For the above example, high normal blood pressure of between 130-139/85-89 mm Hg is included in the risk stratification. In patients with high normal blood pressure with no or only one concurrent risk factor that does not include diabetes, target organ, or clinical cardiac disease, the agent high_blood_pressure suggests to the patient to use lifestyle modification to lower blood pressure. Lifestyle modification includes changes to the patient's dieting and exercising habits. With a risk factor of target organ or clinical cardiac disease, diabetes and/or other risk factors, the agent can recommend drug therapy, no matter what the patient's blood pressure is. The agent for patients with stage 1 blood pressures of between 140-159/90-99 mm Hg who have no other risk factors will suggest the patient try lifestyle modifications for a year before drug therapy is used. But if these patients have one risk factor other than diabetes, target organ, or clinical cardiac disease, their lifestyle modification should be tried for only 6 months before initiation therapy. For patients with blood pressure above 150/100 mm Hg, the agent reminds the patient to have drug therapy in addition to lifestyle modifications.

The diabetic master agent in turn invokes the following agents:
Monitoring agent: Make sure doctor orders the key tests at the right times.
Dieting planning agent: Work with a dietitian to develop a great eating plan.
Glucose Testing Agent: Check blood glucose at correct intervals.
Exercise agent: Monitor exercise to help heart.
Medication compliance agent: check that insulin is taken at correct time.
Foot care agent: Check your feet with your eyes daily.
Eye care agent: remind patient to get periodic eye exam.

The weight loss agent considers the patient's BMI, waist circumference, and overall risk status including the patient's motivation to lose weight. The weight loss agent in turn calls the following agents:
Body Mass Index agent: The BMI, which describes relative weight for height, is significantly correlated with total body fat content. The BMI should be used to assess overweight and obesity and to monitor changes in body weight. In addition, measurements of body weight alone can be used to determine efficacy of weight loss therapy. BMI is calculated as weight (kg)/height squared (m2). To estimate BMI using pounds and inches, use: [weight (pounds)/height (inches)2]×703. Weight classifications by BMI, selected for use in this report, are shown below:

| CLASSIFICATION OF OVERWEIGHT AND OBESITY BY BMI | | |
|---|---|---|
| | Obesity Class | BMI (kg/m$^2$) |
| Underweight | | <18.5 |
| Normal | | 18.5-24.9 |
| Overweight | | 25.0-29.9 |
| Obesity | I | 30.0-34.9 |
| | II | 35.0-39.9 |
| Extreme Obesity | III | ≥40 |

A conversion table of heights and weights resulting in selected BMI units is

| SELECTED BMI UNITS CATEGORIZED BY INCHES (CM) AND POUNDS (KG). | | | |
|---|---|---|---|
| Height in inches (cm) | BMI 25 kg/m$^2$ | BMI 27 kg/m$^2$ | BMI 30 kg/m$^2$ |
| | Body weight in pounds (kg) | | |
| 58 (147.32) | 119 (53.98) | 129 (58.51) | 143 (64.86) |
| 59 (149.86) | 124 (56.25) | 133 (60.33) | 148 (67.13) |
| 60 (152.40) | 128 (58.06) | 138 (62.60) | 153 (69.40) |
| 61 (154.94) | 132 (59.87) | 143 (64.86) | 158 (71.67) |
| 62 (157.48) | 136 (61.69) | 147 (66.68) | 164 (74.39) |
| 63 (160.02) | 141 (63.96) | 152 (68.95) | 169 (76.66) |
| 64 (162.56) | 145 (65.77) | 157 (71.22) | 174 (78.93) |
| 65 (165.10) | 150 (68.04) | 162 (73.48) | 180 (81.65) |
| 66 (167.64) | 155 (70.31) | 167 (75.75) | 186 (84.37) |
| 67 (170.18) | 159 (72.12) | 172 (78.02) | 191 (86.64) |
| 68 (172.72) | 164 (74.39) | 177 (80.29) | 197 (89.36) |
| 69 (175.26) | 169 (76.66) | 182 (82.56) | 203 (92.08) |
| 70 (177.80) | 174 (78.93) | 188 (85.28) | 207 (93.90) |
| 71 (180.34) | 179 (81.19) | 193 (87.54) | 215 (97.52) |
| 72 (182.88) | 184 (83.46) | 199 (90.27) | 221 (100.25) |
| 73 (185.42) | 189 (85.73) | 204 (92.53) | 227 (102.97) |
| 74 (187.96) | 194 (88.00) | 210 (95.26) | 233 (105.69) |
| 75 (190.50) | 200 (90.72) | 216 (97.98) | 240 (108.86) |
| 76 (193.04) | 205 (92.99) | 221 (100.25) | 246 (111.59) |

Metric conversion formula = weight (kg)/height (m)$^2$
Example of BMI calculation:
A person who weighs 78.93 kilograms and is 177 centimeters tall has a BMI of 25.
weight (78.93 kg)/height (1.77 m)$^2$ = 25

Non-metric conversion formula = [weight (pounds)/height (inches)$^2$] × 704.5
Example of BMI calculation:
A person who weighs 164 pounds and is 68 inches (or 5' 8") tall has a BMI of 25.
[weight (164 pounds)/height (68 inches)$^2$] × 704.5 = 25

Waist Circumference agent: The presence of excess fat in the abdomen out of proportion to total body fat is an independent predictor of risk factors and morbidity. Waist circumference is positively correlated with abdominal fat content. It provides a clinically acceptable measurement for assessing a patient's abdominal fat content before and during weight loss treatment. The sex-specific cutoffs noted on the next page can be used to identify increased relative risk for the development of obesity-associated risk factors in most adults with a BMI of 25 to 34.9 kg/m2: These waist circumference cutpoints lose their incremental predictive power in patients with a BMI >=35 kg/m2 because these patients will exceed the cutpoints noted above. The disease risk of increased abdominal fat to the disease risk of BMI is as follows:

| CLASSIFICATION OF OVERWEIGHT AND OBESITY BY BMI, WAIST CIRCUMFERENCE AND ASSOCIATED DISEASE RISKS | | | | |
|---|---|---|---|---|
| | | | Disease Risk[+] Relative to Normal Weight and Waist Circumference | |
| | BMI (kg/m$^2$) | Obesity Class | Men ≤102 cm (≤40 in) Women ≤88 cm (≤35 in) | >102 cm (>40 in) >88 cm (>35 in) |
| Underweight | <18.5 | | — | — |
| Normal | 18.5-24.9 | | — | — |
| Overweight | 25.0-29.9 | | Increased | High |
| Obesity | 30.0-34.9 | I | High | Very High |
| | 35.0-39.9 | II | Very High | Very High |
| Extreme Obesity | ≥40 | III | Extremely High | Extremely High |

These categories denote relative risk, not absolute risk; that is, relative to risk at normal weight. They should not be equated with absolute risk, which is determined by a summation of risk factors. They relate to the need to institute weight loss therapy and do not directly define the required intensity of modification of risk factors associated with obesity.

Risk Status agent is used for assessment of a patient's absolute risk status and in turn uses the following agents:
1) Disease condition agent: determine existence of coronary heart disease (CHD), other atherosclerotic diseases, type 2 diabetes, and sleep apnea.
2) Obesity-associated disease agent: determines gynecological abnormalities, osteoarthritis, gallstones and their complications, and stress incontinence.
3) Cardiovascular risk factors agent: cigarette smoking, hypertension (systolic blood pressure >=140 mm Hg or diastolic blood pressure >=90 mm Hg, or the patient is taking antihypertensive agents), high-risk LDL-cholesterol (>=160 mg/dL), low HDL-cholesterol (<35 mg/dL), impaired fasting glucose (fasting plasma glucose of 110 to 125 mg/dL), family history of premature CHD (definite myocardial infarction or sudden death at or before 55 years of age in father or other male first-degree relative, or at or before 65 years of age in mother or other female first-degree relative), and age (men >=45 years and women >=55 years or postmenopausal). Patients can be classified as being at high absolute risk if they have three of the aforementioned risk factors. Patients at high absolute risk usually require clinical management of risk factors to reduce risk. Patients who are overweight or obese often have other cardiovascular risk factors. Methods for estimating absolute risk status for developing cardiovascular disease based on these risk factors are described in detail in the National Cholesterol Education Program's Second Report of the Expert Panel on the Detection, Evaluation, and Treatment of High Blood Cholesterol in Adults (NCEP's ATP II) and the Sixth Report of the Joint National Committee on Prevention, Detection, Evaluation, and Treatment of High Blood Pressure (JNC VI). The intensity of intervention for cholesterol disorders or hypertension is adjusted according to the absolute risk status estimated from multiple risk correlates. These include both the risk factors listed above and evidence of end-organ damage present in hypertensive patients. Approaches to therapy for cholesterol disorders and hypertension are described in ATP II and JNC VI, respectively. In overweight patients, control of cardiovascular risk factors deserves equal emphasis as weight reduction therapy. Reduction of risk factors will reduce the risk for cardiovascular disease whether or not efforts at weight loss are successful.

Other risk factors can be considered as rules by the agent, including physical inactivity and high serum triglycerides (>200 mg/dL). When these factors are present, patients can be considered to have incremental absolute risk above that estimated from the preceding risk factors. Quantitative risk contribution is not available for these risk factors, but their presence heightens the need for weight reduction in obese persons.

A patient motivation agent evaluates the following factors: reasons and motivation for weight reduction; previous history of successful and unsuccessful weight loss attempts; family, friends, and work-site support; the patient's understanding of the causes of obesity and how obesity contributes to several diseases; attitude toward physical activity; capacity to engage in physical activity; time availability for weight loss intervention; and financial considerations. In addition to considering these issues, the system can heighten a patient's motivation for weight loss and prepare the patient for treatment through normative messaging and warnings. This can be done by enumerating the dangers accompanying persistent obesity and by describing the strategy for clinically assisted weight reduction. Reviewing the patients' past attempts at weight loss and explaining how the new treatment plan will be different can encourage patients and provide hope for successful weight loss.

The agents facilitate the interaction between doctors and patients using devices such as smartphones, tablets, and emerging wearable devices, for the creation of new, powerful, easy-to-use solutions in healthcare. It is particularly well suited for applications using popular and emerging user and machine-to-machine interaction technologies such as instant messaging, emails, SMS, near field communications (NFC), and M2M.

FIG. 18A shows another exemplary process for monitoring a patient with the agents. The process starts with patient registration (3100) and collection of information on patient (3102). Next, the process selects a treatment template based on treatment plan for similar patients (3104). The process generates a treatment plan from the template and customizes the treatment plan (3006). The system considers the following factors: medical condition, amount of weight to lose, physician observations regarding mental state of the patient.

In the event the patient has extensive or contraindicating medical history or information, the system alerts the doctor to manually review the patient file and only generate recommendations with authorization from a doctor.

The doctor subsequently reviews and discusses the customized plan with the patient. In one embodiment, during the discussion, the doctor offers the patient the opportunity to enroll in the automated monitoring program. For a monthly or yearly fee, the system would provide the patient with periodic encouragements or comments from the system or the physician. In one embodiment, the doctor can provide the patient with an optional monitoring hardware that measures patient activity (such as accelerometers) and/or vital signs (such as EKG amplifiers).

Upon user enrollment, the system's workflow helps the doctor with setting goals with the patient, establishing a bond of trust and loyalty, and providing positive feedback for improving compliance. Loyalty to the practitioner initially produces higher compliance, emphasizing that establishing a close relationship helps. By providing rapid feedback through instant messaging or emails, the system helps doctors earn the patient's respect and trust, set goals together with the patient, and praise progress when it occurs.

Once enrolled, the system collects data on patient compliance with a treatment plan (3008). This can be done using mobile devices with sensors such as MEMS devices including accelerometer and others as described more fully below. Alternatively, the system periodically requests patient data will be weighed, measured, body fat calculated, blood pressure, resting heart rate and overall well-being. In one embodiment, the system provides a daily (7 days a week) counseling process using texting, email or social network communications.

The process also accumulates reward points for patient to encourage healthy activities, such as jogging, walking, or gardening (3110). The process also compares patient progress with other patients (3112) and sends automatic encouraging messages to patients (3114). Upon patient authorization, the system announces the patient's goals and progress to a social network such as Facebook. The social network strengthens the patient's will for dieting and exercise by the "extent to which individuals perceive that significant others encourage choice and participation in decision-making, provide a meaningful rationale, minimize pressure, and acknowledge the individual's feelings and perspectives." The system supplements the treatment through social supports at home and encourages the patient to make their family and close friends aware of their condition and the expectations of diet and exercise. This will provide the patient with encouragement and accountability.

Periodically, the system shows patient status to doctor (3016) and presents recommendations to doctor on preventive steps, such as check-ups and basic blood tests (3018). Automatically, the system schedules in person consultation for patient and doctor (3020). Captured progress data can be viewed by the physicians and patients using a web based system. The physician can review all interactions between the system and the patient. The physician is able to see their progress reports, interactive e mail which includes daily menus and notes between the service and the patient. The physician will be able to check on the patient's progress at any time of day or night. The system improves the Doctor-Patient relationship and influences compliance.

The system's interactive behavior combines four key elements: just-in-time information, automation in checking with patients, persuasive techniques or messaging, and user control elements. In one embodiment, reports about the user's calorie consumption and exercise activity over time, and in comparison to similarly situated people, are generated.

The system provides meaningful feedback, allowing customers to "see" their food consumption, exercise and the impact of changes. When calories from eating go up between months, a graph depicts so and by how much. Without the system's report to conveniently compare food consumption and exercise from one week to the next, it would be much harder to track those changes. Feedback provides the information crucial to bring about self-awareness of one's actions.

Additionally, the greater value of the system is that it provides useful information about what other similar users' actions and impacts are like. The report shows where the patient's energy intake and outtake are in comparison to the healthiest and the average person. This information serves as a descriptive norm, letting customers know where they are in the spectrum of average and healthy people. When customers see that they are below or even just above average, they want to move "up" on the exercise but reduce their calorie intake. As humans, users are programmed to want to be unique . . . but not too unique—they want to have "normal" food consumption and normal health.

With regard to the message persuasiveness, content is positive and targeted to the user's specific situation. The system provides action opportunities with its reports. If the user is mildly overweight, it might offer a suggestion of having salad with a low calorie dressing for dinner. One embodiment provides a "marketplace" concept, which means that the suggestion would be accompanied by, say, a coupon for salad at a local restaurant. In one embodiment, the system has prior relationships with partners such as restaurants that would offer meals with preset calorie and can send the user coupons to different partners on different days, thus providing users with a wide range of healthy food selections. The system's power lies in its ability to simultaneously prep individuals for action and give them an easy opportunity to do so.

In sum, the system's feedback is effective because:
It is provided frequently, as soon after the consumption behavior as possible.
It is clearly and simply presented.
It is customized to the patient's specific medical condition.
It is provided relative to a meaningful standard of comparison.
It is provided over an extended period of time.
It includes specific food consumption and calorie breakdown.
It is interactive through instant messaging, email, or social networks.

In one embodiment, body analysis data is determined from enrollment data, and include: body mass ratio, pounds of lean muscle mass, percentage of body fat and an optimal range for the specific individual of that percentage, pounds of body fat and an optimal range of body fat for that specific individual, and suggested pounds of body fat to lose. The body analysis includes the following: Basal Metabolic Rate (BMR) is the number of calories burned by the patient's lean body mass in a 24 hour period at complete rest using formulas such as the Harris-Benedict formula or other suitable formulas. Specific Dynamic Action of Foods (SDA) is the numbers of calories required to process and utilize consumed foods (in one case estimated at 5-15% of BMR, depending on personalization). Resting Energy Expenditure (REE) is the sum of BMR and SDA and represents the number of calories that the patient's body requires in a 24 hour period at complete rest. The system determines a Program Recommendation Total Caloric Intake as the caloric supplement required to achieve weight loss of approximately 2 pounds per week. Medications or stimulating substances (such as caffeine, gingsen, or diethylpropion) to assist in weight loss may be recommended and if so the program increases calorie consumption based on a model of the patient's response to such substances.

In one embodiment using the optional mobile monitoring hardware, the system determines Activities of Daily Living (ADL) as the number of calories burned by the patient's body during normal daily activities using accelerometers. The accelerometers can also determine the Calories Burned by Exercise as the number of calories burned by the exercises selected by the patient. Also included, is the level and intensity of the patient's activities. In one embodiment without the optional mobile monitoring hardware, the system approximates the Activities of Daily Living (ADL) as an average of calories expected to be burned by the patient's body during normal daily activities, and in one case is estimated at 20% or REE. The system can also receive averaged approximations of Calories Burned by Exercise is the number of calories burned by the exercises selected by the patient. Also included, is the level and intensity of the patient's activities.

FIG. 18B shows an exemplary process for monitoring patient food intake. The process first determines and recommends optimal diet based on patient parameters (3130). To monitor progress, the process takes user entered calorie data and optionally captures images of meals using a mobile device such as a mobile camera (3132). The process then translates images of the meals into calories (3134). The patient's actual diet is then compared to with the recommended diet (3136).

In one embodiment, the camera captures images of the food being served to the patient. The image is provided to an image search system such as the Google image search engine, among others. The search returns the likely type of food in the dish, and an estimation of the container volume is done. In one embodiment, the volume can be done using a 3D reconstruction using two or more images of the food found as the intersection of the two projection rays (triangulation). The two images from the 2D images are selected to form a stereo pair and from dense sets of points, correspondences between the two views of a scene of the two images are found to generate a 3D reconstruction is done to estimate the 3D volume of each food item.

The system determines and looks up a database that contains calorie per unit volume for the dish being served, and multiplies the food volume estimate with the calorie per unit volume for the type of food to arrive at the estimated total calorie for the dish. The user is presented with the estimate and the details of how the estimation was arrived at are shown so the user can correct the calorie estimation if needed.

FIG. 18C shows an exemplary exercise recommendation and monitoring process. First, the process determines and recommends an exercise routine that is customized to the patient's medical condition (3140). The process then captures patient exercise activity using micro-electromechanical systems (MEMS) sensors (3142). The MEMS sensors can include Accelerometer, Gyroscope, Magnetometer, Pressure sensor, Temperature, and Humidity sensor, among others. The process then correlates actual patient activity with the recommended exercises (3144).

In one embodiment, the above process collects data from and then compares the performance of the patient with similar patients. The process engages and motivates through Social Network Encouragement.

In another embodiment, initial data captured from the patient includes blood pressure, chronic diseases, present weight, height, present physical health, whether the patient is diabetic, among others. Other measurements include height, weight, blood pressure, as well as measurements of the wrist, upper arms, chest, waist, hips, thighs and finger. In preparing an individual weight loss program it is essential to consider the present physical activity level and diet of the patient.

In yet another embodiment, the system can automatically generate graphs for review by the patient and the dietitian to aid in preparing a meal plan and for the benefit of the patients to aid in setting goals in altering the eating habits. One chart can be a nutrient chart showing recommended daily requirements with respect to the amount of vitamins and nutrients consumed during an average day in comparison with the recommended allowance. The graph thus gives a clear indication of deficiencies and excessive amounts of vitamins and nutrients consumed in the present diet. Another chart shows calories from fats, protein, carbohydrates and alcohol in comparison with a similar chart of recommended percentages of calorie intake to show deficiencies in the source of calories and the need to reduce calorie intake from other sources.

Another chart can show consistency of the patient and potential corrective actions to existing eating habits. An additional column lists the Recommended Daily Allowance as recommended by the U.S. Senate Committee. From this data the percentage of nutrient intake compared to the Recommended Daily Allowance is calculated and printed on the report. Finally a column reporting the deficiency or excess of nutrients consumed appears. From this column the dietitian can readily identify those nutrients of which the patient's diet suffers a deficiency.

In determining the percentages of nutrients compared to the recommended daily allowance the computer goes through a series of determinations using fiber intake as an example. From the actual diet the computer is able to determine the amount of fiber in each food item. The generally accepted range of fiber intake is from 10-40 grams per day. The computer initially determines if the daily fiber intake is in excess of the maximum 40 grams/day allowance. If the fiber intake does not exceed 40 grams the system determines the percentage fiber over the maximum allowed amount. If the fiber intake does not exceed 40 grams/day the computer then determines if the fiber intake is greater than 10 grams/day. If the fiber intake is greater than 10 grams/day and less than 40 grams/day the computer will indicate that the fiber intake is within the acceptable level. Should the fiber intake be less than 10 grams/day the total fiber intake is divided by 10 to calculate the percentage of fiber in the daily diet. A similar analysis is performed by the computer for each of the nutrients.

One embodiment provides a meal plan based on the American Diabetics Association recommendation which breaks food down into 8 categories. These categories include a fruit exchange, vegetable exchange, milk exchange, grain and cereal exchange, fat exchange, lean meat exchange, medium fat meat exchange, high fat meat exchange. Under each of these categories a wide variety of food items is listed which offers the patient a selection of food items according to their taste preferences. While the total calorie consumption per day is of major importance, it is essential that these calories be provided from the sources specified in the meal plan. Once the patient has designated a meal plan the patient can select a food item from each of the specified food exchanges. This allows variation and compensation for the patient's food preferences.

The exercise chart provided educates the patient as to what activities should be considered, proper methods of selecting an exercise program and proper procedures of exercising. Additionally, the exercise chart provides training guidelines for increasing one's exercise through a 12 week period. For each week of the training period the exercise chart provides guidelines as to duration and level of physical activity. An accelerometer is used to monitor the duration and level of activity.

Additional measurements 6 taken at this time are of fundamental importance in having a significant psychological impact on the patient. From these measurements the patient is able to readily recognize the need for a change in his eating habits and lifestyle. Throughout the weight loss program these measurements provide evidence of a reduction in size of various parts of the body and in addition to a reduction in weight gives the patient encouragement and confidence that the program is effective. The measurements include the circumference of the arms, waist, hips, chest and fingers.

The next stage in the weight management system involves extensive consultation between the patient, the system's communication agents, and the dietitian using the communication facilities of the system. The system, with the dietician, automatically outlines the deficiencies of the patient's existing eating habits and diet compared to a breakdown of calorie intake as recommended by the United States Senate Committee. The system shows a comparison chart with expert recommendations and the patient's own diet results in a higher interest which in turn makes learning much easier.

Initially the system helps the patient to correct one dietary correction as the goal for that week. At the end of the week the rule-based agent reviews the progress and if that one weakness is showing satisfactory improvement, additional goals are set to correct the remaining deficiencies. Normally the deficiencies are corrected one at a time. In order for the dietitian to aid the patient in setting goals the computer analysis calculates at which nutrients a deficiency exists. In one embodiment, the rule based agent classifies the nutrient into two categories identified as Priority I and Priority II nutrients. The Priority I nutrients are the nutrients where the amount taken in must be within a specified range. The human body requires a specified amount of these nutrients to function properly on a daily basis, however, an excessive amount has been shown to have undesirable consequences. The Priority I nutrients for the purposes of this example include, cholesterol, fiber, sodium fat and calcium. The Priority II nutrients are those which, while essential to good health, are not of major concern if the diet periodically does not provide the recommended daily allowance. For the purposes of example only these Priority II nutrients may include vitamin A, riboflavin, niacin and vitamin C. The computer analysis determines whether there is a deviation of any of these Priority I nutrients from the recommended daily allowance. If there is a deviation the computer determines the number of nutrients of which there is a deviation and if there are two or more the computer selects the two nutrients with the highest deviation. From this identification the dietitian is able to recommend particular foods to correct the nutrient excess or deficiency. For example, if the analysis indicated the sodium and fat level as being abnormally high the dietitian might recommend a reduction in specific types of meat and reducing the intake of salted foods. The two highest deviations would normally be used as the first goals.

If there is only one Priority I nutrient deviation it has been considered not to be of major immediate concern and will normally be corrected by adjusting the overall diet. The computer detecting only one deviation of Priority I nutrients then determines the number of deviation from the recommended daily allowance of the Priority II nutrients. As with the Priority I nutrients the computer identifies the two nutrients having the greatest deviation. From this identification the system is able to set goals with the patient to correct the deviation. For example, if the computer determines this is a major deficiency of vitamin C and vitamin A the rule based agent might recommend a diet concentrating more on green vegetables and citrus fruits.

In selecting a meal plan it is necessary to determine the number of calories recommended per day in order to lose and maintain a desired weight. The first step is to find the patient's reasonable or desired weight for their height and build. From the height and build the weight is determined based on data prepared by the Metropolitan Insurance Company in 1983. The Handbook of Clinical Dietetics, Yale University Press, provides a formula for determining the maximum calories to be consumed per day necessary to maintain one's weight.

For those extremely overweight a drastic reduction in calorie intake is liable to have serious and psychological and emotional consequences which may rapidly discourage the patient and leave the program. For this type of situation an intermediate menu plan is prepared by computer analysis to offer a compromise between the ideal calorie intake level to achieve the desired weight and the calorie intake of the old eating habits. In determining whether an intermediate menu plan is appropriate the computer receives an input of the present weight A, ideal weight B and the activity level C. The activity level is the number of calories needed per pound per day. From this data the computer determines the excess in calories consumed per day D according to the formula: $(A \times C)-(B \times C)=D$ If the excess calories D is greater than 1000 calories per day an intermediate menu plan is recommended.

The system also encourages social network based behavior modification with friends and family and normative message that compare the patient's progress with similar patients. Acceptance of the meals by the family members offers positive reinforcement to the patients which have proven to be a powerful tool in changing one's lifestyle. For most people the weight management system is a tremendous undertaking which requires support from the patient's family. It has been found that family counseling can be a major factor in the success of the program. Effective weight loss and change in lifestyle affects not only an individual but everyone in the patient's environment. Support is necessary from the family members in order to maximize the chances of success.

Using the social network messaging, positive reinforcement is further provided by group sessions between the different patients. Each patient asks questions, exchanges experiences and offers support and encouragement to each other. Discussions about the reactions of family members to the meals prepared offers encouragement to others to try different recipes. There are two types of social norms that exert influence. While the result, conformity, is the same for both types of influence, the motivation behind conformity is different in each case. Injunctive norms encourage conformity by implying that a certain attitude or behavior is approved of or disapproved of by a social group. Descriptive norms imply that an attitude or behavior is common among members of a group, regardless of approval.

Exercise is an essential part of any effective weight management system. A group sessions by a fitness trainer or physiologist on the benefits and attributes of proper exercise can be scheduled. Techniques for proper ways to exercise and the proper amounts of exercise are discussed in detail. Various activities by the individual patients are shared with the others thereby offering encouragement and reinforcement for their goals of managing their weight effectively in a safe and healthy manner. Different exercise programs and activities are discussed and dates are set for these activities. It has been found that for the beginner a firm commitment by the patient is an essential aspect of developing a regular exercise program.

The normative messaging relies on normative social influence which is "the influence of other people that leads us to conform in order to be liked and accepted by them." This often leads to public compliance—but not necessarily private acceptance—of the group's social norms. When people tend to conform to normative social influence is explained by the social impact theory. Social impact theory states that the more important the group is, the closer the physical distance is between the group and oneself, and the number of people in the group all affect the likelihood that one will conform to the group's social norms. This is similar to one environment where households that received more normative messages in which described the frequency and amount of weekly recycling, began to have a direct impact on both the households frequency and amount of curbside recycling. The sudden change was due to the fact that "the other neighbors" recycling habits had a direct normative effect on the household to change theirs. Similar results were apparent in hotels where towel usage increased by 28% through normative messages. Direct personal experience is not a necessity for normative tendency. Written communication instructing how people should behave or describing how most people act in a given situation can generate the same normative behavior in people.

In many cases, normative social influence serves to promote social cohesion. When a majority of group members conform to social norms, the group generally becomes more stable. This stability translates into social cohesion, which allows group members to work together toward a common understanding, or "good".

Figure 19:
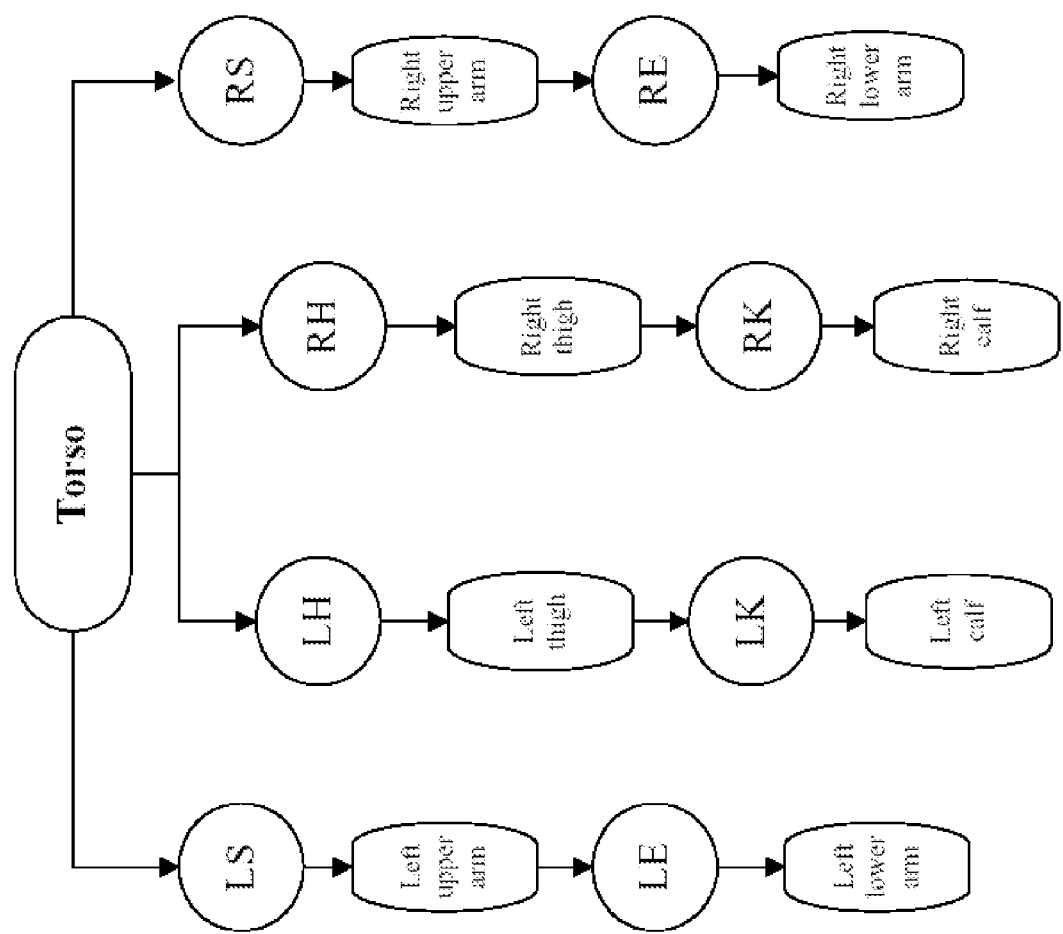
FIG. 19 shows an exemplary exercise monitoring system.

As part of the exercise session a specific activity is scheduled and undertaken by the patients which may for example be a walk or muscle exercises. FIG. 19 shows an exemplary kinematic exercise monitoring system. In one implementation, an HMM is used to track patient movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Wireless sensors with tri-axial accelerometers are mounted to the patient on different body locations for recording. Sensors can be placed on (or cameras can detect) the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generates a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and calorie consumption is assigned to each muscle movement and can be varied according to the frequency and the range of the movement to arrive at an accurate measurement of energy expenditure when the patient walks or exercises.

For most healthy adults, the Department of Health and Human Services recommends these exercise guidelines:

Aerobic activity. Get at least 150 minutes a week of moderate aerobic activity or 75 minutes a week of vigorous aerobic activity. However, to effectively lose or maintain weight, some people may need up to 300 minutes a week of moderate physical activity. You also can do a combination of moderate and vigorous activity. The guidelines suggest that you spread out this exercise during the course of a week, and sessions of activity should be at least 10 minutes in duration.

Strength training Do strength training exercises at least twice a week. No specific amount of time for each strength training session is included in the guidelines.

Moderate aerobic exercise includes such activities as brisk walking, swimming and mowing the lawn. Vigorous aerobic exercise includes such activities as running and aerobic dancing. Strength training can include use of weight machines, or activities such as rock climbing or heavy gardening.

As a general goal, the system encourages the user to perform at least 30 minutes of physical activity every day. Specific calorie expenditures vary widely depending on the exercise, intensity level and the user's individual situation. The system receives communications from the user on the exercise, and uses rules from the chart below on the estimated number of calories burned while doing various exercises for one hour, as modified using the MEMS activity sensor and the kinematics model of FIG. 19.

| Activity (1-hour duration) | Weight of person and calories burned | | |
|---|---|---|---|
| | 160 pounds (73 kilograms) | 200 pounds (91 kilograms) | 240 pounds (109 kilograms) |
| Aerobics, high impact | 533 | 664 | 796 |
| Aerobics, low impact | 365 | 455 | 545 |
| Aerobics, water | 402 | 501 | 600 |
| Backpacking | 511 | 637 | 763 |
| Basketball game | 584 | 728 | 872 |
| Bicycling, <10 mph, leisure | 292 | 364 | 436 |
| Bowling | 219 | 273 | 327 |
| Canoeing | 256 | 319 | 382 |
| Dancing, ballroom | 219 | 273 | 327 |
| Football, touch or flag | 584 | 728 | 872 |
| Golfing, carrying clubs | 314 | 391 | 469 |
| Hiking | 438 | 546 | 654 |
| Ice skating | 511 | 637 | 763 |
| Racquetball | 511 | 637 | 763 |
| Resistance (weight) training | 365 | 455 | 545 |
| Rollerblading | 548 | 683 | 818 |
| Rope jumping | 861 | 1,074 | 1,286 |
| Rowing, stationary | 438 | 546 | 654 |
| Running, 5 mph | 606 | 755 | 905 |
| Running, 8 mph | 861 | 1,074 | 1,286 |
| Skiing, cross-country | 496 | 619 | 741 |
| Skiing, downhill | 314 | 391 | 469 |
| Skiing, water | 438 | 546 | 654 |
| Softball or baseball | 365 | 455 | 545 |
| Stair treadmill | 657 | 819 | 981 |
| Swimming, laps | 423 | 528 | 632 |
| Tae kwon do | 752 | 937 | 1,123 |
| Tai chi | 219 | 273 | 327 |
| Tennis, singles | 584 | 728 | 872 |
| Volleyball | 292 | 364 | 436 |
| Walking, 2 mph | 204 | 255 | 305 |
| Walking, 3.5 mph | 314 | 391 | 469 |

The system can automatically schedule appoints for doctors, dieticians, and fitness consultants. One exemplary platform supports multi-vendor scheduling with the rule based communication system discussed above. The platform provides a one-stop scheduling system for end-users to make appointments and connect with medical service providers who sign up with the system. For example, the scheduling platform serves a variety of business verticals such as doctor offices, specialist offices 4104, hospitals, dieticians, and exercise specialists, among others. The system provides a web-based and mobile scheduling software for connecting multiple industries' scheduling onto one platform.

The system minimizes the hassle of booking appointments through an array of channels with no consistencies or simplicity: phone, online, booking sites, hospital or medical office websites. The system reduces error arising when the user forgets to put the scheduled appointment onto calendar (iPhone, Outlook, Google). The system reduces the time and effort required to find a service provider with walk-in availability given an impromptu desire. Additionally, the inefficiency of manual scheduling of appointments and staff availability is avoided.

A user can sign-up with the system at a web site or download through an app directly on iPhone or Android-operated phones. For convenience, the system allows the use of Facebook sign-in information. Once the user is signed-in, the user can search for a specific company or by certain criteria (type of service, closest date of availability, etc), and schedule the appointment. The appointment will also integrate with the user's choice of major calendar tool such as iPhone's calendar, Outlook, Google Calendar. For any alteration or cancellation of appointments booked through the system, a URL allows the user to be directed to the platform to do so. Reminders are sent to the user based on his choice of contact channel, and provide an opportunity to cancel the booking instead of "no-show" at last minute.

Medical vendors who sign up for the system's scheduling services are empowered to use many functionalities that improve customer experiences, employee and customer scheduling efficiencies, and increase revenue by maximizing capacity utilization and engaging customers.

The business vendor inputs its operating hours, maximum capacity for each hour (depending on industry, maximum capacity may be further itemized by employee or by table, among others), duration for each type of services. It is anticipated that these inputs are only required to be updated once in a while. The system allows the company administrator to manually input a customer booking in the event the customer phones or walk in person. As such, once the master schedule inputs are completed, the company is able to view its appointment book on a real-time updated basis. There are fewer occurrences of writing down the wrong time, name or phone number of customers.

Business vendors also have the choice of putting a "book now" button (powered by the instant platform) on their company websites. Once a customer presses on the "book now" button, he is able to schedule an appointment with that business vendor on an interface powered by the instant. Even if the business vendor chooses not to have its business listed on the platform visible to all users, the business vendor's customers can still schedule appointment with this vendor by pressing on the "book now" button.

For businesses who want more control over appointments, they can opt to have the ability to reject or decline an appointment. After opting for such flexibility and if business vendor does not respond to the appointment request in time (specified by the business vendor), the appointment will be deemed as accepted.

The system provides customized services which are locally optimized to suit an individual user's requirements and yet which globally optimize the utilization of the system resources supporting such customized services for each individual seeking customized services. With the system, users will get the simplicity and convenience of scheduling appointments within one platform instead of having to go into multiple websites or applications. Once appointments are made, users will also easily integrate the appointment details within the users' existing calendar tools (such as iCal). In addition to scheduling appointment for an individual user's own purpose, the platform also allows users to coordinate events with their friends and make the appointment directly on the system (after the venue, date and time are voted on and chosen on the system).

The system provides a holistic scheduling platform that allows businesses from all industries to sign-up and customers can schedule appointments with these businesses or vendors through the system's website as detailed below. Mobile users can access the system though a mobile application such as an Android or iPhone application. The mobile app provides a better user experience than mobile websites are capable of.

Users can also access the system through a vendor website through a "Book Now" widget. The "Book Now" widget is a button displayed on the vendor's web site for a user creates an appointment using the system. When the user clicks the "Book Now" button on the vendor's site, an appointment can be created with a link back to the vendor's website. One embodiment uses the Open Graph protocol to specify information about the vendor entity. When the vendor includes Open Graph tags on its Web page, the page becomes equivalent to a system's page. This means when a user clicks the "Book Now" button on the vendor's page, a connection is made between the vendor's page and the user. The vendor page will appear in the "Likes and Interests" section of the user's profile, and the vendor has the ability to publish updates to the user. There are two "Book Now" button implementations: XFBML and Iframe. The XFBML (also available in HTML5-compliant markup) version is more versatile, but requires use of the JavaScript SDK. The XFBML dynamically re-sizes its height according to whether there are profile pictures to display, gives the vendor the ability (through the Javascript library) to listen for like events so that the system knows in real time when a user clicks the "Book Now" button, and it always gives the user the ability to add an optional comment to the book now function. If users do add a comment, the story published back to the vendor is given more prominence.

Vendors can access the system through an administrative console. In these verticals, for the business vendors who sign-up with the platform, they have the flexibility and choice to do the following:

1. Input all or some of the business' operating hours and schedule availability, so that users can automatically schedule appointment anytime, anywhere.
2. Opt for ability to decline or reject appointments.
3. Opt for the business not to be displayed on the list of business vendors, while that business' customers can still schedule online appointments automatically through a "book button" that is supplied by the system for display on the business' website.

The system performs aggregation of different variables and inputs for different industries in order to solve for the same thing: schedule availability. Whilst to the user, the platform gives them the same convenience of finding the schedule availability so they can book any vendors.

For the medical offices, the variable inputs that solve for schedule availability or the vendor in this industry aggregates the vendor's staffs own individual schedule and service duration. The ratio of staff to customer is generally 1:1. Assume a vendor in this industry has 3 staffs who perform services. For timeslot 9-10 am, Staff A has been booked but Staff B and Staff C have not been booked. Then there exists 2 remaining available booking slots for 9 am. For exercise gyms, the key variable inputs that solve for schedule availability are defined by equipment. The vendor names the equipment and defines it by seating capacity and maximum time limit allowed for that equipment per each booking. For gym class activities, the key variable inputs that solve for schedule availability consists of seat capacity per course, duration of course, frequency of course (per a multitude level of units such as daily, weekly, biweekly, month and also for each of these, a subset of occurrence frequency exists such as occurring 2 days per week or 1 day per week, for example).

In one embodiment, the specific variables and inputs for exemplary industry-flows in calculating total availability (by date or by staff or by earliest availability). The system will deduct the online bookings made by users and manual bookings input by vendors to constantly arrive at "remaining schedule availability" real-time. The Variables and Inputs include:

Total number of staff (service providers)
Each staffs availability on each day and time
Each staffs list of services provided (i.e. each staff is tagged with all the services she/he can provide)
Define and listing of each service
Duration of each service Web user and mobile user can use the system to book appointments on the scheduling platform. In one exemplary appointment booking workflow handles three possible usage scenario: 1) through the system's web site, 2) through a "Book Now" button 4132, or 3) through a mobile application.

In one usage scenario, the user visits the system's web site. The user may browse or search the interface for a service provider to suit their needs. In a mobile usage scenario, the user is directed to search for service providers from a mobile application. In one usage scenario, the user clicks on a "Book Now" button at a vendor's web site. The user is immediately transferred to an interface on the system's web site where the user can search for a date and time for a suitable appointment. Once a desired service is found, the user is presented with times and dates of available appointments. Once the desired time and date are chosen, the user is asked to log in to the system using an account. If the user does not yet have an account, he/she will create a user account. If the user account already exists, the user will simply log in. In another embodiment, the user logs in to an account previous to reserving a time and date. Once logged in, the appointment is scheduled with the user and vendor. In some instances, approval for the appointment is not required. If this is the case, the appointment is automatically saved to the calendar of the user for later viewing or reminder. A notification email is also sent to the user. In another instance, approval is required by the vendor. In this case, the appointment is placed on the approval queue of the vendor.

One example use scenario is described next. In one embodiment, a web user visits a web site and search for a vendor or service provider. Once the desired provider is found, the user can then search for a time and date to reserve an appointment with the vendor. If the user does not already have a user account, he will be asked to create one. The user then logs in to schedule the appointment with the vendor. If approval is required by the vendor, then the appointment is placed on an approval queue. If not, the date and time are saved to a user's calendar, and an email confirming the appointment is sent to the user. From the vendor's view point, the provider visits the site and creates an account and then logs in. Once signed in, the provider profile can be created or reviewed. In the event of a new business profile, the vendor will also have to upload its existing schedule data onto the platform. From this point, the vendor can also input manually booked reservations into the platform and update the schedule database.

In addition to hospital patient and equipment monitoring, the system can be used in other applications. In an employee access application, the system enables an employer to selectively grant access to specific rooms of a facility. Additionally, when an employee is in an area where he is not normally present, the system can flag a warning to the facility administrator. Further, the computer of the employee can be access locked so that only the employee with the proper wireless authorization can work on a particular computer. All employee accesses, physical as well as electronic, are tracked for regulatory requirements such as HIPAA requirements so that the administrator knows that only authorized personnel are present. Additionally, the employee can be paged in case he or she is needed through the voice walkie-talkie over the Zigbee network.

In a vending machine monitoring application, the system can monitor vending machines remotely located to a central monitoring system. For example, transmitters can be placed within soda machines to monitor the depletion of soda machines. When a "sold out" indication is present in the vending machine, the system can transmit refill/reorder requests to a supplier using the wireless network or the POTS network. Also, the status of the vending machine can be monitored (e.g., the temperature of a ice cream machine or soda machine) to notify a supplier or the maintenance department when maintenance is required.

In a prisoner monitoring embodiment, people who are subject to incarceration need to be monitored. The system can constantly monitor the prisoners to ensure they are present. A prisoner has a wireless appliance that is secured or unremovably attached to his person. If the wireless appliance is forcibly removed it immediately transmits a notification to the prisoner monitor. In a Home Confinement Monitoring embodiment, a convict can be required not to leave their home. They are monitored by the wireless appliance attached to the "home prisoners" which are then monitored by a central monitoring center or station which can be a sheriffs office. In the home prisoner monitoring system, the wireless appliance is secured to or unremovably attached to the home prisoner and if they move outside of the range of the network (i.e., the leave the house), no transmission will be received by the wireless transceiver and an alarm is issued by the remote home prisoner monitor. In one embodiment, the alarm can be a phone call or an email message or fax message to the monitoring center or station.

In an Animal Monitoring embodiment, the system can monitor the status and presence of animals in a stock yard or on a farm by the similar methodologies discussed above. In this embodiment a plurality of animals can be monitored for presence as well as condition. For example, the system can ensure that animals have not wandered off as well as determine conditions such as temperature or heart rate of an animal, this can be accomplished by placing a wireless appliance on the animal.

In a utility monitoring embodiment, a wireless appliance is interfaced with a utility meter and thereafter transmits the current meter reading at predetermined intervals. Because of the low power requirements of Zigbee and the low duty cycle and low data rate required for transmitting the information, the battery for powering the Zigbee radio transmitter can last many months or more.

Figure 20:
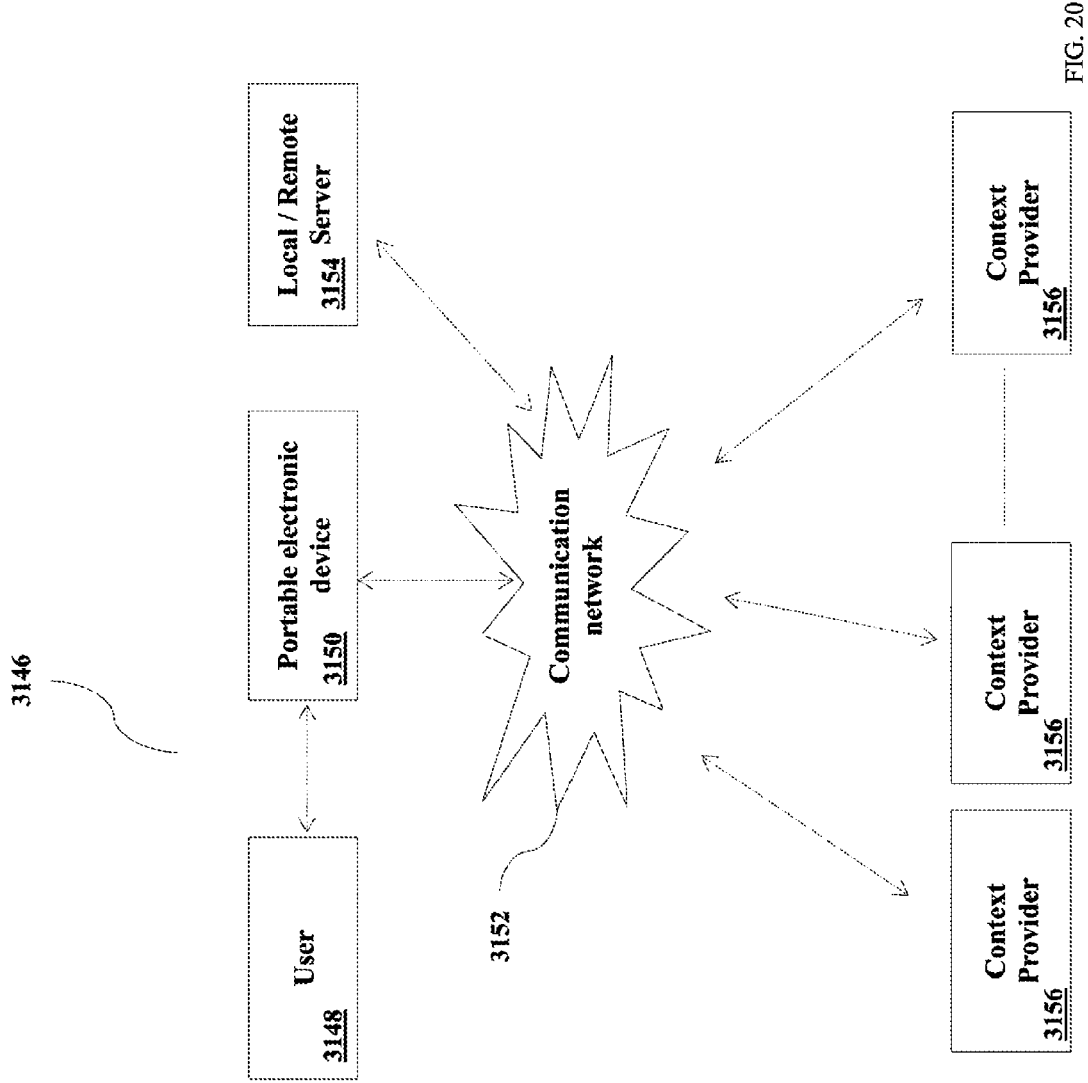
FIG. 20 shows exemplary environment for collecting sensor data to determine a status of a user.

FIG. 20 shows exemplary architectural environment 3146, usable to collect sensor data of the user 3148. The environment 3146 includes an example portable electronic device 3150 configured to include one or more sensors to collect user habitual information. The portable electronic device 3150 described herein can include, but not limited to, a smart phone, a wireless computing device, a cellular phone, a personal digital assistant, a personal navigation device, a personal computer, a portable media player, a personal digital assistance, a laptop, or any other computing device. The portable electronic device 3150 can be configured to collect sensor data via sensors integrated on it and determine the status of the user to provide appropriate recommendations. In an embodiment, the sensor described herein can include, but not limited to, accelerometer, barometer, implantable internal and external sensors, or any other sensor. In an embodiment, the portable electronic device 1350 can be configured to include the sensors or may include interfaces with other sensor devices to access the sensor data and receive user habitual information over a communication network 3152.

The communication network 3152 described herein can include any type of communications network(s), including for example, but not limited to, wire-based networks (e.g., public switched telephone, cable, data networks, and so on), wireless networks (e.g., cellular, satellite, Wi-Fi, Bluetooth, radio-frequency, and so on), or a combination thereof.

In an embodiment, the sensors described herein can represent an application service that can be operated as a part of any number of online service providers, such as an e-health service, a map service, a social networking site, a search engine, or the like. Further, the sensors can include additional modules or can work in conjunction with modules such as to perform the operations discussed below. In example implementations, the sensors can be implemented at least in part by a status application executed by servers, or by a status application stored in memory of the portable electronic device 3150.

Further, the environment 3146 can include one or more local/remote servers 3154 and one or more context providers 3156, which may be stored on a separate server or with the representative set of servers that can be accessible via the communication network 3152. The one or more local/remote servers 3154 and the one or more context providers 3156 can store information collected and generated by the status application and can be updated on a predetermined time interval, in real-time, or periodically.

Typically, the user 3148 carries the portable electronic device 3150 in a pocket or a purse, and the portable electronic device 3150 can accesses the status application or the sensor application such as to start collecting the sensor data. However, collecting sensor data about individuals can presents privacy concerns, such as transmitting the sensor data of the individuals over the communication network 3152. Options are available to address privacy concerns. The options are that an individual user may choose to opt-in to participate or to opt-out to not participate in tracking or sharing of sensor data. As such, the tracking of the sensor data may require explicit user consent.

In the example, the portable electronic device 3150 can be configured to starts recording when the sensors on the portable electronic device 3150 are activated by a wireless signal (e.g., from the user 1348 using the portable electronic device 3150, from a global system for mobile communications (GSM) device, from a Bluetooth® hands free device, from a Wi-Fi access point in the building, or from a broadcast radio signal). In an example, the portable electronic device 3150 may record the user 3148 habits information (for example, the user 3148 enters a building), and may record the user 3148 walking up the stairs, eating food at a restaurant, running on thread mill, coughing, doing yoga in a silent room, meditating, or the like. Further, different user habits information recorded of the portable electronic device 1350 is described in conjunction with FIG. 22.

Figure 21:
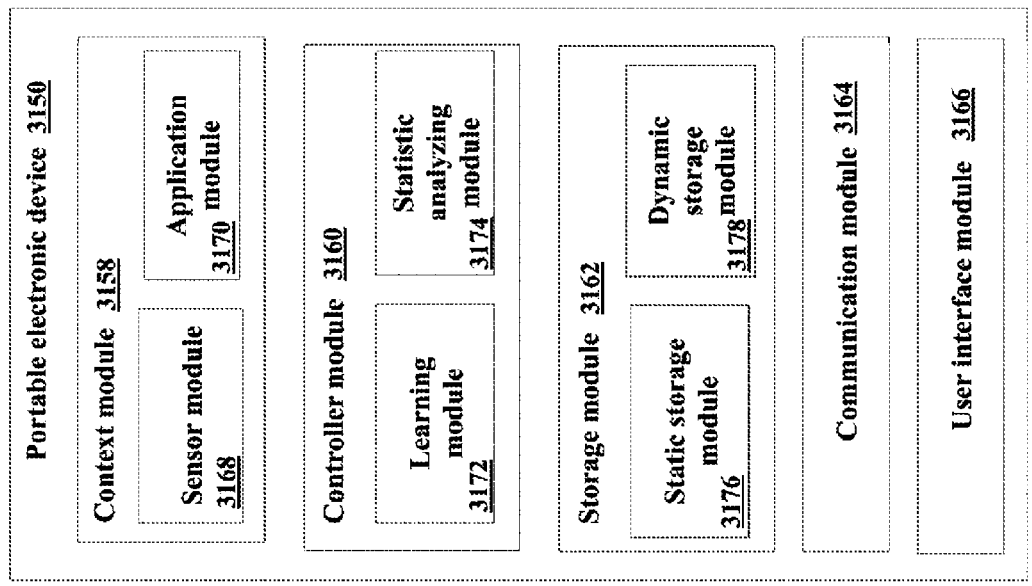
FIG. 21 shows different modules of portable electronic device as described in the FIG. 20.

FIG. 21 shows different modules of the portable electronic device 3150 as described in the FIG. 20. The portable electronic device 3150 can be configured to include a context module 3158, a controller module 3160, a storage module 3162, a communication module 3164, and a user interface module 3166. In an embodiment, the context module 3158 can be configured to collect one or more habits information of the user 3148. In an embodiment, the one or more habits described herein can include static habit information and dynamic habit information. The term "static habit information/data" described herein can be the information which may not change or changes very slowly. Inversely, the term "dynamic habit information/data" described herein can be the information which changes much more often. In an embodiment, the context module 3158 can be in charge of collecting, being aware users' context information and analyzing new context information.

In an embodiment, the context module can be configured to include a sensor module 3168 and an application module 3170. The sensor module 3168 described herein can be configured to collect the user dynamic habits information/data using the sensors of the portable electronic device 3150. The dynamic habits data can be collected based on, for example, indications of non-movements, movements, locations, or environmental conditions around the user 3148, along with detecting speech being spoken in proximity to the user 3148. In an embodiment, the context module 3158 can be configured to infer activities based on the extracted features of the collected dynamic habits data. The portable electronic device 3150 can be configured to use a discriminating power to identify correlations between features of the collected sensor data and possible activities. Further, the detailed overview of the dynamic habits information of the user 1348 is described in conjunction with FIG. 22a.

In an embodiment, the application module 3170 can be configured to determine the static habits data of the user 3148. The application module 3170 can be configured to interface with different applications present in the portable electronic device 3150 such as to collect the static habits data of the user 3148. In an example implementation, the application module 3170 can gather information about the inferred activities of the user 3148 that occurred and are likely to occur in the user's daily life. For example, the activities described herein can include office working time, meeting time, the user 1348 schedules, office tea time, office lunch time, tasks, user birth day, party dates, appointments, and the like. Further, the detailed overview of the dynamic habits information of the user 1348 is described in conjunction with FIG. 22b.

In an embodiment, the controller module 3160 can be configured to predict preventive health care recommendation based on one or more rules and the one or more habits collected from the user 1348. In an embodiment, the controller module 3160 can be configured to implement one or more rules for the one or more habits received from the user 1348. The one or more rules described herein can include one or more condition/logic to recommend one or more recommendations to the user 1348 based on the collected habits information. In an embodiment, the controller module 3160 can be configured to include a learning module 3172 and a statistic analyzing module 3174.

In an embodiment, the learning module 3172 can be configured to receive one or more similar habits information associated with one or more users. The learning module 3172 can be configured to interface with different electronic devices such as e-health platform, the one or more content providers 3156, the one or more local/remote servers 3154, research centers, health information exchange systems, and the like to receive information about the users having same/similar habits. In an embodiment, the learning module 3172 can be configured to interact with hospital platform such as to receive solutions, suggestion, advices, diseases, medications, treatments, prescriptions, and the like associated with the similar/same habits. In an embodiment, the statistical analyzing module 3174 can be configured to analyze the information received from the learning module 3172 over a span of time. The statistical analyzing module 3174 continuously analyzes the data such as to quickly provide recommendations/advice associated with the habits. In an embodiment, the controller module 3160 can be configured to predict the preventive health care recommendations to the user 1348 based on the stored one or more rules and the habits information received from the user 1348.

In an embodiment, the storage module 3162 can be configured to store the one or more rules and the one or more habits received from the user 1348. The storage module 3162 can be configured to include a static storage module 3176 and dynamic storage module 3178. In an embodiment, the static storage module 3176 can be configured to store static habits data received from the user 1348. In an embodiment, the dynamic storage 3178 can be configured to store dynamic habits data of the user 3148.

In an embodiment, the communication module 3164 can be configured to communicate with local/remote devices, such as to receive/transfer information to/from the user 1348. The communication module 3164 can be configured to include one or more interfaces such as to communicate with the portable electronic device 3150. In an embodiment, the user interface module 3166 can be configured to provide a graphical user interface (GUI) to the user 1348 such as to access the predicted preventive health care recommendations to the user 1348.

Figure 22A:
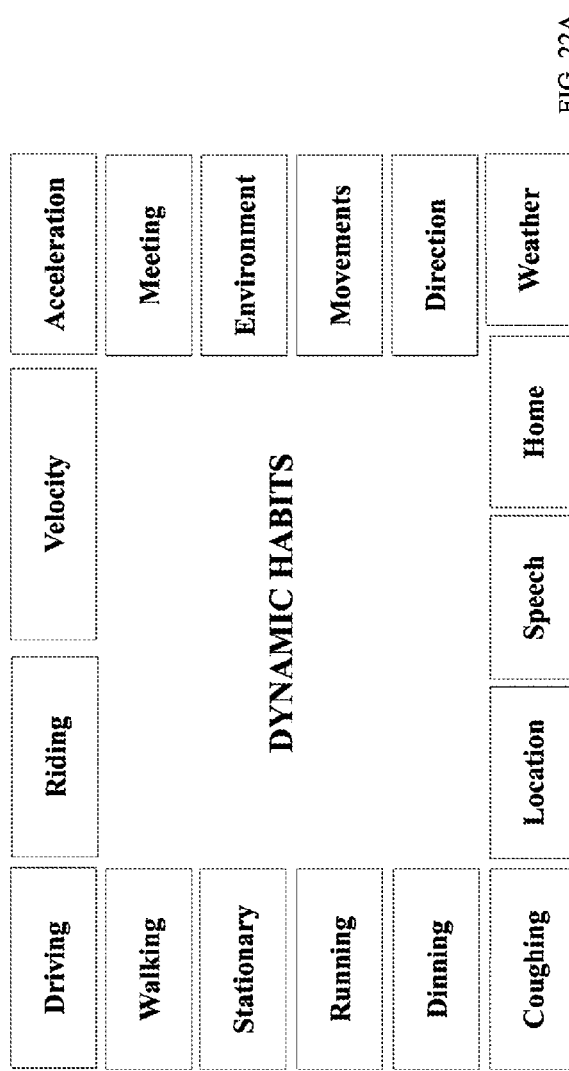
FIGS. 22a and 22b shows exemplary dynamic and static habits of the user.

FIG. 22a shows exemplary dynamic habits data of the user 1348. For example, features collected from the context module 3158 can include both the static habits data and the dynamic habits data. An example of the dynamic habits (which may changes much more often) collected by the portable electronic device 3150 can include, but are not limited to, the user 108 is driving a bus, car, van, and so on, the user 108 is riding in escalator, elevator, and so on, the user 108 is walking on road, park, lawn, and so on, the user 108 is stationary, the user 108 is running, the user 108 is dinning, the user 108 is coughing, the user 108 surrounding weather data, the user 108 is in meeting, the user 108 surrounding environment data, route taken by the user 1348, the user 108 direction, the user 108 velocity, the user 108 acceleration, direction of movement of the user 3148, locations of the user 3148, environmental noise levels surrounding the user 3148, speech being spoken in proximity to the user 3148, words spoken by the user 1348, the user 1348 is sitting in an office or a conference room, the user 108 is sitting in a quiet location or in a location with some background noise, the user 108 is speaking or other individuals are speaking, and the like data associated with the user 1348.

Figure 22B:
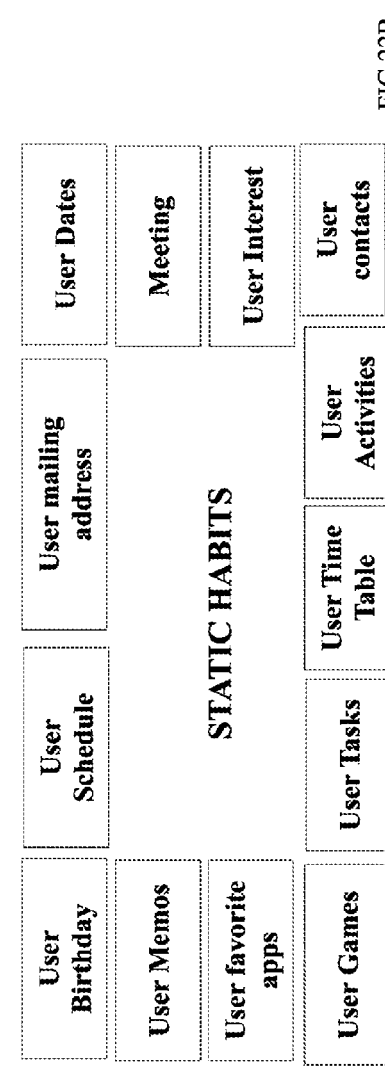

FIG. 22b shows exemplary static habits data of the user 1348. An example of the static habits static habits (which may not change or changes very slowly) collected by the portable electronic device 3150 can include, but are not limited to, the user 3148 memos data, the user 3148 favorite apps data, the user 3148 games data, the user 3148 tasks data, the user 3148 time table data, the user 3148 activities data, the user 3148 contacts data, the user 3148 interest data, the user 3148 meeting data, the user 3148 dates data, the user 3148 mailing address data, the user 3148 schedule data, the user 3148 birthday data, the user 3148 favorite food data, the user 3148 likes and dislikes data, and the like.

Figure 23:
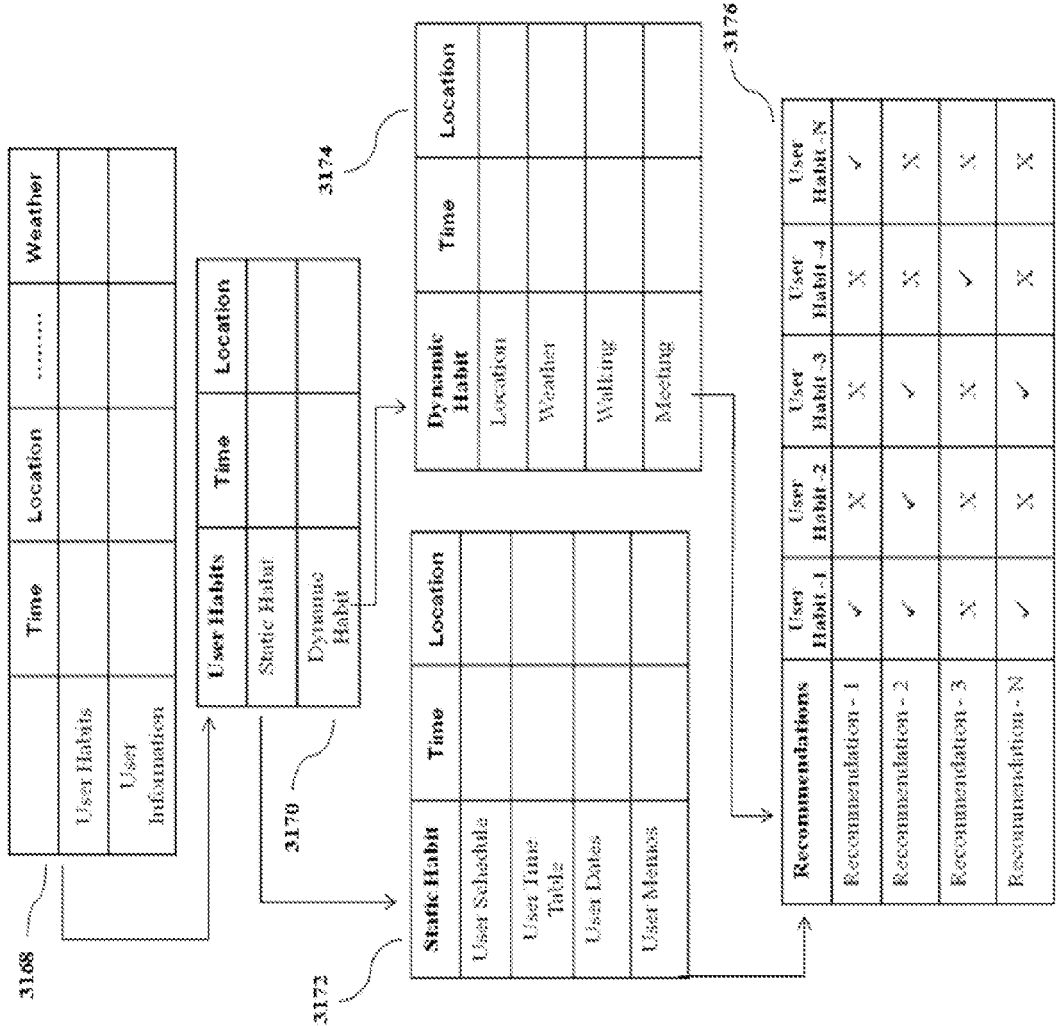
FIG. 23 shows an exemplary preventive health care recommendation tables.

FIG. 23 shows an exemplary preventive health care recommendation tables. In an example, as one-level two-state context prediction algorithm (also referred as recommendation prediction algorithm) is described in the FIG. 23, depending on the user static and dynamic habits and the one or more rules stored in the system. In first table 3168, there is user's habits information and user's information that can be referenced to user's habits table 3170 and which may further referenced to user's static habit table 3172, and user's dynamic habit table 3174. The tables are configured to store the user habits information received from the context module 3158. The algorithm is configured to map the information stored in theses tables such as to provide recommendations to the user 1348. The information stored in the static and dynamic habits tables can be further referred by a preventive healthcare recommendation table 3176 such as to provide effective recommendations. The algorithm is configured to apply one or more rules which may select effective recommendations for the user 1348 based on the user static and dynamic habits. In an embodiment, the one or more rules described herein can be defined based on the information received from the one or more content providers, electronic medical record of the user 1348, historic treatments provided to different patients having similar (or substantially similar or same habits). In an example, some of the operations performed by the recommendation prediction algorithm are shown below:

Step 1: Get user's current information and go to step 2. The user current information can include user's current static and dynamic habits information. The system uses the context module 3158 to receive the static and dynamic habits of the user 1348.

Step 2: Check the user current information with the information stored in the tables such as described in the FIG. 23. If the information is different from the information stored in the tables, then store the current information in the tables and go to step 3. For example, the system can be configured to check the values received by the context module 3182 with the values already stored in the system, if the values are different or the values is not a null value, then store the current values of the user 1348 and go to step 3.

Step 3: Get users' static information (such as scheduled tasks, timetable, time, etc.). Go to step 4.

Step 4: Determine if any of the static habit matches with the user dynamic habits and go to step 5. For example, if the user 1348 received dynamic habit is eating and the static habits indicates the user usual time for lunch is in the office canteen then the system determines that the user 1348 is eating food in their office canteen.

Step 5: Search the most suitable recommendation depending on the habits information. If results are found, then send them to the user device and go to step 6. For example, as shown in the FIG. 23, the preventive recommendation table 3176 can use the one or more rules such as to determine the recommendations for the user 1348. In an example, according to the one or more rules, if the user 1348 have the habit-1 then provide recommendations $1^{st}$, $2^{nd}$, and Nth. If the user has habit-2 then provides recommendation 2nd. If the user has habits $1^{st}$ and Nth then provide recommendation 1. Similarly, if the user has habits 1 and 3 then provide recommendation Nth.

Step 6: Display the recommendations to the user 1348. Request the user 1348 to provide information about their health and go to step 7. For example, the system provides the recommendations to the user 1348 and request to provide health information after performing the recommended action. In an example, the user may perform the recommended action and text the system about their heath after performing the action. For example, the user 1348 may send that he/she is feeling well or feeling something else after having a mini meal.

Step 7: If the algorithm determines that the user health is still not good then perform the steps 4-7.

Figure 24:
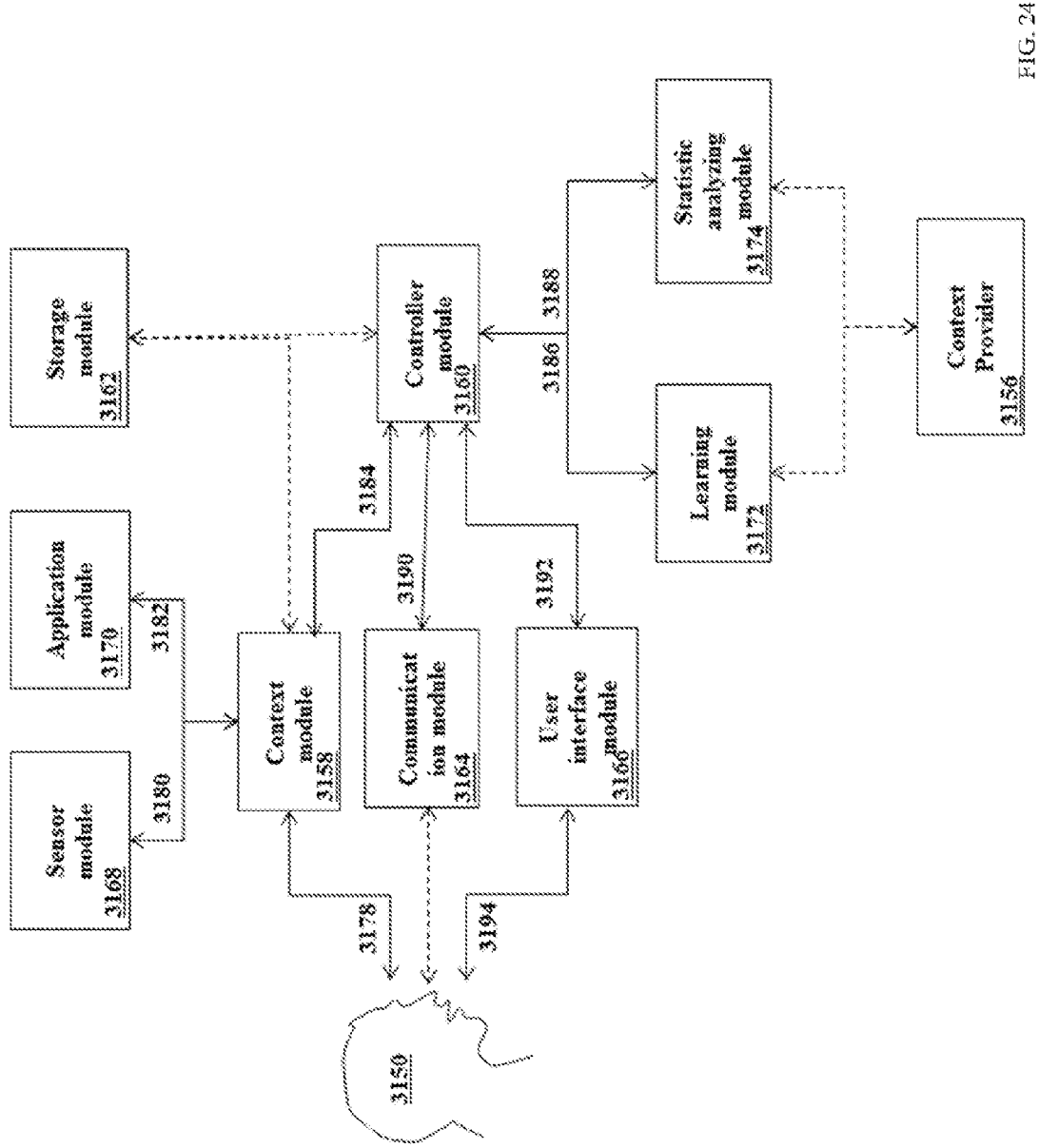
FIG. 24 shows exemplary operations performed by the system as described in the FIGS. 20 and 21.

FIG. 24 shows exemplary operations performed by the system as described in the FIGS. 20 and 21. In an example, at 3178, the context module 3158 can be configured to collect the user habit information. In an example, the context module 3158 can retrieve both the static and dynamic habits of the user via one or more sensors installed thereon. In an embodiment, at 3180, the context module 3158, in communication with the sensor module 3168, receive one or more dynamic habits information of the user 1348. The one or more dynamic habits information described herein can include for example, the user 1348 movements, location, direction, environment, activity, and the like. In an embodiment, at 3182, the context module 3158, in communication with the application module 3170, receive one or more static habits of the user 1348. The one or more static habits described herein can include for example, the user 1348 schedule, the user 1348 appointment dates, the user 1348 dates, the user 1348 medical records, the user 1348 historic activities, and the like.

In an embodiment, at 3184, the controller module 3160, in communication with the context module 3158, can be configured to provide preventive health care recommendations to the user 1348. In an example, the controller module 3160 can predict the preventive health care recommendation based on the one or more habits information received from the context module 1358. In an embodiment, the controller module 3160 can interact with the learning module 3172 such as to determine the recommendations for the one or more habits information of the user 1348. In an embodiment, the learning module 3172 can be configured to include historic information about the treatments, solutions, advice, diseases, and the like information associated with the one or more users having similar (or substantially similar/same) habits. In an example, the learning module 3172 can interface with doctors system and includes doctors/physicians suggestion, approvals, advice, recommendations for the user 1348 based on the one or more habits. In an embodiment, the controller module 3160, in communication with the statistics analyzing module 3174, can be configured to use the statistical information about the one or more received habits of the user 1348 with the solutions, recommendations, advice, and other information offered to the one or more users, who have similar (or substantially similar/same) habits. In an embodiment, the controller module 3160 can be configured to apply one or more rules and determine the one or more recommendations applicable for the user 1348 based on the one or more habits of the user 1348. The rules specify the recommendations for the user 1348 based on the user habits information and based on the historic information of the one or more users having similar or same habits.

In an embodiment, at 3190, the controller module 1360, in communication with the communication module 3164, can be configured to provide the one or more predicted preventive health care recommendations to the user 1348. In an embodiment, the recommendations can be provided to the user 1348 in the form of an alert message such as an SMS, an email, a voice message, a video message, and the like. In an embodiment, at 3192, the controller module 1360, in communication with the graphical user interface module 3166, can be configured to display the one or more recommendations on the user portable electronic device. In an embodiment, at 3194, the user interface module 3166 can be configured to allow the user 1348 to perform one or more actions. For example, if based on the user habits, the recommendation provided to the user 1348 are to consult a doctor as soon as possible then the user 1348 can uses the user interface module 3166 to book an appointment with the doctor. In another example, if based on the user habits, the recommendation provided to the user to have a mini meal (including a glass of milk and egg) then the user 1348 can take the mini meal and respond to the portable electronic device 1350 about his/her health information after taking the mini meal. In an example, the user 1348 can respond using the user interface module 1366 or by sending an SMS, a voice message, an email, a video message, or the like.

Figure 25:
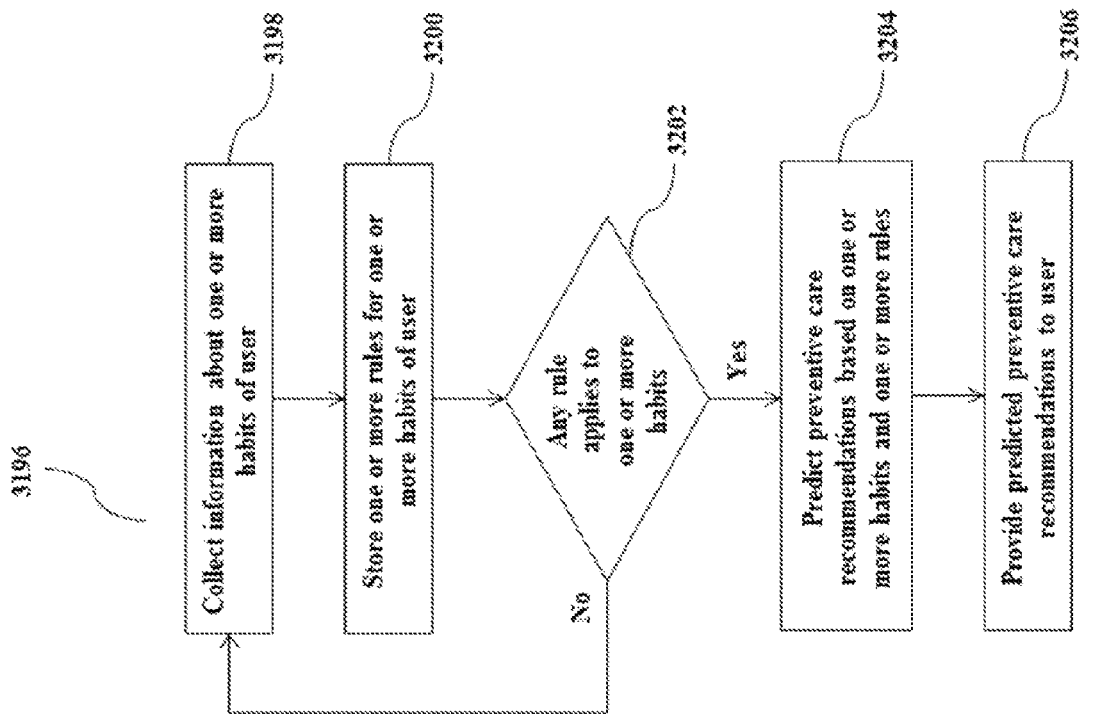
FIG. 25 shows a flow chart illustrating a method for providing preventive health care recommendations to the user.

FIG. 25 shows a flow chart illustrating a method 3196 for providing preventive health care recommendations to the user 3148. At 3198, the method 3196 includes collecting information about one or more habits of the user 1348. In an example, the method 3196 uses the context module 3158 to collect information about the one or more habits of the user 1348. In an example, the context module 3158 can be configured to retrieve both the static and dynamic habits of the user via one or more sensors installed thereon. In an embodiment, the method 1396 uses the sensor module 3168 to receive the one or more dynamic habits of the user 1348. The one or more dynamic habits described herein can include for example, the user 1348 movements, location, direction, environment, activities, and the like. In an embodiment, the method 1396 uses the application module to receive one or more static habits of the user 1348. The one or more static habits described herein can include for example, the user 1348 schedule, the user 1348 appointment dates, the user 1348 dates, the user 1348 medical records, the user 1348 historic activities, and the like.

In an embodiment, at 3200, the method 3196 includes storing one or more rules for one or more habits of the user 1348. In an embodiment, the method 1396 uses the storage module 3162 to store the one or more rules, which defines the one or more recommendations applicable for the user 1348. Further, the method 1396 enables the storage module 3162 to store the one or more habits of the user 1348.

In an embodiment, at 3202, the method 3196 includes determining if any of the one or more rules applies for the one or more habits received from the user 1348. The method 1396 uses the controller module 3160 to determine if any of the rules applies for the one or more habits received from the user 1348. In an embodiment, in response to determining that none of the rules applies for the one or more habits received from the user, the method 1396 includes repeating the steps 3198 through 3202.

In an embodiment, in response to determining that the one or more rules applies for the one or more habits received from the user 1348, the method 1396 includes predicting preventive care recommendations based on the one or more habits and the one or more rules. The method 1396 allows the controller module 3160 to predict the preventive health care recommendation based on the one or more habits information received from the context module 1358. In an embodiment, the method 1396 uses the learning module 3172 such as to determine the recommendations for the one or more habits. In an embodiment, the learning module 3172 includes historic information about the treatments, solutions, advice, diseases, and the like information associated with the one or more users having similar (or substantially similar/same) habits such as the habits of the user 1348. Further, the method 1396 allows the learning module 3172 to interface with the doctors system and includes doctors/physicians suggestion, approvals, advice, and recommendations for the user 1348 based on the one or more habits. In an embodiment, the method 1396 uses the statistics analyzing module 3174 use the statistical information about the one or more received habits of the user 1348 with the solutions, recommendations, advice, and other information offered to the one or more user, who may have similar (or substantially similar/same) habits. In an embodiment, the method 1396 includes applying the one or more rules and determining the one or more recommendations application for the user 1348 (based on the one or more habits received of the user 1348). The rules described herein specify the recommendations for the user 1348 based on the user habits information and based on the historic information of the one or more users having similar or same habits.

In an embodiment, at 3206, the method 1396 includes providing the predicted preventive care recommendations to the user 1348. In an embodiment, the method 1396 uses the controller module 3164 to provide the one or more predicted preventive health care recommendations to the user 1348. In an embodiment, the recommendations can be provided to the user 1348 in the form of an alert message such as an SMS, an email, a voice message, a video message, and the like. In an embodiment, the method 1396 uses the graphical user interface module 3166 to display the one or more recommendations on the user portable electronic device. For example, if based on the user habits, the recommendation provided to the user 1348 are to take some tablets on regular basis then the user 1348 uses the user interface module 3166 to order medicines from a chemist shop. In an example, the user 1348 can respond about his/her health after taking the medicines. In an example, the user 1348 can respond using the user interface module 1366 or by sending an SMS, a voice message, an email, a video message, or the like.

In an embodiment, different examples of the system and method for determining predictive health care recommendation for the user based on patient/user natural habits and one or more stored rules are described. In an example, analysis and display of the blood glucose level is described. The level is automatically stored in the storage module 3162. The system is configured to constantly monitor user health information and apply one or more rules such as to provide preventive health care recommendations to the user. For example, if the blood glucose is above a threshold (e.g., 250 mg/dl), meal tagging and feel tagging information or any other inquiries and information can be requested and input by the user. The user may provide the information to the system. If the input from the user indicates that it is more than two hours since the meal, or if the patient is feeling unwell, then the system execute the one or more rule and may recommend the patient to undertake ketone testing. If the patient is feeling fine and recently ate, then a message can be displayed stating, e.g., "glucose level is slightly high" and the associated recommendation recommending "exercise or drink water" is provided. In an example, the system may provide a message displaying "glucose level is slightly low and associated recommendation recommending drink fruit juice" is provided. In an example, based on the recommendation to undertake ketone testing, the results of ketone testing and blood glucose, and the patient input can be analyzed by the system. The system applies one or more rules and determines appropriate recommendations are generated advising the user to, for example, but not limited to, eat, begin exercise, stop exercise, and administer medication.

In another example, the system can be used to track patient preferences, especially those relating to obesity involving recommendations related to diet and exercise. The recommendations for eating can be highly specific and personalized according to the user favorite food and habits. For example, eat X calories of carbohydrates selected from "your favorite veg. or non-veg. food" (e.g., mashed potatoes and green beans). Eat X calories of proteins selected from your favorite shrimp and egg whites. Similarly recommendations for exercise can include duration and exertion level. These recommendations can be provided to the user by executing the one or more rules, which includes access to the user static habits (such as the user favorite food) and the user current health conditions such as fatness, weight, and the like. The system analyzes the user current health information and executes the one or more rules to provide appropriate recommendations advising the user to eat kind of food which is rich in protein, calories, and the like and which can be easily acquired through the user favorite food items.

In an example, the system can also provide personalized recommendations based on the user information. For example, if a user is so obese that he/she cannot walk, then "start walking" would not be a transmitted recommendation for the user in response to test results showing that the user has increased blood glucose. In an example, the user preferences for particular food likes and dislikes, along with their personal preferences for exercise type, exertion level, timings, the user subjective reactions such as general well-being, lethargy, light-headedness, nausea, severe headache, and the like parameters are considered in the one or more rules such as to determine recommendations for the user. In an example, the user's reaction to the recommended course of action may be applied in analysis and determination of further recommendations for the user.

The system and method can be used to monitor any type health related data of the user such as diabetes level, blood pressure, heart diseases, the user weight, body mass index (BMI), obesity level, hear rate, and the like and send appropriate reminders and recommendations to take medications or actions at appropriate time. The system and method can also be used to interface with other social and medical health information exchange platform such as to take advice from the heal care providers about the reactions or habits of the user such that effective recommendations can be provided to the user.

In an implementation, various user preferences on exercises are entered and considered and compatible exercises are recommended. For example, if the user is going over weight and the user likes running then the system may recommend the user to run for at least X minutes a day to maintain his/her weight. As the user likes vigorous exercise like running, other vigorous exercise like swimming, mountain hiking, wall climbing, triathlon training, and the like can be recommended to the user. In another example, if a patient indicates that they like corn because it's soft and sweet then the system can recommend other foods with similar attributes such as yams.

In an implementation, the system can constantly monitor the user health information. In an example, the system may uses external or internal sensors, or may enquire from the user to provide user health information. If the system determines that the blood glucose (BG) level is low then the system may execute the one or more rules and send a message displaying "your BG is very low" and recommend "eat a simple sugar snack of 15 g and input the health/feeling information after 15 minutes". In an example, the system may recheck (or receive a message from the user) the health information of the user after 15 minutes. If the system determines that the BG is in the target range then the system may send a message displaying "Good Work! Your BG is in target range" and may provide recommend "keep consuming X number of calories and Y number of proteins every day". In an example, if the system determines that the BG is above a target range then the system may execute the one or more rules and send a message displaying "Your BG is above the target range" and recommend "eat carefully and stop consuming deserts". In an example, if the system determines that the BG is very high then the system may execute the one or more rules and send a message displaying "Your BG is high" and recommend "check ketones". In an example, if the system determines that the BG is constantly high then the system may execute the one or more rules and send a message displaying "your BG is constantly high" and recommend "Caution! Consult your physician immediately". In an example, the system can be configured to automatically book appointments with the physician and alerts the user to go and meet the physician at the scheduled time.

In an implementation, the one or more rules may include rules related to trends of the BG. For example, when X number of reading continuously shows the BG level less than 60 within 24-48 hours then the system may send a message displaying "Caution! Consult your physician immediately". In an example, the system can automatically book appointment with the physician and alerts the user to go and meet the physician at the scheduled time. In an example, if the Y number of consecutive readings is greater than 240 then the system then the system may execute the one or more rules and send a message displaying "Caution! Consult your physician immediately". In an example, if the 3 consecutive readings are greater than 350 then the system may execute the one or more rules and send a message displaying "Caution! Consult your physician immediately". In an example, the system may stop generating further recommendations upon observing such trends of BG in the user and constantly recommends the user to consult the physician.

In an implementation, the one or more rules may include rules related to the trends of the BG for a specific time period. For example, if the BG is 71-110 for 7 days then a message displaying "7 day results: Great work, you have stayed in the target range". If the BG is 141-240 for 7 days then a message displaying "7 days results: you are above the target range, eat carefully" and recommend "eat food rich in calories and proteins such as eggs". Further, the system can be configured to provide useful treatment tips based on the periodic trends. An example of such tips may include "Avoid sugars product when the BG is low or high". Furthermore, the system can be configured to provide periodic recommendations of medicines and items to the user. For example, the system may send a message displaying "Your XXX tablets are about to complete" and recommend "press *** to go to the chemist shop and order the tablets".

In an example, the system may constantly monitor the user obesity level. The system is configured to store standard weight and BMI (body mass index) such as to determine the user obesity level. The system may monitor the user current weight and executes one or more rules such as to determine appropriate recommendations for the user. The system uses the user current weight and height information and determines the BMI index of the user. For example, based on the one or more rules, if the system determines that the user BMI is greater than or equal to 18.5 and less than 24.9 then the system may send a message displaying "Good for you. Try not getting the weight". If the system determines that the user BMI is less than 8.5 then the system may send a message displaying "You are under weight! Try gaining weight" and recommend "Try eating high calorie and protein foods such as eggs, breads, green leafy vegetables, and the like based on the use favorite food items". If you want to gain weight then it's important to gain slowly. So the system may provide recommendations suggesting how much amount of calories, proteins, fat, and the like should be consumed by the user.

In an example, if the BMI is greater than 25 and less than 29.9 then the system may send a message "you are overweight, try losing some weight" and recommend "Do exercise regularly". In an example, the system may suggest the time, type of exercise, and diet the user should follow to maintain the weight. Further, the system may measures the user waist size such as to provide appropriate recommendation to the user. The system may consider different parameters such as the user blood pressure, blood glucose level, the user heart rate, the user cholesterol level, the user tobacco use, the user diabetes status, the user age, the user family history ((having a father or brother diagnosed with heart disease before age 55 or having a mother or sister diagnosed before age 65), the user physical activities, and the like to provide further exercise related recommendations to the user.

In an example, if the BMI is greater than 30 then the system can send a message displaying "You are obese and you must lose weight" and recommend "diet and exercise schedule for the user". If you want to lose weight then it's important to lose slowly. So the system may provide recommendations suggesting how much amount of calories, proteins, fat, exercise, and the like should be followed by the user. The system may provide recommendations such as "lose no more than 1 pound to 2 pounds a weak" or "begin with a goal of losing 10 percent of your current weight". In an example, one pound equals 3,500 calories and to lose 1 pound a week, you need to eat 500 calories or burn 500 calories. It's best to work out some combination of both eating less and being more physically active. Further, the system may provide daily tips to the user such as "the healthiest way to lose weight and offers the best chance of long-term success is to lose it slowly". The system may consider different parameters such as the user blood pressure, blood glucose level, the user heart rate, the user cholesterol level, the user tobacco use, the user diabetes status, the user age, the user family history (having a father or brother diagnosed with heart disease before age 55 or having a mother or sister diagnosed before age 65), the user physical activities, and the like to provide further exercise related recommendations and tips to the user.

Furthermore, the diet recommendations including the amount of calories, proteins, and the like that needs to be consumed in a day is provided to the user. The factors that the system may considers while providing the diet related recommendations to the user includes for example, but not limited to, body size, the user physical activities such as the user common activates (e.g., washing and waxing a car for 45-60 minutes, washing windows or floors for 45-60 minutes, gardening for 30-45 minutes, wheeling self in wheelchair for 30-40 minutes, pushing a stroller 2 miles in 30 minutes, raking leaves for 30 minutes, shoveling snow for 15 minutes, stair walking for 15 minutes, and so on), user sporting activities (e.g., playing volleyball for 45-60 minutes, playing touch football for 45 minutes, walking 2 miles in 30 minutes, shooting baskets for 30 minutes, bicycling 5 miles in 30 minutes, dancing fast (social) for 30 minutes, performing water aerobics for 30 minutes, swimming laps for 20 minutes, playing basketball for 15-20 minutes, jumping rope for 15 minutes, running 2 miles in 15 minutes, and so on), and the like.

Furthermore, examples of the one or more rules considering different parameters and user habitual information are described. In an example, if the user is diabetic and the user is fasting then the system may provide recommendation suggesting "eat X number of calories extra for the day and do just normal exercise". If the user diabetes level is high and the user has high blood pressure then the system may provide recommendation suggesting "take insulin immediately and have a glass of juice with a mini meal". If the user is feeling head ache, and the blood pressure level is high then the system may provide recommendation suggesting "drink a glass of milk and sleep for an hour". If the user weight is 150 lbs and then the system may provide recommendation suggesting "ride a bicycle at 6 mph, you will burn 240 calories". If the user weight is 150 lbs and the user can run at 5.5 mph then the system may provide recommendation suggesting "Run for 1 hour today so that you will lose 660 calories". If the user weight is 150 lbs and the user can walk at 2 mph then the system may provide recommendation suggesting "Walk 4 km today and to burn 240 calories". If the user weight is 150 lbs and the user can swim at 25 yards/minute then the system may provide recommendation suggesting "swim for at least 1.5 hours to lose 275 calories". If the user weight is 150 lbs and the user likes playing tennis single then the system may provide recommendation suggesting "play tennis for 2 hours to burn 400 calories". If the user BMI indicates user is getting over weight and currently riding in elevator then the system may execute the one or more rules to provide recommendation suggesting "You are getting overweight! Decrease the weight by taking stairs instead of the elevator". If the system determines that the user is preparing weekly menu for the shopping then the system executes the one or more rules and provide recommendations suggesting "You work ten hours a day! So be sure to include healthy snacks and soups to fresh-up yourself during the work". If the system determines the user is suffering from tooth ache then the system may uses the rules related to the user brushing times and may provide recommendation suggesting "brush your teeth twice daily to take care of your teeth. Brush at least for 3 minutes to clean all your teeth well".

Furthermore, the system may include one or more rules to provide tips to the user based on the habits information. If the user is doing exercise then the system may provide the tip "Keep Going! Your body will develop endurance & strength with regular exercise". The tips to the user are provided based on the user information such as age, sex, and the like. For example, if the user is doing exercise and the user age is 22, then the system may provide a tip displaying "An average adult need 2 hours and 30 minutes of moderate intensity or 1 hour and 15 minutes of Vigorous intensity aerobic activity every week". In an example, if the user is eating snacks or the static habit indicate the user likes eating snacks every day then the system may provide a tip displaying "plan your snacks for the day only when you need it the most and eat only nutrient dense snack" or "Choose you snack smartly! A good snack is less than 150 calories per serving and gives you some protein".

In an embodiment, an example pseudo code that asks the user for his/her weight and height and then calculates the BMI (body mass index) to provide associated recommendations to the user is shown below:
Display "Please enter your height in inches"
Store input as height.
Display "Please enter your weight in pounds"
Store input as pounds
Calculate BMI as weight×(height) (height)
Display "Your BMI is" and BMI
Determine Recommendation based on BMI and one or more rules
Display "You are suggested to" Recommendation(s)

In an example, the pseudo code shows each step that can be included in the logic. All logic can be done every time. However, logic could be added to the program so that the program provide different recommendations based on the BMI and other habits (such as the user age, the user gender, the user health, the user conditions, the user activities, the user likes, the user dislikes, the user interests, the user favorite food, the user feelings, the user location, and the like) associated with the user. For example:
Display "Please enter your height in inches"
Store input as height.
Display "Please enter your weight in pounds"
Store input as pounds
Calculate BMI as weight×(height) (height)
Display "Your BMI is" and BMI
If the BMI is greater than or equal to 18.5 and less than 24.9
   Display "Good for you. Try not getting the weight"
   Determine recommendations based on BMI, the user habits, the one or more rules
   Display "Keep maintaining the same diet"
If the BMI is less than 18.5
   Display "You are under weight! Try gaining weight"
   Determine recommendations based on BMI, the user habits, the one or more rules
   Display "Try eating high calorie and protein foods such as eggs, breads, green leafy vegetables, and the like based on the use favorite food items"
   Determine number of calories & proteins needs to be consumed by the user based on the rules
   Display "The number(s) of calories & proteins that must be consumed are" calories and proteins
If the BMI greater than 25 and less than 29.9
   Display "You are overweight, try losing some weight"
   Determine recommendations based on BMI, the user habits, the one or more rules
   Display "Do exercise regularly"
If the BMI is greater than 30
   Display "You are obese and you must lose weight"
   Determine recommendations based on BMI, the user habits, the one or more rules
   Display "Diet and exercise schedule for the user" Diet and Schedule
   Determine pounds to be loosed weekly based on the rules
   Display "Lose no more than 1 pound to 2 pounds a weak"
The indention after the line that begins with "If" indicates that this logic can only be done when the "if" logic is true.

An example pseudo code for determining the user Blood Glucose (BG) level and the one or more habits, and executing one or more rules to determine appropriate recommendations for the user is described below:
Determine user habits information (including the user BG level)
If the BG is greater than 250 mg
   Display "How long back to have your meals"
   Store user input as meals information
   If the input from the user indicates that it is more than two hours since the meal
      Determine recommendations for the user based on one or more rules
      Display "Please undertake ketone testing"
   If the input from the user indicates the user just had the meal
      Determine recommendations for the user based on one or more rules
      Display "Glucose level is slightly high. Please exercise or drink water"
If the blood glucose (BG) level is low
   Determine recommendations for the user based on one or more rules Display "Your BG is very low. Eat a simple sugar snack of 15 g and input the health/feeling information after 15 minutes"
Display "Please provide your feeling or health information after taking the snack"
If the input indicates the user is feeling well and the BG is in the target range
    Determine recommendations for the user based on one or more rules
    Display "Good Work! Your BG is in target range. Please keep consuming X number of calories and Y number of proteins every day"
If the BG is above a target range
    Determine recommendations for the user based on one or more rules
    Display "Your BG is above the target range. Please eat carefully and stop consuming deserts"
If the BG is very high
    Determine recommendations for the user based on one or more rules
    Display "Your BG is high. Check ketones"
An example pseudo code determining trends of the BG and executing one or more rules to determine appropriate recommendations for the user is described below:
Determine the user BG level
Check trends of the BG
If 5 reading continuously shows the BG level is less than 60 within 24-48 hours
    Determine recommendations for the user based on one or more rules
        Display "Caution! Consult your physician immediately"
        Book an appointment with doctor
        Display "Your appoint is schedule for tomorrow"
        Alert the user to go and meet the physician at the scheduled time
If 4 reading continuously shows the BG level is greater than 240
    Determine recommendations for the user based on one or more rules
        Display "Caution! Consult your physician immediately"
        Book an appointment with doctor
        Display "Your appoint is schedule for Today at 2:00 PM"
        Alert the user to go and meet the physician at the scheduled time
If 3 reading continuously shows the BG level is greater than 352
    Determine recommendations for the user based on one or more rules
        Display "Caution! Consult your physician immediately"
        Book an appointment with doctor
        Display "Your appoint is schedule for Tomorrow at 3:00 PM"
        Alert the user to go and meet the physician at the scheduled time
An example pseudo code determining trends of the BG for a specific time period and executing one or more rules to determine appropriate recommendations for the user is described below:
Determine the user BG level
Check trends of the BG for entire weak
If the BG is 71-110 within last 7 days
    Determine recommendations for the user based on one or more rules
    Display "7 day results: Great work, your BG is in the target range. Continue same diet and exercise plan"
If the BG is 141-240 for 7 days
    Determine recommendations for the user based on one or more rules
    Display "7 days results: you are above the target range. Eat food rich in calories and proteins such as eggs"
An example pseudo code for determining periodic recommendations is described below:
Determine user habits information
Check stored user information
Determine recommendations for the user based on one or more rules
Display "Your XXX tablets are about to complete, Please press *** to go to the chemist shop and order the tablets"
If the user presses ***
    Order XXX tablets through chemist shop
    Display "The XXX tablets are successfully ordered"
An example pseudo code for determining the one or more habits of the user and executing one or more rules to determine appropriate recommendations for the user is described below:
Determine user habits information
If the user is diabetic and the user is fasting
    Determine recommendations for the user based on one or more rules
    Display "Eat X number of calories extra for the day and do just normal exercise"
If the user diabetes level is high and the user blood pressure level is high
    Determine recommendations for the user based on one or more rules
    Display "Take insulin immediately and have a glass of juice with a mini meal"
If the user is feeling head ache and the user blood pressure level is high
    Determine recommendations for the user based on one or more rules
    Display "Drink a glass of milk and sleep for an hour"
If the user weight is 150 lbs
    Determine recommendations for the user based on one or more rules
    Display "Ride a bicycle at 6 mph, you will burn 240 calories"
If the user weight is 150 lbs and the user can run at 5.5 mph
    Determine recommendations for the user based on one or more rules
    Display "Run for 1 hour today so that you will lose 660 calories"
If the user weight is 150 lbs and the user can walk at 2 mph
    Determine recommendations for the user based on one or more rules
    Display "Walk 4 km today and to burn 240 calories"
If the user weight is 150 lbs and the user can swim at 25 yards/minute
    Determine recommendations for the user based on one or more rules
    Display "swim for at least 1.5 hours to lose 275 calories"
If the user weight is 150 lbs and the user likes playing tennis single
    Determine recommendations for the user based on one or more rules
    Display "Play tennis for 2 hours to burn 400 calories"
If the user BMI 29 and currently riding in elevator
    Determine recommendations for the user based on one or more rules
    Display "You are getting overweight! Decrease the weight by taking stairs instead of the elevator"
If the user is preparing weekly menu for the shopping Determine recommendations for the user based on one or more rules
Display "You work ten hours a day! So be sure to include healthy snacks and soups to fresh-up yourself during the work"
If the user is suffering from tooth ache
Determine recommendations for the user based on one or more rules
Display "Brush your teeth twice daily to take care of your teeth. Brush at least for 3 minutes to clean all your teeth well"
An example pseudo code for determining the one or more habits of the user and executing one or more rules to determine appropriate tips/education messages for the user is described below:
Determine the user habits information
If the user is doing exercise
Determine tips/education message for the user based on one or more rules
Display "Keep Going! Your body will develop endurance & strength with regular exercise"
The tips to the user are provided based on the user information such as age, sex, and the like. For example:
If the user is doing exercise and the user age is 22
Determine tips/education message for the user based on one or more rules
Display "An average adult need 2 hours and 30 minutes of moderate intensity or 1 hour and 15 minutes of Vigorous intensity aerobic activity every week"
If the user is eating snacks or the static habit indicate the user likes eating snacks every day
Determine tips/education message for the user based on one or more rules
Display "Plan your snacks for the day only when you need it the most and eat only nutrient dense snack" or "Choose you snack smartly! A good snack is less than 150 calories per serving and gives you some protein"

"Computer readable media" can be any available media that can be accessed by client/server devices. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by client/server devices. Communication media typically embodies computer readable instructions, data structures, program modules or other data in a modulated data signal such as a carrier wave or other transport mechanism and includes any information delivery media.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only. The above specification, examples and data provide a complete description of the manufacture and use of the composition of the invention. Since many embodiments of the invention can be made without departing from the spirit and scope of the invention, the invention resides in the claims hereinafter appended.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A system to provide automatic messaging to a client on behalf of a healthcare treatment professional, comprising:
   one or more wireless nodes;
   a processor coupled to one of the wireless nodes;
   a wearable mobile appliance in communication with the client and one or more wireless nodes; and
   one or more computer implemented agents each specializing in a disease state with rules executed by the processor, the rules being selected to respond to a client communication relating to a predetermined health condition, each agent communicating with another computer implemented agent, the client or the treatment professional, wherein upon receiving a communication from the client, the processor selects one or more computer implemented agents to interact with the client and send an instruction promoting healthy client behavior.

2. The system of claim 1, comprising computer readable code to:
   collect information on client;
   select a treatment template based on treatment plan for people with characteristics similar to the client;
   generate a treatment plan from the treatment template and customize the treatment plan; and
   obtain approval from the treatment professional.

3. The system of claim 1, comprising
   a camera to collect through an image a calorie content of an item to be consumed and
   calorie detection code to automatically process the image to determine the calorie of the item.

4. The system of claim 3, comprising code to automatically identify volume and content of the item.

5. The system of claim 3, comprising code to automatically determine if the item is part of a recommended nutritional guideline and to send messages suggesting alternatives that replace or supplement the item to at least meet the recommended nutritional guideline.

6. The system of claim 1, comprising at least one Micro-Electro-Mechanical System (MEMS) device to collect client condition.

7. The system of claim 1, comprising code to model patient movements and convert the patient movements into energy consumption.

8. The system of claim 1, comprising code to model calorie usage from exercises and adapt client diet in response to the exercises.

9. The system of claim 1, comprising code to accumulate reward points for the client to encourage healthy activities.

10. The system of claim 1, comprising code to compare client progress with similarly situated people and send normative messages to improve client progress.

11. A method to provide automatic messaging to a client on behalf of a healthcare treatment professional, comprising:
    setting up one or more computer implemented agents each specializing in a disease state with rules to respond to a client condition, wherein each agent communicates with another computer implemented agent, the client or the treatment professional;

during run-time, receiving a communication from the client and in response selecting one or more computer implemented agents to respond to the communication; and automatically formatting a response to be rendered on a client mobile device to encourage healthy behavior.

12. The method of claim 11, comprising:
collecting information on client;
selecting a treatment template based on treatment plan for people with characteristics similar to the client;
generating treatment plan from the treatment template and customizing the treatment plan; and
obtaining approval from the treatment professional.

13. The method of claim 11, comprising automatically collecting calorie content of an item to be consumed with a processor controlled camera and calorie detection code to automatically process the image to determine the calorie of the item.

14. The method of claim 13, comprising automatically identifying volume and content of the item.

15. The method of claim 13, comprising automatically determining if the item is in a recommended nutritional guideline and sending messages suggesting alternatives that replace or supplement the item to at least meet the nutritional guideline.

16. The method of claim 11, comprising automatically collecting data on treatment plan compliance using at least one Micro-Electro-Mechanical System (MEMS) device.

17. The method of claim 1, comprising generating a diet plan personalized to the client and meeting a predetermined dietary guideline.

18. The method of claim 17, comprising modeling calorie usage from client exercises and adapting a client diet plan in response to the exercises.

19. The method of claim 11, comprising accumulating reward points for the client to encourage healthy activities.

20. The method of claim 11, comprising comparing client progress with similarly situated people; and improving client progress through normative messaging.

21. A system, comprising:
a camera to capture an image of an item to be consumed; and
calorie detection code to process the image and automatically determine the calorie content of the item.

22. The system of claim 21, comprising a cellular transceiver coupled to the camera.

23. The system of claim 21, comprising computer readable code to:
collect information on a client;
select a treatment template based on treatment plan for people with characteristics similar to the client; and
generate a treatment plan from the treatment template and customize the treatment plan for the client.

24. The system of claim 21, comprising code to accumulate reward points for the client to encourage healthy activities.

25. The system of claim 21, comprising code to compare client progress with people with characteristics similar to the client; and code to improve client progress through normative messaging.

26. The system of claim 21, comprising code to determine calorie usage from client exercises and modify a client diet plan in response to the exercises.

\* \* \* \* \*